(12) United States Patent
Hirayama et al.

(10) Patent No.: US 8,022,208 B2
(45) Date of Patent: Sep. 20, 2011

(54) BENZENE DERIVATIVE OR SALT THEREOF

(75) Inventors: Fukushi Hirayama, Tokyo (JP); Jiro Fujiyasu, Tokyo (JP); Daisuke Kaga, Tokyo (JP); Kenji Negoro, Tokyo (JP); Daisuke Sasuga, Tokyo (JP); Norio Seki, Tokyo (JP); Ken-ichi Suzuki, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 797 days.

(21) Appl. No.: 12/091,099

(22) PCT Filed: Nov. 7, 2006

(86) PCT No.: PCT/JP2006/322133
§ 371 (c)(1),
(2), (4) Date: Apr. 22, 2008

(87) PCT Pub. No.: WO2007/055183
PCT Pub. Date: May 18, 2007

(65) Prior Publication Data
US 2009/0054352 A1  Feb. 26, 2009

(30) Foreign Application Priority Data

Nov. 8, 2005  (JP) .................... P.2005-323491

(51) Int. Cl.
| C07D 419/14 | (2006.01) |
| C07D 279/12 | (2006.01) |
| C07D 401/14 | (2006.01) |
| C07D 211/94 | (2006.01) |
| C07D 213/62 | (2006.01) |
| C07D 267/10 | (2006.01) |
| A61K 31/553 | (2006.01) |
| A61K 31/554 | (2006.01) |
| A61K 31/546 | (2006.01) |
| A61K 31/5355 | (2006.01) |
| A61K 31/497 | (2006.01) |
| A61K 31/445 | (2006.01) |
| A61K 31/444 | (2006.01) |

(52) U.S. Cl. .................... 544/194; 544/58.2
(58) Field of Classification Search .................. None
See application file for complete search history.

(56) References Cited

U.S. PATENT DOCUMENTS

| 2003/0191115 A1 | 10/2003 | Pinto et al. |
| 2003/0195193 A1 | 10/2003 | Hirayama et al. |
| 2004/0068109 A1 | 4/2004 | Hirayama et al. |
| 2004/0077555 A1 | 4/2004 | Ishihara et al. |
| 2004/0220174 A1 | 11/2004 | Pinto et al. |
| 2005/0124602 A1 | 6/2005 | Pinto et al. |
| 2005/0171085 A1 | 8/2005 | Pinto et al. |
| 2005/0261287 A1 | 11/2005 | Pinto et al. |
| 2005/0267097 A1 | 12/2005 | Pinto et al. |
| 2006/0287329 A1 | 12/2006 | Kawaguchi et al. |

FOREIGN PATENT DOCUMENTS

| JP | 2005-507889 | 3/2005 |
| WO | 01/74791 | 10/2001 |
| WO | 02/42270 | 5/2002 |
| WO | 03/026652 | 4/2003 |
| WO | 2005/030706 | 4/2005 |

*Primary Examiner* — Kamal Saeed
*Assistant Examiner* — Nyeemah A Grazier
(74) *Attorney, Agent, or Firm* — Fitzpatrick, Cella, Harper & Scinto

(57) ABSTRACT

Problem: To provide compounds which have an anticoagulation effect based on their ability to inhibit the activated blood coagulation factor X and are useful as coagulation inhibitors or agents for prevention or treatment for diseases caused by thrombi or emboli.

Means for Solution: Benzene derivatives or their salts having a characteristic chemical structure with a phenol ring and a benzene ring bonding to each other via an amide bond, in which the phenol ring further bonds to a benzene ring or a heteroaryl ring via an amide bond. They have an excellent effect of inhibiting the activated blood coagulation factor X, and especially have an excellent oral activity.

18 Claims, No Drawings

BENZENE DERIVATIVE OR SALT THEREOF

TECHNICAL FIELD

The present invention relates to novel benzene derivatives or salts thereof which are useful as medicines, especially as an activated blood coagulation factor X inhibitor.

BACKGROUND OF THE INVENTION

Recently, thromboembolic disorders, such as myocardial infarction, cerebral thrombosis and peripheral arteriothrombosis, are increasing year by year with the popularization of Western life-styles and the increase in aged population, and there is much increasing social demand for the treatment of such disorders. Anticoagulant therapy as well as fibrinolysis therapy and antiplatelet therapy is a part of medical therapy for treatment and prevention of thrombosis (Sogo Rinsho, 41: 2141-2145, 1989). In particular, anticoagulants for prevention of thrombosis indispensably require high safety for long-term administration and the ability of surely and appropriately expressing the anticoagulation activity. However, the anticoagulating ability of warfarin potassium, which is only one oral anticoagulant now being popularly used in the world, is difficult to control because of the characteristic of itself based on the action and the mechanism thereof (J. Clinical Pharmacology, 32, 196-209, 1992; and N. Eng. J. Med., 324 (26), 1865-1875, 1991), and the drug is extremely difficult to use in clinics; and the provision of anticoagulants that are more useful and are easier to use is expected.

It is known that thrombin acts to convert fibrinogen into fibrin in the final stage of coagulation, while deeply participating in the activation and the coagulation of platelets (Satoshi Matsuo's T-PA and Pro-UK, Gakusai Kikaku, pp. 5-40, Blood Coagulation, 1986), and its inhibitors have been the center of studies of anticoagulants as the target in drug development for a long period of time.

On the other hand, the activated blood coagulation factor X is an enzyme to produce thrombin that plays a key role of blood coagulation, and as it exists in the junction of intrinsic and extrinsic coagulation cascade reactions, its inhibitors could have a possibility of efficiently inhibiting blood coagulation systems (THROMBOSIS RESEARCH (19), 339-349, 1980). Further, It has been proved that, different from thrombin inhibitors, the activated blood coagulation factor X inhibitor does not have a platelet coagulation inhibiting effect but can specifically inhibit blood coagulation, and that, in a thrombotic model test with animals, it exhibits antithrombotic effect but not exhibiting a side effect of hemorrhage, and the inhibitor is therefor specifically noted (Circulation, 1991, 84, 1741).

As compounds having the ability of inhibiting the activated blood coagulation factor X, known are amidinonaphthylalkylbenzene derivatives or their salts (JP-A 5-208946; Thrombosis Haemostasis, 71 (3), 314-319, 1994; and Thrombosis Haemostasis, 72 (3), 393-396, 1994).

Patent Reference 1 (WO 01/74791) describes diazepane derivatives of the following general formula or their salts, as compounds having the ability of inhibiting the activated blood coagulation factor X. However, they differ from the compounds of the present invention in the structure in point of the presence or absence of diazepane.

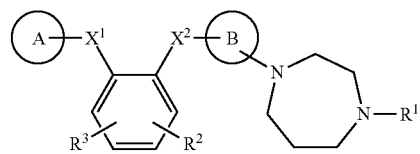

[Chem. 1]

(Ring A and ring B: the same or different, each representing an aryl or heteroaryl optionally having from 1 to 3 substituents; and the publication is referred to for the other symbols.)

Patent Reference 2 (WO 02/42270) describes substituted benzene derivatives of the following general formula or their salts, as compounds having the ability of inhibiting the activated blood coagulation factor X. However, they differ from the compounds of the present invention in the structure of the ring B.

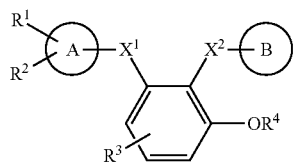

[Chem. 2]

(Ring A: benzene ring, or a 5- or 6-membered hetero ring having from 1 to 4, the same or different types of hetero atoms selected from N, S and O. Ring B: when $R^4$ is a hydrogen atom or —$SO_3H$, it is a piperidine ring of which the nitrogen atom is substituted with $R^7$, etc. The publication is referred to for the other symbols.)

Further, Patent Reference 3 (WO 03/26652) describe compounds of a general formula $P_4$—P-M-$M_4$ (M: 3 to 10-membered carbon ring, or 4- to 10-membered hetero ring. P: 5- to 7-membered carbon ring or 5- to 7-membered hetero ring condensed with the ring M, or it is absent. One of $P_4$ and $M_4$ is -Z-A-B, and the other is -$G_1$-G. The publication is referred to for the other symbols.), as compounds having the ability of inhibiting the activated blood coagulation factor X. However, they differ from the compounds of the present invention in the structure of -Z-A-B, etc.

Patent Reference 1: International Publication WO 01/74791
Patent Reference 2: International Publication WO 02/42270
Patent Reference 3: International Publication WO 03/26652

DISCLOSURE OF THE INVENTION

Problems that the Invention is to Solve

As described above, inhibitors for the activated blood coagulation factor X are effective in anticoagulant therapy, and are expected to provide specific inhibition of coagulation systems. Accordingly, development of selective inhibitors for the activated blood coagulation factor X, which differ from the above-mentioned known compounds in the chemical structure, of which oral administration is possible, and which have further excellent effects, is greatly expected.

Means for Solving the Problems

The present inventors have found that benzene derivatives of the following general formula (I) or salts thereof, which are characterized by the chemical structure in that the phenol ring and the benzene ring bond to each other via an amido bond and that the phenol ring further bonds to a benzene ring or a heteroaryl ring via an amido bond, have an excellent effect of inhibiting the activated blood coagulation factor X and have an especially excellent oral activity, resulting in accomplishment of the present invention. Specifically, the present invention relates to benzene derivatives of the following general formula (I) or (II) or salts thereof, and a pharmaceutical composition comprising the same as an active ingredient, especially an activated blood coagulation factor X inhibitor, [1] to [18].

[1] A benzene derivative of the following general formula (I) or a salt thereof:

[Chem. 3]

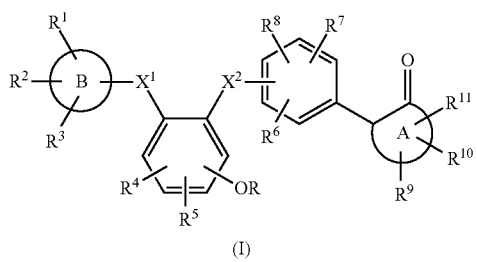

(I)

(the symbols in the above formula have the following meanings:

$X^1$: —$NR^{12}$—C(=O)— or —C(=O)—$NR^{12}$—,
$X^2$: —$NR^{13}$—C(=O)— or —C(=O)—$NR^{13}$—,

Ring A: 5- or 6-membered ring optionally having 1 or 2 double bonds and optionally having from 1 to 3 hetero atoms selected from N, S, O, Ring B: a benzene ring or 5- or 6-membered heteroaryl ring having from 1 to 3 hetero atoms selected from N, S, O, R: a hydrogen atom or a sugar residue, $R^1$ to $R^8$: the same or different, each representing a hydrogen atom, a halogen atom, optionally-substituted lower alkyl, —O-(optionally-substituted lower alkyl), —O-(optionally-substituted 4- to 8-membered hetero ring having from 1 to 3 hetero atoms selected from N, S, O), —CN, —$NH_2$, —N(optionally-substituted lower alkyl)$_2$, —NH(optionally-substituted lower alkyl), —NH(optionally-substituted 4- to 8-membered hetero ring having from 1 to 3 hetero atoms selected from N, S, O), —$NHSO_2$ (optionally-substituted lower alkyl), —N (optionally-substituted lower alkyl) $SO_2$ (optionally-substituted lower alkyl), —$NO_2$, —COOH, —$CO_2$(optionally-substituted lower alkyl), —$CONH_2$, —CONH(optionally-substituted lower alkyl), —CON(optionally-substituted lower alkyl)$_2$, —OH, —$(CH_2)_n$—$NH_2$, —$(CH_2)_n$—N(optionally-substituted lower alkyl)$_2$, or —$(CH_2)_n$—NH (optionally-substituted lower alkyl), $R^9$ to $R^{11}$: the same or different, each representing a hydrogen atom, a halogen atom, optionally-substituted lower alkyl, —O-(optionally-substituted lower alkyl), —CN, —$NH_2$, —N(optionally-substituted lower alkyl)$_2$, —NH (optionally-substituted lower alkyl), —$NHSO_2$(optionally-substituted lower alkyl), —N(optionally-substituted lower alkyl)$SO_2$ (optionally-substituted lower alkyl), —$NO_2$, —COOH, —$CO_2$(optionally-substituted lower alkyl), —$CONH_2$, —CONH(optionally-substituted lower alkyl), —CON(optionally-substituted lower alkyl)$_2$, —OH, —$(CH_2)_n$—N(optionally-substituted lower alkyl)$_2$, —$(CH_2)_n$—NH (optionally-substituted lower alkyl), —$(CH_2)_n$—$NH_2$, —$(CH_2)_n$—N(optionally-substituted 4- to 8-membered hetero ring having from 1 to 3 hetero atoms selected from N, S, O)$_2$, —$(CH_2)_n$—NH(optionally-substituted 4- to 8-membered hetero ring having from 1 to 3 hetero atoms selected from N, S, O), —$(CH_2)_n$—N(optionally-substituted lower alkyl)(optionally-substituted 4- to 8-membered hetero ring having from 1 to 3 hetero atoms selected from N, S, O), —$(CH_2)_n$—(C=O)—N(optionally-substituted lower alkyl)$_2$, —$(CH_2)_n$—(C=O)—NH(optionally-substituted lower alkyl), —$(CH_2)_n$—(C=O)—$NH_2$, —$(CH_2)_n$—(C=O)—N(optionally-substituted 4- to 8-membered hetero ring having from 1 to 3 hetero atoms selected from N, S, O)$_2$, —$(CH_2)_n$—(C=O)—NH(optionally-substituted 4- to 8-membered hetero ring having from 1 to 3 hetero atoms selected from N, S, O), —$(CH_2)$, —(C=O)—N(optionally-substituted lower alkyl)(optionally-substituted 4- to 8-membered hetero ring having from 1 to 3 hetero atoms selected from N, S, O), —$(CH_2)_n$—O-(optionally-substituted lower alkyl), —$(CH_2)_n$ -(optionally-substituted 4- to 8-membered hetero ring having from 1 to 3 hetero atoms selected from N, S, O), —$(CH_2)_n$—O-(optionally-substituted 4- to 8-membered hetero ring having from 1 to 3 hetero atoms selected from N, S, O), or —$(CH_2)_n$—(C=O)-(optionally-substituted 4- to 8-membered hetero ring having from 1 to 3 hetero atoms selected from N, S, O), n: integer of from 0 to 6, $R^{12}$ and $R^{13}$: the same or different, each representing a hydrogen atom or lower alkyl, provided that, in $R^1$ to $R^{11}$, when two lower alkyls bond to a nitrogen atom, then they may be taken together to form a 3- to 8-membered nitrogen-containing hetero ring.)

[2] The compound or a salt thereof according to [1], wherein in the formula (I) of [1], the group:

[Chem. 4]

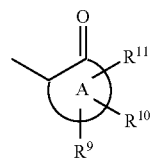

is a group of the following:

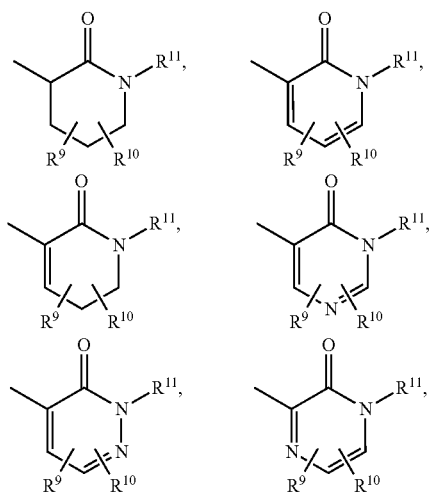

-continued

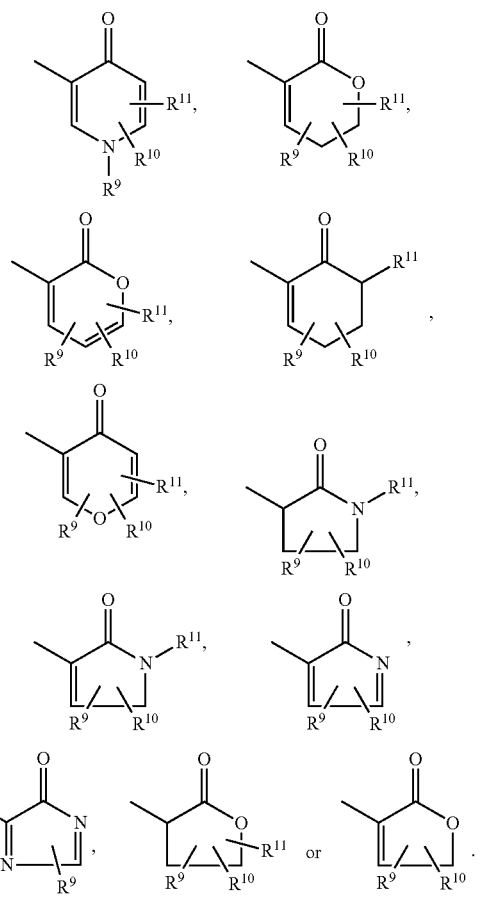

[3] The compound or a salt thereof according to [1], wherein in the formula (I) of [1], the group:

[Chem. 5]

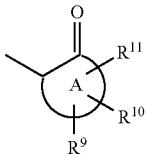

is a group of the following:

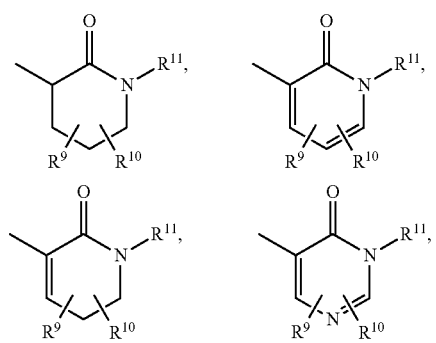

[4] The compound or a salt thereof according to [1], wherein in the formula (I) of [1], the group:

[Chem. 6]

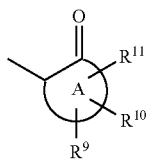

is a group of the following:

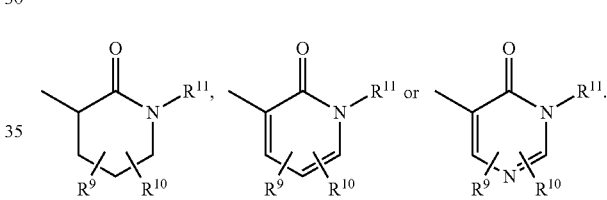

[5] The compound or a salt thereof according to [1] to [4], wherein in the formula (I) of [1], the ring B is a benzene ring or a pyridine ring.

[6] The compound or a salt thereof according to [1] to [5], wherein in the formula (I) of [1], R is a hydrogen atom or a sugar residue of glucuronic acid.

[7] The compound or a salt thereof according to [1] to [6], wherein the optionally-substituted 4- to 8-membered hetero ring having from 1 to 3 hetero atoms selected from N, S, and O is a hetero ring selected from azetidine, pyrrolidine, piperidine, azepane, azocane, piperazine, morpholine, thiomorpholine, 1,4-diazepane, 1,4-oxazepane, 1,4-thiazepane, 1,5-diazocane, 1,5-oxazocane, 1,5-thiazocane, imidazole, triazole, thiazole, oxazole, isoxazole, pyrazole, pyridine, pyrazine, or pyrimidine.

[8] The compound or a salt thereof according to [7], wherein the substituent in the optionally-substituted lower alkyl is from 1 to 3 substituents selected from —OH, CF$_3$, —CN, =O, —NH$_2$, —COOH, —COO-lower alkyl, —CONH$_2$, —CONH(lower alkyl), —CON(lower alkyl)$_2$, —O-lower alkyl, —NH(lower alkyl), —N(lower alkyl)$_2$, —NHCO(lower alkyl), —N(lower alkyl)CO(lower alkyl), —NHCONH$_2$, —NHCONH(lower alkyl), —NHCON(lower alkyl)$_2$, —N(lower alkyl)CONH(lower alkyl), —N(lower alkyl)CON(lower alkyl)$_2$, a halogen atom, —NHSO$_2$-(lower alkyl), —N(lower alkyl)SO$_2$—(lower alkyl), or —SO$_2$(lower alkyl), and the substituent in the optionally-substituted 4- to 8-membered hetero ring having from 1 to 3 hetero atoms selected from N, S, O is from 1 to 3 substituents selected from lower alkyl, —OH, $CF_3$, —CN, =O, —$NH_2$, —COOH, —COO-lower alkyl, —$CONH_2$, —CONH(lower alkyl), —CON(lower alkyl)$_2$, —O-lower alkyl, —NH(lower alkyl), —N(lower alkyl)$_2$, —NHCO(lower alkyl), —N(lower alkyl)CO(lower alkyl), —$NHCONH_2$, —NHCONH(lower alkyl), —NHCON(lower alkyl)$_2$, —N(lower alkyl)CONH(lower alkyl), —N(lower alkyl)CON(lower alkyl)$_2$, a halogen atom, —$NHSO_2$—(lower alkyl), —N(lower alkyl)$SO_2$—(lower alkyl), or —$SO_2$(lower alkyl).

[9] A benzene derivative of the following general formula (II) or a salt thereof:

[Chem. 7]

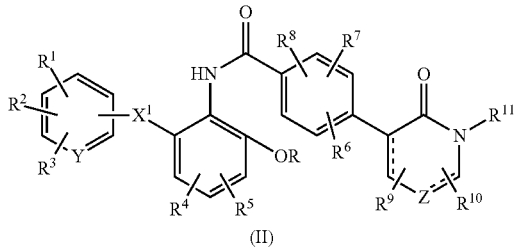

(II)

(The symbols in the above formula have the following meanings:

$X^1$: —NH—C(=O)— or —C(=O)—NH—,
Y: N or CH,
Z: N, NH, CH or $CH_2$,
R: a hydrogen atom or a sugar residue,
$R^1$ to $R^8$: the same or different, each representing a hydrogen atom, a halogen atom, lower alkyl, —O-lower alkyl, —O-(optionally-substituted 4- to 8-membered hetero ring having from 1 to 3 hetero atoms selected from N, S, O), —CN, —$NH_2$, —N(lower alkyl)$_2$, —NH(lower alkyl), —$NHSO_2$(lower alkyl) or $NO_2$,
$R^9$ to $R^{11}$: the same or different, each representing a hydrogen atom, a halogen atom, lower alkyl, —$(CH_2)_n$—N(optionally-substituted lower alkyl)$_2$, —$(CH_2)_n$—NH(lower alkyl), —$(CH_2)_n$—$NH_2$, —$(CH_2)_n$—N(optionally-substituted 4- to 8-membered hetero ring having from 1 to 3 hetero atoms selected from N, S, O)$_2$, —$(CH_2)_n$—NH(optionally-substituted 4- to 8-membered hetero ring having from 1 to 3 hetero atoms selected from N, S, O), —$(CH_2)_n$—N(lower alkyl) (optionally-substituted 4- to 8-membered hetero ring having from 1 to 3 hetero atoms selected from N, S, O), —$(CH_2)_n$—(C=O)—N(lower alkyl)$_2$, —$(CH_2)_n$—(C=O)—NH(lower alkyl), —$(CH_2)_n$—(C=O)—$NH_2$, —$(CH_2)_n$—(C=O)—N (4- to 8-membered hetero ring having from 1 to 3 hetero atoms selected from N, S, O)$_2$, —$(CH_2)_n$—(C=O)—NH(4- to 8-membered hetero ring having from 1 to 3 hetero atoms selected from N, S, O), —$(CH_2)_n$—(C=O)—N(lower alkyl) (4- to 8-membered hetero ring having from 1 to 3 hetero atoms selected from N, S, O), —$(CH_2)_n$—O-lower alkyl, —$(CH_2)_n$-(optionally-substituted 4- to 8-membered hetero ring having from 1 to 3 hetero atoms selected from N, S, O), —$(CH_2)_n$—O-(optionally-substituted 4- to 8-membered hetero ring having from 1 to 3 hetero atoms selected from N, S, O), or —$(CH_2)_n$—(C=O)-(optionally-substituted 4- to 8-membered hetero ring having from 1 to 3 hetero atoms selected from N, S, O),
n: integer of from 0 to 6,
provided that the dotted parts in the formula are the same or different, each meaning a single bond or a double bond, and in $R^1$ to $R^{11}$, when two lower alkyl groups bonds to the nitrogen atom, they may be taken together to form a 3- to 8-membered nitrogen-containing hetero ring.)

[10] The compound or a salt thereof according to [9], wherein in the formula (II) of [9], R is a hydrogen atom or a sugar residue of glucuronic acid.

[11] The compound or a salt thereof according to [1], selected from N-(5-chloropyridin-2-yl)-3-hydroxy-2-{[4-(1-methyl-4-oxo-1,4-dihydropyridin-3-yl)benzoyl]amino}benzamide, N-(5-chloropyridin-2-yl)-2-[(4-{1-[2-(dimethylamino) ethyl]-2-oxo-1,2-dihydropyridin-3-yl}benzoyl)amino]-3-hydroxybenzamide, N-(5-chloropyridin-2-yl)-3-hydroxy-2-[(4-{1-[2-(1,4-oxazepan-4-yl)ethyl]-2-oxo-1,2-dihydropyridin-3-yl}benzoyl)amino]benzamide, 5-chloro-N-(5-chloropyridin-2-yl)-3-hydroxy-2-{[4-(1-{2-[(1-methylpyridin-4-yl)oxy]ethyl}-2-oxo-1,2-dihydropyridin-3-yl)benzoyl]amino}benzamide, N-(5-chloropyridin-2-yl)-3-hydroxy-2-{[4-(1-methyl-2-oxo-1,2-dihydropyridin-3-yl) benzoyl]amino}benzamide, N-(5-chloropyridin-2-yl)-2-[(4-{1-[2-(dimethylamino)ethyl]-2-oxopiperidin-3-yl}benzoyl) amino]-3-hydroxybenzamide, 3-[(5-chloropyridin-2-yl) carbamoyl]-2-[(4-{1-[2-(dimethylamino)ethyl]-2-oxo-1,2-dihydropyridin-3-yl}benzoyl)amino]phenyl β-D-glucopyranosiduronic acid, N-(5-chloropyridin-2-yl)-3-hydroxy-2-[(4-{1-[2-(4-methylpiperazin-1-yl)ethyl]-2-oxo-1,2-dihydropyridin-3-yl}benzoyl)amino]benzamide, 4-{1-[2-(dimethylamino)ethyl]-2-oxo-1,2-dihydropyridin-3-yl}-N-{2-hydroxy-6-[(4-methoxybenzoyl)amino] phenyl}benzamide, N-(5-chloropyridin-2-yl)-3-hydroxy-2-[(4-{1-[2-(4-hydroxypiperidin-1-yl)ethyl]-2-oxo-1,2-dihydropyridin-3-yl}benzoyl)amino]benzamide, 5-chloro-N-(5-chloropyridin-2-yl)-2-[(4-{1-[2-(dimethylamino) ethyl]-2-oxo-1,2-dihydropyridin-3-yl}benzoyl)amino]-3-hydroxybenzamide, 3-[(5-chloropyridin-2-yl)carbamoyl]-2-[(4-{1-[2-(dimethylamino)ethyl]-2-oxopiperidin-3-yl}benzoyl)amino]phenyl β-D-glucopyranosiduronic acid.

[12] A pharmaceutical composition comprising the compound or a salt thereof according to [1] as an active ingredient.

[13] The pharmaceutical composition according to [12], which is an activated blood coagulation factor X inhibitor.

[14] The pharmaceutical composition of [12], which is an anticoagulant.

[15] Use of the compound or a salt thereof according to [1] or [9], for the manufacture of an activated blood coagulation factor X inhibitor.

[16] Use of the compound or a salt thereof according to [1] or [9], for the manufacture of an anticoagulant.

[17] A method for treating a patient with an activated blood coagulation factor X-associated disease, which comprises administering an effective amount of the compound or a salt thereof according to [1] or [9] to the patient.

[18] A method for treating a patient with a disease caused by thrombi or emboli, which comprises administering an effective amount of the compound or a salt thereof according to [1] or [9] to the patient.

The compound (I) of the present invention are described in detail hereinunder.

The term "lower" in the definition of general formulae in this description means a linear or branched carbon chain having from 1 to 6 carbon atoms, unless otherwise specifically indicated. Accordingly, "lower alkyl" includes, for example, methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl. Of those, preferred are the groups having from 1 to 3 carbon atoms, and more preferred are methyl, ethyl.

The "halogen atom" includes, a fluorine atom, a chlorine atom, a bromine atom, an iodine atom. Especially preferred are a chlorine atom and a bromine atom.

The ring A, "5- or 6-membered ring having 1 or 2 double bonds and optionally having from 1 to 3 hetero atoms selected from N, S, O" includes, for example, a saturated 6-membered ring such as cyclohexane, piperidine, piperazine, morpholine, thiomorpholine, tetrahydro-2H-pyran, tetrahydro-2H-thiopyran, 1,4-oxathiane; a double bond-having 6-membered ring such as cyclohexene, 1,2,3,6-tetrahydropyridine, 1,2-dihydropyridine, 1,4-dihydropyrimidine, 1,2-dihydropyrazine, 1,2,3,6-tetrahydropyrazine, 3,6-dihydro-2H-pyran, 2H-pyran, 3,6-dihydro-2H-thiopyran, 2H-thiopyran; a saturated 5-membered ring such as cyclopentane, pyrrolidine, tetrahydrofuran, tetrahydrothiophene; and a double bond-having 5-membered ring such as cyclopentadiene, 2,5-dihydro-1h-pyrrole, 2H-pyrrole, 2,5-dihydrofuran, 2,5-dihydrothiophene.

The ring A has ketone, naturally including an enol structure ring from keto-enol tautomerization. The ring A may have a double bond, and the ring A may have one or two double bonds. In case where the ring A is a 5-membered ring, $R^{10}$ and $R^{11}$ may be absent.

The ring B, "5- or 6-membered heteroaryl ring having from 1 to 3 hetero atoms selected from N, S, O" includes, for example, furan, thiophene, pyrrole, pyridine, oxazole, isoxazole, thiazole, isothiazole, furazane, imidazole, pyrazole, pyrazine, pyrimidine, pyridazine, triazine, triazole, tetrazole, which, however, are not limitative.

The substituent for "optionally-substituted lower alkyl" includes —OH, —CF$_3$, —CN, =O, —NH$_2$, —COOH, —COO-lower alkyl, —CONH$_2$, —CONH(lower alkyl), —CON(lower alkyl)$_2$, —O-lower alkyl, —NH(lower alkyl), —N(lower alkyl)$_2$, —NHCO(lower alkyl), —N(lower alkyl)CO(lower alkyl), —NHCONH$_2$, —NHCONH(lower alkyl), —NHCON(lower alkyl)$_2$, —N(lower alkyl)CONH(lower alkyl), —N(lower alkyl)CON(lower alkyl)$_2$, a halogen atom, —NHSO$_2$—(lower alkyl), —N(lower alkyl)SO$_2$—(lower alkyl), or —SO$_2$(lower alkyl).

The "4- to 8-membered hetero ring" of "4- to 8-membered hetero ring having from 1 to 3 hetero atoms selected from N, S, O" includes a saturated ring such as azetidine, pyrrolidine, piperidine, azepane, azocane, piperazine, morpholine, thiomorpholine, 1,4-diazepane, 1,4-oxazepane, 1,4-thiazepane, 1,5-diazocane, 1,5-oxazocane, 1,5-thiazocane; and an unsaturated ring such as thiazole, imidazole, triazole, thiazole, oxazole, isoxazole, pyrazole, pyridine, pyrazine, pyrimidine.

The substituent for "optionally-substituted 4- to 8-membered hetero ring having from 1 to 3 hetero atoms selected from N, S, O" includes lower alkyl, —OH, —CF$_3$, —CN, =O, —NH$_2$, —COOH, —COO-lower alkyl, —CONH$_2$, —CONH(lower alkyl), —CON(lower alkyl)$_2$, —O-lower alkyl, —NH(lower alkyl), —N(lower alkyl)$_2$, —NHCO (lower alkyl), —N(lower alkyl)CO(lower alkyl), —NHCONH$_2$, —NHCONH(lower alkyl), —NHCON(lower alkyl)$_2$, —N(lower alkyl)CONH(lower alkyl), —N(lower alkyl)CON(lower alkyl)$_2$, a halogen atom, —NHSO$_2$—(lower alkyl), —N(lower alkyl)SO$_2$—(lower alkyl), or —SO$_2$ (lower alkyl).

In the —N(optionally-substituted lower alkyl)$_2$ and the —N(lower alkyl)$_2$, the two substituents on the same nitrogen atom may differ.

The —N(optionally-substituted lower alkyl)$_2$ and the —N(lower alkyl)$_2$ may form a ring structure, taken together with the nitrogen atom. Concretely, they may form a 3- to 8-membered nitrogen-containing hetero ring. The nitrogen-containing hetero ring may further have from 1 to 3 hetero atoms.

Further, the ring A and the benzene ring must always bond to each other via the carbon atom on the ring A, and the present invention does not include a case where the ring A bonds to the benzene ring via the hetero atom on the ring A.

The "sugar residue" means a sugar residue of a monosaccharide. It may be a sugar residue derived from a sugar such as glucose, mannose, galactose, arabinose, xylose, ribose, N-acetylglucosamine, glucuronic acid, mannuronic acid, by removing one hydroxyl group, especially the 1-positioned hydroxyl group from it; however, it should not be limited to these but may include a sugar residue in which the hydroxyl group is substituted with a lower alkoxy group or the like. Preferred is a sugar residue of glucuronic acid.

The compounds of the present invention include mixtures or isolated ones of various stereoisomers such as geometric isomers, tautomeric isomers, optical isomers The compounds of the present invention may form acid-addition salts. Depending on the type of the substituent therein, the compounds may form salts with a base. Concretely, they include acid-addition salts with a mineral acid such as hydrochloric acid, hydrobromic acid, hydroiodic acid, sulfuric acid, nitric acid, phosphoric acid; an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid; or aspartic acid, glutamic acid; and salts with an inorganic base such as sodium, potassium, magnesium, calcium, aluminium; an organic base such as methylamine, ethylamine, ethanolamine; a basic amino acid such as lysine, ornithine; and ammonium salts.

Further, the present invention includes hydrates, pharmaceutically acceptable various solvates and polymorphic crystals of the compounds of the present invention. Naturally not limited to the compounds described in Examples to be given hereinunder, the present invention should encompass all the benzene derivatives of formulae (I) and (II) and their pharmaceutically acceptable salts.

In addition, the compounds of the present invention include compounds that are metabolized in living bodies to give compounds of formula (I) or their salts, or that is, prodrugs. The group of forming prodrugs of the compounds of the present invention includes those described in Prog. Med. 5:2157-2161 (1985); and those described in "Development of Medicines", Vol. 7, Molecule Planning, pp. 163-198, Hirokawa Publishing, 1990.

(Production Method)

Typical production methods for the compounds of the present invention are described below.

[Chem. 8]

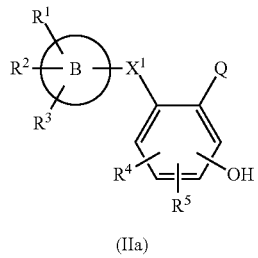

(IIa)

-continued

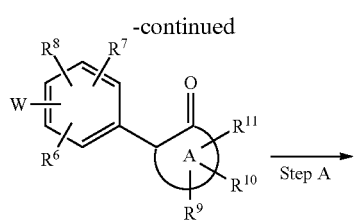
(III)

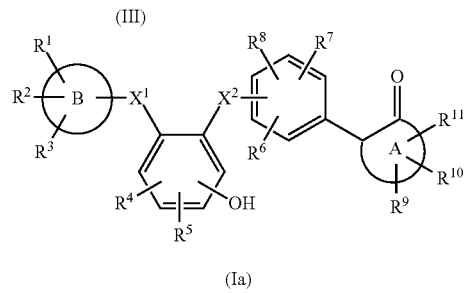
(Ia)

(In the formula, ring A, ring B, $X^1$, $X^2$, $R^1$ to $R^{11}$ have the same meanings as above; Q and W are such that, when Q is —$NH_2$ or —NH-lower alkyl, then W is —COOH, and when Q is —COOH, then W is —$NH_2$ or —NH-lower alkyl.)

Step A:

This is a reaction of producing a compound (Ia) through condensation of a carboxylic acid and an amine of a compound (IIa) and a compound (III). This reaction is attained preferably in the presence of a condensing reagent according to ordinary acylation to form an amide bond. As the condensing reagent, for example, preferred are N,N-dicyclohexylcarbodiimide (DCC), 1-ethyl-3-[3-(N,N-dimethylamino)propyl]carbodiimide, carbonyldiimidazole, diphenylphosphorylazide (DPPA), diethylphosphorylcyanide.

After the carboxylic acid is converted into the corresponding active derivative thereof, it may be condensed with an amine. The active derivative of the carboxylic acid includes active esters obtained through reaction with a phenolic compound such as p-nitrophenol, or an N-hydroxyamine compound such as 1-hydroxysuccinimide or 1-hydroxybenzotriazole; carbonic monoalkyl esters; mixed acid anhydrides obtained through reaction with an organic acid; phosphoric acid-type mixed acid anhydrides obtained through reaction with diphenylphosphoryl chloride and N-methylmorpholine; acid azides obtained through reaction of ester with hydrazine or alkyl nitrite; acid halides such as acid chlorides, acid bromides; and symmetric acid anhydrides. In general, the reaction may be effected in a solvent with cooling or at room temperature; but depending on the type of the acylation, it must be attained in the absence of water in some cases.

The solvent is one not participating in the reaction, including, for example, dimethylformamide, dioxane, tetrahydrofuran, ether, dichloroethane, dichloromethane, chloroform, carbon tetrachloride, dimethoxymethane, dimethoxyethane, ethyl acetate, benzene, acetonitrile, dimethylsulfoxide, ethanol, methanol, water, and their mixed solvents. It may be suitably selected depending on the method to which it is applied.

Depending on the method to be employed, the reaction may smoothly go on in the presence of a base such as N-methylmorpholine, triethylamine, trimethylamine, pyridine, sodium hydride, potassium t-butoxide, butyllithium, sodium amide, potassium carbonate, sodium carbonate, sodium hydrogencarbonate, cesium carbonate, or using the base as a solvent.

Apart from the reaction described herein, any other reaction capable of forming an amide bond may be employed.

The production route for the compound of formula (Ia) may be changed in such a manner that, after the amide bond of $X^2$ is formed, the amide bond of $X^1$ is formed. In addition, any other known alkylation, acylation, oxidation, reduction, hydrolysis or the like capable of being generally employed by those skilled in the art may be combined in any desired manner to produce the compounds of the present invention.

[Chem. 9]

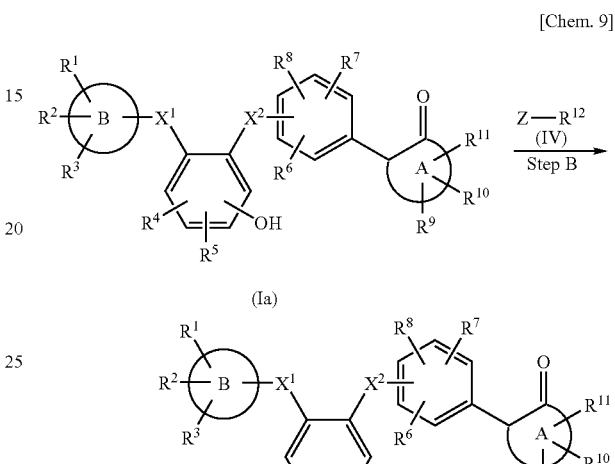

(In the formula, ring A, ring B, $X^1$, $X^2$, $R^1$ to $R^{11}$ have the same meanings as above; Z means a leaving group; $R^{12}$ means an optionally-protected sugar residue.)

Step B:

This is for producing a compound (Ib) having an optionally-protected sugar residue, by reacting a phenol and a sugar donor, compound (Ia) and compound (IV), preferably in the presence of an activator. This reaction may be attained according to ordinary glycosylation. Typical methods are described in the Yuki Gousei Kagaku Kyoukai shi, Vol. 50, No. 5 (1992), pp. 378-390; and "Jikken Kagaku Kouza", Vol. 26, Yuki Gousei VIII, pp. 267-354, 1992, Maruzen.

The sugar donor includes, for example, sugar derivatives having a leaving group at the 1-position of sugar. The leaving group includes halogen, thioalkyl, thioheteroaryl, acyloxy, trichloroacetimidate, diarylphosphate, diarylphosphinimidate, tetramethylphosphoramidate, dialkylphosphite.

The condensing reagent includes silver carbonate, silver trifluoromethanesulfonate, silver perchlorate, silver oxide, sodium hydroxide, potassium carbonate, sodium methoxide, sodium hydride, diazabicycloundecene, trimethylsilyl trifurate, boron trifluoride, methyl trifurate, silicon tetrachloride, tin chloride, paratoluenesulfonic acid and salts thereof, trifluoromethanesulfonic acid anhydride, copper bromide, mercury bromide, N-bromosuccinimide.

Triphenylphosphine, diethylazodicarboxylate or the like may be used as an activator, for example, for a sugar donor having a 1-positioned hydroxyl group.

In general, the reaction may be effected in a solvent with cooling or at room temperature; but depending on the type of the glycosylation, it must be attained in the absence of water in some cases.

The solvent is an inert solvent not participating in the reaction, including, for example, dimethylformamide, dioxane, tetrahydrofuran, ether, dichloroethane, dichloromethane, chloroform, carbon tetrachloride, dimethoxymethane, dimethoxyethane, ethyl acetate, benzene, toluene, acetonitrile, dimethylsulfoxide, methanol, ethanol, and their mixed solvents. It may be suitably selected depending on the method to which it is applied.

Apart from the reaction described herein, any other reaction for forming a glycoside bond may also be employed.

In case where $R^{12}$ in the compound (Ib) of the present invention is an optionally-protected sugar residue and when the protective group is not cleaved in the step B, the protective group may be cleaved according to a method suitable for cleavage of the protective group, for example, through hydrolysis with a base such as sodium carbonate or through reduction such as catalytic hydrogenation, thereby giving compounds of the present invention where $R^{12}$ is a non-protected sugar residue.

Not specifically defined, the protective group may be any ordinary one used for protection of a hydroxyl group or a carboxyl group, and includes, for example, optionally-substituted lower alkyl, aralkyl, tri-lower alkylsilyl, acyl. "Aralkyl" means a group derived from the above-mentioned alkyl group by substituting the hydrogen atom with aryl, concretely including benzyl. "Acyl" concretely includes acetyl, propionyl, isopropionyl, benzoyl.

(Production Method for Starting Compound)

Typical production methods for starting compounds for the compounds (I) of the present invention are described below.

The leaving group for Y or V includes halogen, methanesulfonyloxy, p-toluenesulfonyloxy, trifluoromethanesulfonyloxy groups.

The palladium catalyst for use herein is preferably tetrakistriphenylphosphine palladium, dichlorobistriphenylphosphine palladium, dichlorodiphenylferrocenyl palladium. The base is preferably sodium carbonate, potassium carbonate, sodium hydroxide, potassium hydroxide, sodium ethoxide, sodium methoxide, potassium fluoride, cesium fluoride.

Not specifically defined, the solvent includes, for example, aromatic hydrocarbons such as benzene, toluene, xylene; ethers such as diethyl ether, tetrahydrofuran (THF), 1,4-dioxane, 1,2-dimethoxyethane, 1,2-diethoxyethane; halogenohydrocarbons such as dichloromethane, 1,2-dichloroethane, chloroform; alcohols such as methanol, ethanol, 2-propanol, butanol; N,N-dimethylformamide (DMF), N-methylpyrrolidone (NMP), dimethylsulfoxide (DMSO), water, or their mixed solvents.

In case where U in the compound (IIIa) means $NO_2$, then a compound where U is —$NH_2$ may be obtained through reduction; and in case where U means —$COOP^1$, —NH—$P^2$ or —N($P^2$)-lower alkyl, then compounds where U is —COOH, —$NH_2$ or —NH-lower alkyl may be obtained according to a method suitable for cleavage of the protective group, for example, by cleavage through hydrolysis with a base such as sodium hydroxide or an acid such as hydrochloric acid, or by cleavage through reduction such as catalytic hydrogenation, or by cleavage with an acid such as trifluoroacetic acid.

Also employable for the production is a method comprising a combination of ordinary steps known to those skilled in the art, for example, a method comprising preparing a precursor of the compound (IIIa) where U is —CN or any others readily convertible into the compound (IIIa), followed by converting the precursor into the compound (IIIa) according to a method suitable to the precursor.

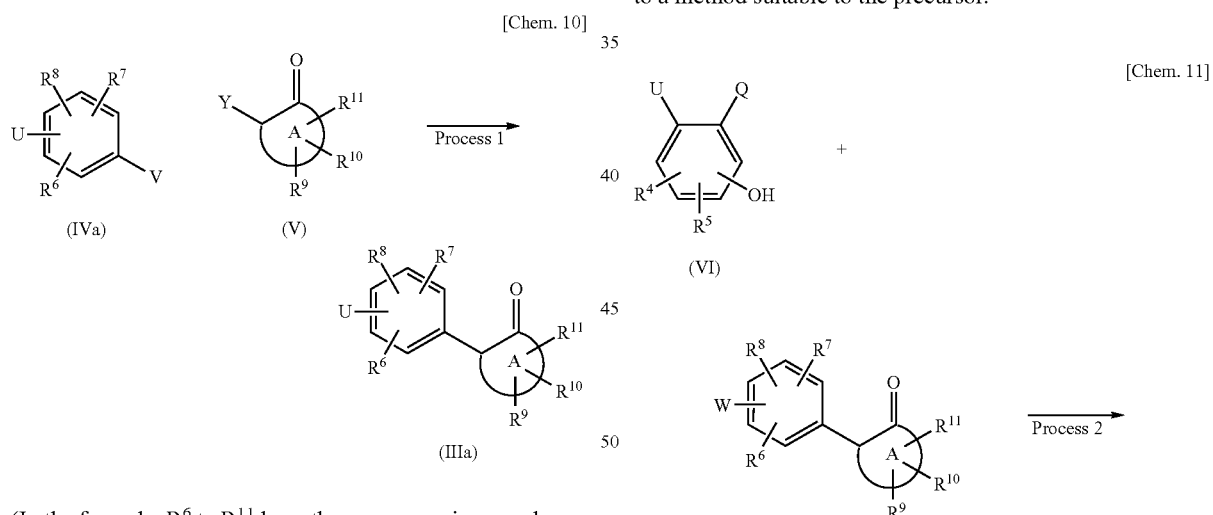

(In the formula, $R^6$ to $R^{11}$ have the same meanings as above; U means —COOH, —$COOP^1$, —$NH_2$, —NH-lower alkyl, —NH—$P^2$, —N($P^2$)-lower alkyl, $NO_2$; $P^1$ and $P^2$ each mean a carboxyl-protective group or a amine-protective group. When V means —$B(OH)_2$ or —$B(OL^1)OL^2$, then Y means a leaving group; and when V means a leaving group, then Y means —$B(OH)_2$ or —$B(OL^1)OL^2$. $L^1$ and $L^2$ are the same or different, each representing lower alkyl, or $L^1$ and $L^2$, taken together, form optionally-substituted lower alkylene.)

Production Method 1:

This is a reaction for obtaining a compound (IIIa) through condensation of a compound (IVa) and a compound (V). This reaction is attained in a solvent inert to the reaction, in the presence of a base and a palladium catalyst, with cooling or under heating.

(In the formula, $R^4$ to $R^{11}$, U, Q and W have the same meanings as above.)

Production Method 2:

This is a reaction for obtaining a compound (VII) through condensation of a compound (VI) and a compound (III). The reaction of this step may be the same as that of the step A.

The compounds of the present invention thus produced in the manner as above may be isolated and purified in known methods of, for example, extraction, precipitation, partitioning chromatography, fractionating crystallization, recrystallization, etc. Free compounds of the present invention may be converted into desired salts through ordinary salt formation.

In case where the compounds of the present invention have an asymmetric carbon, they may include optical isomers. The optical isomers may be resolved in an ordinary manner of fractionating crystallization for recrystallization with a suitable salt, or column chromatography.

Effect of the Invention

The compounds of the present invention specifically inhibit the activated blood coagulation factor X, and have a strong anticoagulation activity. Accordingly, the compounds are useful as anticoagulants or as agents for preventing and treating disorders to be induced by thrombi or emboli.

The diseases for which the compounds of the present invention are effective include those in cerebrovascular disorders such as cerebral infarction, cerebral thrombosis, cerebral embolism, transient cerebral ischemia (TIA), subarachnoid hemorrhage (vasospasm); those in ischemic cardiopathy such as acute and chronic myocardial infarction, unstable angina, coronary thrombolysis; those in pulmonary vascular disorders such as pulmonary infarction, pulmonary embolism; and those in other various vascular disorders such as peripheralarterio-occlusion, deep vein thrombosis, disseminated intravascular coagulation syndrome, thrombophilia after artificial vasoformation and after artificial valvoplasty, re-occlusion and re-constriction after coronary bypass operation, re-occlusion and re-constriction after PTCA (percutaneous transluminal coronary angioplasty) or PTCR (percutaneous transluminal coronary recanalization), thrombophilia during extracorporeal circulation.

Based on their activity to inhibit the activated blood coagulation factor X and their activity to inhibit the growth of influenza viruses, the compounds of the present invention are expected to be usable for preventing infection with influenza viruses and for curing influenza (JP-A-6-22971).

The excellent activity of the compounds of the present invention to inhibit the activated blood coagulation factor X was confirmed by the test methods shown below.

1) Test of Measuring Blood Coagulation Time with Human Activated Blood Coagulation Factor X (Human Factor Xa):

10 μl of a test compound dissolved in DMSO or DMSO alone, and 50 μl of human factor Xa (Enzyme Research Labs) were added to 90 μl of human plasma, and incubated at 37° C. for 3 minutes, and then 100 μl of 20 mM $CaCl_2$ previously warmed at 37° C. was added to it, and the time taken before coagulation was measured with a c coagulometer (Amelung's KC10). The human plasma was prepared as follows: Using sodium citrate as an anticoagulant, blood was collected from a healthy subject, centrifuged at 3000 rpm for 15 minutes at 4° C., the resulting plasma was pooled, frozen and stored. The concentration of the human factor Xa was so determined that the coagulation time with DMSO (control) added thereto could be around 30 seconds. The $CT_2$ value (the concentration for 2-fold prolongation of the coagulation time with DMSO) was calculated through linear regression, by plotting the relative value (fold) of the coagulation time to the control and the test compound concentration.

2) Test of Measuring Enzyme Inhibition by Synthetic Substrate Method:

25 μl of a reaction buffer (pH 8.4), 5 μl of a test compound dissolved in DMSO or DMSO alone, and 10 μl of a synthetic substrate, 2 mM S-2222 (Chromogenix) were added to a 96-well microplate, then 10 μl of 0.025 U/ml human factor Xa was added thereto, and reacted at 37° C. for 10 minutes, and then the absorbance change at 405 nm was measured with Molecular Devices' Spectramax $340PC^{384}$, and the $IC_{50}$ value was calculated.

As a result of this test, the $IC_{50}$ value of the compound of Example 1 was 6.7 nM, and that of the compound of Example 30 was 8.3 nM.

3) Extrinsic Coagulation Time (PT):

2 μl of a test compound dissolved in DMSO or DMSO alone, and 50 μl of physiological saline were added to 50 μl of human plasma warmed at 37° C. for 1 minute, then 100 μl of HemosIL RecombiPlasTin (Instrumentation Laboratory) was added, and the coagulation time was measured. For measuring the coagulation time, used was Amelung's KC10A. The $CT_2$ value (the concentration for 2-fold prolongation of the coagulation time with DMSO) was calculated through linear regression, by plotting the relative value (fold) of the coagulation time to the control and the test compound concentration.

As a result of this test, the $CT_2$ value of the compound of Example 1 was 0.34 μM, and that of the compound of Example 42 was 0.65 μM.

The results of the above measurements 1), 2) and 3) have confirmed that the compounds of the present invention inhibit the human activated blood coagulation factor X and exhibit a strong anticoagulant effect.

4) Test of Measuring Ex Vivo Coagulation Time with Mice (Oral Administration):

To test animals of male ICR mice (body weight, about 40 g, SLC) that had been fasted for 12 hours or longer, a solution or suspension of a test compound dissolved in 0.5% methyl cellulose was forcedly orally administered (100 mg/kg), using a feeding needle; and after 30 minutes and after 2 hours, under anesthesia with diethyl ether, 1 ml of blood was collected from the mice through their postcaval vein in 3.8% sodium citrate to be ⅒ by volume, and centrifuged at 12000 rpm for 3 minutes to separate plasma therefrom. The extrinsic coagulation time (PT) and the intrinsic coagulation time (APTT) for this plasma were measured according to the following methods a) and b).

a) Extrinsic Coagulation Time (PT):

50 μl of the mouse plasma was warmed at 37° C. for 1 minute, and 100 μl of HemosIL RecombiPlasTin was added, and the coagulation time was counted. For measuring the coagulation time, used was Amelung's KC10A. The mouse plasma coagulation time with no test compound administration was control; and the coagulation time prolonging activity of the test compound was represented by a relative value to the control, 1.

As a result, in 30 minutes after their administration, the compounds of Example 10 and Example 78 had a coagulation time prolonging activity of 3.3 times and 3.9 times, respectively; or that is, the compounds exhibited an extremely strong coagulation time prolonging activity.

b) Intrinsic Coagulation Time (APTT)

50 μl of Hemoliance Synthasil APTT (Instrumentation Laboratory) was added to 50 μl of the above plasma, warmed at 37° C. for 3 minutes, and then 50 μl of 20 mM $CaCl_2$ solution previously kept warmed at 37° C. was added to it, and the coagulation time was counted. For measuring the coagulation time, used was Amelung's KC10A. The mouse plasma coagulation time with no test compound administration was control; and the activity of the test compound was represented by a relative value to the control, 1.

The dose dependency and the time-dependent change of the anticoagulation effect were investigated in the same manner as above but changing the dose and the time for blood collection.

5) Method of Measuring Ex Vivo Coagulation Time with Cynomolgus Monkeys (Oral Administration):

To test animals of male cynomolgus monkeys (body weight, about 4 kg) that had been fasted for 12 hours or longer, a solution (suspension) of a test compound dissolved in 0.5% methyl cellulose was orally administered in a forced manner using a feeding needle. Before administration of the test compound and in 1, 2, 4, 8 and 24 hours after the administration thereof, 1 ml of blood was collected from the thus-treated animals through their femoral vein in 3.8% sodium citrate to be 1/10 by volume, and centrifuged at 12000 rpm for 3 minutes to separate the plasma. The extrinsic coagulation time (PT) and the intrinsic coagulation time (APTT) for this plasma were measured according to the same methods as in a) and b).

The test was not under anesthesia.

The test results of the above 4) and 5) confirm the coagulation time prolongation effect of the compounds of the present invention in oral administration.

Pharmaceutical compositions comprising, as an active ingredient, one or more of the compounds of formula (I) and their pharmaceutically acceptable salts of the present invention can be formulated along with ordinary pharmaceutical carriers, vehicles and other additives into tablets, powders, fine granules, granules, capsules, pills, liquid preparations, injections, suppositories, ointments, cataplasms, and the like, and are administered orally or parenterally.

The clinical dose to human of the compounds of the present invention may be suitably determined, depending on the conditions, the body weight, the age and the sex of the patients to which they are administered, but is, in general, from 0.1 to 500 mg/adult/day for oral administration, and from 0.01 to 100 mg/adult/day for parenteral administration. This may be administered to the patients all at a time, or may be divided into a few portions for administration in different times. Since the dose may vary depending on various conditions, a smaller dose than the defined range may well be employed, as the case may be.

As the solid composition for oral administration of the present invention, employed are tablets, powders, granules, etc. The solid composition of those types comprises one or more active substances along with at least one inert diluent, such as lactose, mannitol, glucose, hydroxypropyl cellulose, microcrystalline cellulose, starch, polyvinyl pyrrolidone, meta-silicic acid, and magnesium aluminate. In an ordinary manner, the composition may contain any other additives except the inert diluents noted above, for example, a lubricant such as magnesium stearate, a disintegrator such as calcium cellulose glycolate, a stabilizer such as lactose, and a solubilizer or dissolution promoter such as glutamic acid or aspartic acid. If desired, the tablets and pills may be coated with a film of gastric or enteric substances such as sucrose, gelatin, hydroxypropyl cellulose, hydroxypropylmethyl cellulose phthalate, etc.

The liquid composition for oral administration includes, for example, pharmaceutically acceptable emulsions, solutions, suspensions, syrups, elixirs and the like, which contain ordinary inactive diluents such as purified water and ethyl alcohol. In addition to the inert diluents, those compositions may further contain pharmaceutical aids such as solubilizers, dissolution promoters, wetting promoters, suspension promoters, and also sweeteners, flavorings, aromas, and preservatives.

The injection for parenteral administration includes, for example, germ-free, aqueous or non-aqueous solutions, suspensions and emulsions. The diluent for the aqueous solutions and suspensions includes, for example, distilled water and physiological saline for injections. The diluent for the non-aqueous solutions and suspensions includes, for example, propylene glycol, polyethylene glycol, vegetable oils such as olive oil, alcohols such as ethyl alcohol, Polysolvate 80 (trade name), etc.

Those compositions may further contain additives such as isotonicating promoters, preservatives, wetting promoters, emulsifiers, dispersants, stabilizers (e.g., lactose), solubilizers, dissolution promoters, etc. These are sterilized by filtering them through bacteria-trapping filters, or by adding microbicides thereto, or by exposing them to radiations. The germ-free, solid compositions thus produced may be dissolved in germ-free water or in germ-free solvents for injection, before using them.

Where the compounds of the present invention have low solubility, they may be processed for solubilization. For the solubilization treatment, employable are any known methods applicable to pharmaceutical preparations. For example, employed are a method of adding surfactants (e.g., polyoxyethylene-hardened castor oils, polyoxyethylene-sorbitan higher fatty acid esters, polyoxyethylene-polyoxypropylene glycols, sucrose fatty acids) to the compounds; and a method of forming solid dispersions comprising the compounds and solubilizers, for example, polymers (water-soluble polymers such as hydroxypropylmethyl cellulose (HPMC), polyvinylpyrrolidone (PVP), polyethylene glycol (PEG); enteric polymers such as carboxymethylethyl cellulose (CMEC), hydroxypropylmethyl cellulose phthalate (HPMCP), methyl methacrylate-methacrylic acid copolymer (Eudragit L, S, trade name by Rohm and Haas)). If desired, further employed are a method of forming soluble salts, and a method of forming clathrate compounds with cyclodextrin or the like. The solubilizing means may be suitably modified depending on the chemicals to be processed therewith ("Recent Pharmaceutical Techniques and Their Applications", Isamu Utsumi, et al., in the Journal of Medicines, 157-159, 1983; and "Pharmacological Monograph No. 1, Bioavailability" by Koji Nagai, et al., published by Soft Science Co., 78-82, 1988). Of those, preferred is the method of forming solid dispersions of chemicals and solubilizers to improve the solubility of the chemicals (JP-A 56-49314; FR 2,460,667).

BEST MODE FOR CARRYING OUT THE INVENTION

Examples

Now, the method for producing the compounds of the present invention is described concretely hereunder, with reference to the following Examples of demonstrating the production of the compounds. Some starting compounds for the compounds of the present invention are novel, and the method for producing them is demonstrated in Reference Examples.

Reference Example 1

3-Bromo-1-methylpyridin-4(1H)-one hydrobromide (640 mg) was suspended in toluene (10 ml) and water (5 ml), and

[4-(methoxycarbonyl)phenyl]boronic acid (642 mg), sodium carbonate (757 mg) and tetrakis(triphenylphosphine)palladium(0) (138 mg) were added, followed by stirring under heating in an oil bath at 100° C. for 3 hours. The reaction mixture was filtered through Celite, followed by extraction with ethyl acetate. The organic layer was concentrated under reduced pressure, and the residue was purified by silica gel column chromatography (FUJI SILYSIA CHEMICAL Ltd., the same shall apply hereinunder) (chloroform:methanol=90:10) to obtain methyl 4-(1-methyl-4-oxo-1,4-dihydropyridin-3-yl)benzoate (118 mg).

In the same manner as in Reference Example 1, compounds of Reference Examples 4, 7, 10, 12, 14, 16, 18, 119, 132 were obtained.

Reference Example 2

1 M NaOH (1.42 ml) was added to an EtOH suspension (3 ml) of methyl 4-(1-methyl-4-oxo-1,4-dihydropyridin-3-yl)benzoate (115 mg), followed by stirring at room temperature for 8 hours. 1 M HCl (1.42 ml) was added to the reaction solution, followed by concentration under reduced pressure. Water (20 ml) was added to the residue, followed by stirring for 20 minutes. The precipitate formed was collected by filtration and dried under reduced pressure at 60° C. to obtain 4-(1-methyl-4-oxo-1,4-dihydropyridin-3-yl)benzoic acid (92 mg).

In the same manner as in Reference Example 2, compounds of Reference Examples of 5, 9, 17, 22, 24, 31, 33, 34, 36, 38, 40, 42, 44, 46, 48, 50, 52, 54, 56, 58, 60, 62, 64, 66, 68, 70, 72, 74, 76, 78, 80, 82, 84, 85, 87, 89, 91, 93, 95, 97, 99, 101, 103, 105, 107, 109, 111, 113, 115, 117, 120, 123, 125, 127, 129, 133 were obtained.

Reference Example 3

5-Bromopyrimidin-4(3H)-one (578 mg) was dissolved in N,N-dimethylformamide (15 mL), and potassium carbonate (685 mg) and methyl iodide (247 μL) were added, followed by stirring at room temperature for 24 hours. Water was added to the reaction mixture, followed by extraction with chloroform. The organic layer was washed with saturated brine and dried over anhydrous sodium sulfate. The solvent was evaporated under reduced pressure, and the resulting residue was purified by silica gel column chromatography (hexane:ethyl acetate=1:1) to obtain 5-bromo-3-methylpyrimidin-4(3H)-one (337 mg) as a white solid.

Reference Example 6

5-Bromopyrimidin-4(3H)-one (459 mg) was dissolved in N,N-dimethylformamide (13 mL), then with cooling with ice, sodium hydride (55%, 137 mg) was added, followed by stirring at the same temperature for 30 minutes. Then, 1-(chloromethyl)-4-methoxybenzene (392 μL) was added, followed by stirring at room temperature for 15 hours. Water was added to the reaction mixture, followed by extraction with chloroform. The organic layer was washed with saturated brine and dried over anhydrous sodium sulfate. The solvent was evaporated under reduced pressure, and the resulting residue was purified by silica gel column chromatography (hexane:ethyl acetate=4:1 to 2:1) to obtain 5-bromo-3-(4-methoxybenzyl)pyrimidin-4(3H)-one (382 mg) as a white solid.

Reference Example 8

Methyl 4-[1-(4-methoxybenzyl)-6-oxo-1,6-dihydropyrimidin-5-yl]benzoate (205 mg) was dissolved in trifluoroacetic acid (5 mL), followed by stirring at 70° C. for 15 hours. The reaction mixture was evaporated under reduced pressure, followed by two times azeotropy with toluene. Water was added to the resulting residue, followed by three times extraction with chloroform. The organic layer was dried over anhydrous sodium sulfate, then the solvent was evaporated, and the resulting residue was purified by silica gel column chromatography (methanol/chloroform=2% to 5%) to obtain methyl 4-(6-oxo-1,6-dihydropyrimidin-5-yl)benzoate (86 mg) as a white solid.

Reference Example 11

An aqueous 6 N hydrochloric acid solution (5 mL) was added to methyl 4-(2-oxo-2H-pyran-3-yl)benzoate (72 mg), followed by stirring at 90° C. for 15 hours. The reaction mixture was cooled to room temperature, water was added, and the solid was collected by filtration. After washing with water, this solid was dried under reduced pressure to obtain 4-(2-oxo-2H-pyran-3-yl)benzoic acid (65 mg) as a pale brown solid.

In the same manner as in Reference Example 11, compounds of Reference Examples 13 and 15 were obtained.

Reference Example 19

Acetic acid (10 mL) and aqueous 30% hydrogen peroxide (452 μL) were added to methyl 4-pyridin-3-ylbenzoate (708 mg), followed by stirring at 70° C. for 18 hours. The reaction mixture was concentrated under reduced pressure, an aqueous saturated sodium hydrogencarbonate solution was added, followed by extraction with chloroform. The organic layer was dried over anhydrous sodium sulfate, the solvent was evaporated under reduced pressure, and the resulting residue was purified by silica gel column chromatography (methanol/chloroform=0% to 10%) to obtain methyl 4-(1-oxidopyridin-3-yl)benzoate (720 mg) as a white solid.

Reference Example 20

Acetic anhydride (20 mL) was added to methyl 4-(1-oxidopyridin-3-yl)benzoate (704 mg), followed by stirring at 130° C. for 24 hours. The reaction mixture was concentrated under reduced pressure, followed by two times azeotropy with toluene. The resulting residue was purified by NH-silica gel column chromatography (methanol/chloroform=0% to 10%) to obtain methyl 4-(2-oxo-1,2-dihydropyridin-3-yl)benzoate (651 mg) as a pale brown solid.

In the same manner as in Reference Example 20, a compound of Reference Example 25 was obtained.

Reference Example 21

Methyl 4-(2-oxo-1,2-dihydropyridin-3-yl)benzoate (1.04 g) was dissolved in N,N-dimethylformamide (20 mL), and sodium carbonate (1.88 g) and (2-chloroethyl)dimethylamine hydrochloride (981 mg) were added, followed by stirring at 80° C. for 7 hours. Then, potassium carbonate (628 mg) was added, followed by stirring for 2 hours. The reaction mixture was concentrated under reduced pressure, water was added to the residue, followed by extraction with chloroform. The organic layer was washed with saturated brine, dried over anhydrous sodium sulfate, and the solvent was evaporated under reduced pressure. The resulting residue was purified by NH-silica gel column chromatography (hexane:ethyl acetate=9:1 to 1:1) to obtain methyl 4-{1-[2-(dimethylamino) ethyl]-2-oxo-1,2-dihydropyridin-3-yl}benzoate (954 mg) as a yellow oil.

In the same manner as in Reference Example 21, compounds of Reference Examples 23, 26, 28, 35, 37, 39, 41, 43, 45, 47, 49, 51, 53, 55, 57, 59, 61, 63, 65, 67, 69, 71, 73, 75, 77, 79, 81, 83, 118, 121, 122, 131 were obtained.

Reference Example 27

10% Pd—C (360 mg) was added to an ethanol (30 ml) solution of ethyl 1-{2-[3-{4-[(benzyloxy)carbonyl]phenyl}-2-oxopyridin-1(2H)-yl]ethyl}piperidin-4-carboxylate (1.647 g), followed by stirring in a hydrogen atmosphere under normal pressure at room temperature for 27 hours. The reaction mixture was filtered through Celite, washed with THF and ethanol, and the filtrate was concentrated under reduced pressure. The resulting residue was purified by silica gel column chromatography (chloroform:methanol=100:0 to 80:20) to obtain 4-(1-{2-[4-(ethoxycarbonyl)piperidin-1-yl] ethyl}-2-oxo-1,2-dihydropyridin-3-yl)benzoic acid (671 mg) as a pale yellow amorphous solid.

Reference Example 29

With cooling with ice, triethylamine (0.66 ml) and methanesulfonyl chloride (0.29 ml) were added to a dichloromethane (15 ml) solution of methyl 4-[1-(2-hydroxyethyl)-2-oxo-1,2-dihydropyridin-3-yl]benzoate (841 mg), followed by stirring with cooling with ice for 1 hour. Water (20 ml) was added to the reaction mixture, followed by extraction with chloroform. The organic layer was dried over anhydrous magnesium sulfate, and the solvent was evaporated under reduced pressure to obtain a yellow oil (1.34 g). The resulting yellow oil (1.34 g) was dissolved in acetonitrile (10 ml) and 2-piperazinone (1.55 g) and N,N-diisopropylethylamine (2.68 ml) were added. The reaction mixture was stirred at 80° C. for 6 hours, then left cooled to room temperature. Water (50 ml) was added to the reaction mixture, followed by extraction with chloroform. The organic layer was dried over anhydrous magnesium sulfate and the solvent was evaporated under reduced pressure. The resulting residue was purified by silica gel column chromatography (chloroform:methanol=100:0 to 95:5) to obtain methyl 4-{2-oxo-1-[2-(3-oxopiperazin-1-yl) ethyl]-1,2-dihydropyridin-3-yl}benzoate (1020 mg) as a colorless amorphous solid.

In the same manner as in Reference Example 29, a compound of Reference Example 86 was obtained.

Reference Example 30

With cooling with ice, sodium hydride (60% oil suspension, 50 mg) was added to an N,N-dimethylformamide (10 ml) solution of methyl 4-{2-oxo-1-[2-(3-oxopiperazin-1-yl) ethyl]-1,2-dihydropyridin-3-yl}benzoate (380 mg), followed by stirring for 5 minutes, and then methyl iodide (70 μl) was added. With cooling with ice, the reaction mixture was stirred for 1.5 hours. Water with ice (20 ml) and aqueous saturated sodium hydrogencarbonate solution (10 ml) were added to the reaction mixture, followed by extraction with chloroform. The organic layer was dried over anhydrous magnesium sulfate, then the solvent was evaporated under reduced pressure. The resulting residue was purified by silica gel column chromatography (chloroform:methanol=100:0 to 95:5) to obtain methyl 4-{1-[2-(4-methyl-3-oxopiperazin-1-yl)ethyl]-2-oxo-1,2-dihydropyridin-3-yl}benzoate (350 mg) as a pale yellow oil.

Reference Example 32

Methyl 4-{1-[2-(dimethylamino)ethyl]-2-oxo-1,2-dihydropyridin-3-yl}benzoate (490 mg) was dissolved in acetic acid (20 mL), and platinum oxide (74 mg) was added, followed by stirring in a hydrogen atmosphere (1 atm.) at room temperature for 15 hours. The vapor in the reactor was purged with argon, then the reaction mixture was filtered through Celite, followed by washing with methanol. The filtrate was concentrated under reduced pressure, followed by two times azeotropy with toluene. An aqueous saturated sodium hydrogencarbonate solution was added to the residue, followed by two times extraction with chloroform. The organic layer was dried over anhydrous sodium sulfate, the solvent was evaporated under reduced pressure, and the resulting residue was purified by NH-silica gel column chromatography (hexane:ethyl acetate=2:1 to 1:2) to obtain methyl 4-{1-[2-(dimethylamino)ethyl]-2-oxopiperidin-3-yl}benzoate (439 mg) as a colorless oil.

In the same manner as in Reference Example 32, compounds of Reference Examples 88, 90, 92, 94, 96, 98, 100, 102, 104, 106, 108, 110, 112, 114, 116, 126, 128 were obtained.

Reference Example 124

Methyl 4-(2-oxo-1,2-dihydropyridin-3-yl)benzoate (316 mg) was suspended in toluene (7 mL), and 1-methyl-4-piperidinol (318 mg) and cyanomethylenetrimethylphosphorane (317 mg) were added thereto, followed by stirring at 100° C. for 1 hour. The reaction mixture was concentrated under reduced pressure, and the residue was purified by silica gel column chromatography (methanol/chloroform=0% to 10%) to obtain methyl 4-[1-(1-methylpiperidin-4-yl)-2-oxo-1,2-dihydropyridin-3-yl]benzoate (85 mg) as a colorless oil.

Reference Example 130

4-{1-[2-(Dimethylamino)ethyl]-2-oxo-1,2-dihydropyridin-3-yl}benzoic acid (1.46 g) was suspended in dichloroethane (15 ml), dimethylformamide (125 μL) was added, and oxalyl chloride (367 μL) was dropwise added dropwisely at room temperature. After stirring at room temperature for 30 minutes, the reaction mixture was evaporated under reduced pressure. A dichloromethane (10 ml)-pyridine (10 ml) solution of 2-amino-3-nitrophenol (499 mg) was added to the resulting residue, followed by stirring overnight at room temperature. The reaction suspension was filtered, and the filtrate was evaporated under reduced pressure. The substance collected by filtration and the filtration residue were dissolved in a mixed solvent of ethanol (14.6 mL)-water (14.6 mL), and an aqueous 1 M hydrochloric acid solution (3.24 mL) and iron (904 mg) were added, followed by heating under reflux for 3 hours. An aqueous saturated sodium hydrogencarbonate solution and chloroform were added to the reaction suspension, followed by vigorous stirring and filtration through Celite. The filtrate was extracted with chloroform, the organic layer was evaporated under reduced pressure, and the residue was purified by NH-silica gel column chromatography (chloroform:methanol=100:0 to 95:5) to obtain N-(2-amino-6-hydroxyphenyl)-4-{1-[2-(dimethylamino)ethyl]-2-oxo-1,2-dihydropyridin-3-yl}benzamide (600 mg) as a brown solid.

In the same manner as in Reference Example 130, a compound of Reference Example 134 was produced.

Example 1

1-(3-Dimethylaminopropyl)-3-ethylcarbodiimide hydrochloride (72 mg), 1-hydroxybenzotriazole (62 mg), triethylamine (64 μl) and 2-amino-N-(5-chloro-2-pyridinyl)-3-hydroxybenzamide (121 mg) were added to an N,N-dimethylformamide solution (3 ml) of 4-(1-methyl-4-oxo-1, 4-dihydropyridin-3-yl)benzoic acid (88 mg), followed by stirring at room temperature for 14 hours. After this, water (30 ml) was added to the reaction solution, and the precipitated insoluble solid was collected by filtration. The resulting solid was dried at 60° C. under reduced pressure, then tetrahydrofuran (5 ml), N,N-dimethylformamide (1 ml) and acetic acid (104 μl) were added to the solid, followed by stirring under heating at 60° C. for 2 days. After this, the reaction solution was concentrated under reduced pressure, an aqueous saturated sodium hydrogencarbonate solution (30 ml) was added to the residue, followed by extraction with ethyl acetate. The organic layer was washed with an aqueous saturated sodium hydrogencarbonate solution and saturated brine, dried with magnesium sulfate, and concentrated under reduced pressure. The residue was purified by NH-silica gel column chromatography (chloroform:methanol=97:3). The purified product was suspended in ethanol, 1 M hydrochloric acid (324 μl) was added, followed by concentration under reduced pressure. The residue was recrystallized from ethanol to obtain N-(5-chloropyridin-2-yl)-3-hydroxy-2-{[4-(1-methyl-4-oxo-1,4-dihydropyridin-3-yl)benzoyl]amino}benzamide hydrochloride (123 mg).

In the same manner as in Example 1, compounds of Examples 2 to 11, 20, 21, 24 to 70, 81 to 110, 113 to 119 were obtained.

Example 12

4-(1-{2-[4-(tert-butoxycarbonyl)piperazin-1-yl]ethyl}-2-oxo-1,2-dihydropyridin-3-yl)benzoic acid (731 mg) was dissolved in N,N-dimethylformamide (15 mL), 1-hydroxybenzotriazole (253 mg), 1-(3-dimethylaminopropyl)-3-ethylcarbodiimide hydrochloride (359 mg) and triethylamine (261 μL) were added, and 2-amino-N-(5-chloro-2-pyridinyl)-3-hydroxybenzamide (412 mg) was added, followed by stirring at room temperature for 7 hours. Water was added to the reaction mixture, and the precipitate formed was collected by filtration and washed with water. The resulting solid was dried under reduced pressure and dissolved in tetrahydrofuran (15 mL), and acetic acid (448 μL) was added, followed by stirring at 60° C. for 5 hours. The reaction mixture was concentrated under reduced pressure, and then azeotroped twice with toluene. The residue was purified by NH-silica gel column chromatography (methanol/chloroform=0% to 5%). The resulting compound was dissolved in ethyl acetate (10 mL), and 4 N hydrochloric acid/ethyl acetate (3.88 mL) was added, followed by stirring at room temperature for 20 hours. The reaction mixture was concentrated under reduced pressure, and aqueous saturated sodium hydrogencarbonate solution was added to the residue, followed by extraction with chloroform. The organic layer was dried over anhydrous sodium sulfate, the solvent was evaporated under reduced pressure, and the residue was purified by NH-silica gel column chromatography (methanol/chloroform=0% to 5%) to obtain N-(5-chloropyridin-2-yl)-3-hydroxy-2-({4-[2-oxo-1-(2-piperazin-1-ylethyl)-1,2-dihydropyridin-3-yl]benzoyl}amino)benzamide (867 mg) as a yellow white solid.

In the same manner as in Example 12, compounds of Examples 13, 71 to 76, 79, 111, 112 were obtained.

Example 14

N-(5-chloropyridin-2-yl)-3-hydroxy-2-({4-[2-oxo-1-(2-piperazin-1-ylethyl)-1,2-dihydropyridin-3-yl] benzoyl}amino)benzamide (393 mg) was dissolved in tetrahydrofuran (10 mL), and an aqueous 37% formalin solution (134 μL) and sodium triacetoxyborohydride (436 mg) were added, followed by stirring at room temperature for 9 hours. An aqueous saturated sodium hydrogencarbonate solution was added to the reaction mixture, followed by extraction with chloroform. The organic layer was dried over anhydrous sodium sulfate, then the solvent was evaporated under reduced pressure, and the residue was purified by NH-silica gel column chromatography (methanol/chloroform=0% to 5%). The resulting compound was dissolved in ethyl acetate, and 4 N hydrochloric acid/ethyl acetate was added, followed by stirring at room temperature for 30 minutes. The precipitate formed was collected by filtration and dried under reduced pressure to obtain N-(5-chloropyridin-2-yl)-3-hydroxy-2-[(4-{1-[2-(4-methylpiperazin-1-yl)ethyl]-2-oxo-1,2-dihydropyridin-3-yl}benzoyl)amino]benzamide dihydrochloride (426 mg) as a yellow white solid.

In the same manner as in Example 14, compounds of Examples 15, 77, 78, 80 were obtained.

Example 16

N-(5-chloropyridin-2-yl)-3-hydroxy-2-({4-[2-oxo-1-(2-piperazin-1-ylethyl)-1,2-dihydropyridin-3-yl] benzoyl}amino)benzamide (128 mg) was dissolved in pyridine (5 mL), and acetic anhydride (21 μL) was added, followed by stirring at room temperature for 1 hour. The reaction mixture was concentrated under reduced pressure, then azeotroped twice with toluene. Water was added to the residue, followed by extraction with chloroform and drying over anhydrous sodium sulfate. The solvent was evaporated under reduced pressure and the residue was purified by NH-silica gel column chromatography (methanol/chloroform=0% to 5%). The resulting compound was dissolved in ethyl acetate and 4 N hydrochloric acid/ethyl acetate was added. The precipitate formed was collected by filtration and dried under reduced pressure to obtain 2-[(4-{1-[2-(4-acetylpiperazin-1-yl)ethyl]-2-oxo-1,2-dihydropyridin-3-yl}benzoyl)amino]-N-(5-chloropyridin-2-yl)-3-hydroxybenzamide hydrochloride (109 mg) as a yellow white solid.

In the same manner as in Example 16, a compound of Example 17 was obtained.

Example 18

N-(5-chloropyridin-2-yl)-3-hydroxy-2-({4-[2-oxo-1-(2-piperazin-1-ylethyl)-1,2-dihydropyridin-3-yl] benzoyl}amino)benzamide (130 mg) was dissolved in pyridine (5 mL), and with cooling with ice, methanesulfonyl chloride (51 μL) was added, followed by stifling at room temperature for 4 hours. The reaction mixture was concentrated under reduced pressure, then azeotroped with toluene. An aqueous saturated sodium hydrogencarbonate solution was added to the residue, followed by extraction with chloroform. The organic layer was dried over anhydrous sodium sulfate, and the solvent was evaporated under reduced pressure. The residue was purified by NH-silica gel column chromatography (methanol/chloroform=0% to 5%), then by silica gel column chromatography (methanol/chloroform=0% to 5%). The resulting compound was dissolved in ethyl acetate, and 4 N hydrochloric acid/ethyl acetate was added, followed by stirring at room temperature for 30 minutes. The precipitate was collected by filtration and dried under reduced pressure to obtain N-(5-chloropyridin-2-yl)-3-hydroxy-2-{[4-(1-{2-[4-(methylsulfonyl)piperazin-1-yl]ethyl}-2-oxo-1,2-dihydropyridin-3-yl)benzoyl]amino}benzamide hydrochloride (47 mg) as a yellow white solid.

In the same manner as in Example 18, a compound of Example 19 was obtained.

Example 22

An aqueous 1 M sodium hydroxide solution (3.0 ml) was added to an ethanol (5 ml)-tetrahydrofuran (5 ml) solution of ethyl 1-{2-[3-(4-{[(2-{[(5-chloropyridin-2-yl)amino]carbonyl}-6-hydroxyphenyl)amino]carbonyl}phenyl)-2-oxopyridin-1(2H)-yl]ethyl}piperidine-4-carboxylate (392 mg), followed by stirring at room temperature for 19 hours. 1 M hydrochloric acid (3.0 ml) and water (50 ml) were added to the reaction mixture, followed by extraction with chloroform-isopropanol. The organic layer was dried over anhydrous magnesium sulfate, and the solvent was evaporated under reduced pressure to obtain 1-{2-[3-(4-{[(2-{[(5-chloropyridin-2-yl)amino]carbonyl}-6-hydroxyphenyl)amino]carbonyl}phenyl)-2-oxopyridin-1(2H)-yl]ethyl}piperidine-4-carboxylic acid (332 mg) as a pale yellow solid.

In the same manner as in Example 22, a compound of Example 23 was obtained.

Examples 120, 121

N-(5-chloropyridin-2-yl)-2-[(4-{1-[2-(dimethylamino) ethyl]-2-oxopiperidin-3-yl}benzoyl)amino]-3-hydroxybenzamide (72.2 g) was optically resolved and purified through an optical resolution column CHIRALPAK AD-H, using an elution solvent of n-hexane:ethanol:2-propanol:diethylamine=20:80:0.1:0.1, thereby obtaining compounds of Examples 120 and 120, in an amount of 30.7 g and 29.8 g, respectively.

Example 122

N-(5-chloropyridin-2-yl)-2-[(4-{1-[2-(dimethylamino) ethyl]-2-oxo-1,2-dihydropyridin-3-yl}benzoyl)amino]-3-hydroxybenzamide (7.0 g) was dissolved in chloroform (70 mL), and with cooling with ice, methanol (70 ml), 1,8-diazabicyclo[5.4.0]-7-undecene (4.90 ml) and methyl 1-bromo-1-deoxy-2,3,4-tri-O-acetyl-α-D-glucopyranosidouronate (10.45 g) were added, followed by stirring at room temperature for 2 hours. Further, 1,8-diazabicyclo[5.4.0]-7-undecene (4.90 ml) and methyl 1-bromo-1-deoxy-2,3,4-tri-O-acetyl-α-D-glucopyranosidouronate (10.45 g) were added, followed by stirring at room temperature for 2 hours. Further, 1,8-diazabicyclo[5.4.0]-7-undecene (5.94 ml) and methyl 1-bromo-1-deoxy-2,3,4-tri-O-acetyl-α-D-glucopyranosidouronate (10.45 g) were added, followed by stirring at room temperature for 2 hours. After this, water was added to the reaction solution, followed by extraction with chloroform. The organic layer was dried over anhydrous sodium sulfate, and the solvent was evaporated under reduced pressure. The resulting residue was dissolved in a mixed solvent of methanol (100 mL) and water (50 mL), and at room temperature, sodium carbonate (4.18 g) was added, followed by stirring at room temperature for 1 hour. The reaction mixture was filtered, and the filtrate was evaporated under reduced pressure.

Ethyl acetate was added to the residue, followed by extraction with water. The aqueous layer was washed with ethyl acetate, then the aqueous layer was evaporated under reduced pressure. The residue was purified by high performance liquid column chromatography (DAISOPAK, SP-120-10-ODS-BP, acetonitrile:water=83:17 to 72:28). Ethanol (20 ml) was added to the resulting pure product (682 mg), followed by stirring overnight at room temperature. The precipitated solid was collected by filtration and dried under reduced pressure to obtain 3-[(5-chloropyridin-2-yl)carbamoyl]-2-[(4-{1-[2-(dimethylamino)ethyl]-2-oxo-1,2-dihydropyridin-3-yl}benzoyl)amino]phenyl β-D-glucopyranosiduronic acid (444 mg) as a white solid.

In the same manner as in Example 122, a compound of Example 123 was obtained, starting from the compound of Example 120, and a compound of Example 124 was obtained, starting from the compound of Example 121.

Example 125

N-(5-chloropyridin-2-yl)-2-[(4-{1-[2-(dimethylamino) ethyl]-2-oxopiperidin-3-yl}benzoyl)amino]-3-hydroxybenzamide (300 mg) was dissolved in dimethylformamide (6 mL), and with cooling with ice, an aqueous 32% peracetic acid solution (135 μL) was added, followed by stirring with cooling with ice for 30 minutes. The reaction solution was put into an aqueous saturated sodium hydrogencarbonate solution (30 ml), followed by extraction with chloroform. The organic layer was dried with sodium sulfate and evaporated under reduced pressure to obtain N-(5-chloropyridin-2-yl)-2-[(4-{1-[2-(dimethylnitroryl)ethyl]-2-oxopiperidin-3-yl}benzoyl)amino]-3-hydroxybenzamide (210 mg). The resulting N-(5-chloropyridin-2-yl)-2-[(4-{1-[2-(dimethylnitroryl)ethyl]-2-oxopiperidin-3-yl}benzoyl)amino]-3-hydroxybenzamide (209 mg) was dissolved in dimethylformamide (3 mL), then at room temperature, water (3 ml), benzoic acid (46 mg) and an aqueous 1 M iron chloride solution (38 μL) were added, followed by stirring at room temperature for 2 hours. An aqueous saturated sodium hydrogencarbonate solution was added to the reaction mixture, followed by extraction with chloroform. The organic layer was evaporated under reduced pressure, and the residue was purified by NH-silica gel column chromatography (chloroform:methanol=100:0 to 95:5). The purified product was dissolved in ethanol, and 4 M hydrochloric acid/ethyl acetate solution (1 mL) was added, followed by evaporation under reduced pressure. Ethyl acetate was added to the residue, followed by stirring at room temperature for 1 hour. The precipitate formed was collected by filtration and dried at 40° C. under reduced pressure to obtain N-(5-chloropyridin-2-yl)-3-hydroxy-2-[(4-{1-[2-(methylamino)ethyl]-2-oxopiperidin-3-yl}benzoyl)amino]benzamide hydrochloride (108 mg) as a white solid.

Example 126

N-(2-amino-6-hydroxyphenyl)-4-{1-[2-(dimethylamino) ethyl]-2-oxo-1,2-dihydropyridin-3-yl}benzamide (276 mg) was dissolved in pyridine (6 mL), and with cooling with ice, 4-chlorobenzoyl chloride (99 μL) was added, followed by stirring overnight at room temperature. The reaction solution was evaporated under reduced pressure, and the residue was purified by silica gel column chromatography (chloroform: methanol:ammonia=100:0:0 to 95:5:0.5). The purified product (250 mg) was dissolved in ethyl acetate, and 4 M hydrochloric acid/ethyl acetate solution (129 μL) was added, followed by stirring at room temperature for 1 hour. The precipitate formed was collected by filtration and dried at room temperature under reduced pressure to obtain 4-chloro-N-{2-[(4-{1-[2-(dimethylamino)ethyl]-2-oxo-1,2-dihydro-pyridin-3-yl}benzoyl)amino]-3-hydroxyphenyl}benzamide hydrochloride (157 mg) as a white solid.

In the same manner as in Example 126, compounds of Examples 127, 128 were obtained.

The structural formulae and the physicochemical properties of the compounds of Reference Examples and those of Examples are shown in Tables 1 to 30 attached hereto. The meanings of the abbreviations in the Tables are shown below. The compounds in Tables 31 to 42 may be readily produced nearly in the same manner as in the above-mentioned Examples or production methods, or by applying some modifications obvious to those skilled in the art to such methods.

Rf: Number of Reference Example, Ex: Number of Example, Structure: Structural Formula, DATA: physical data, NMR: nuclear magnetic resonance spectrum (TMS internal standard), FAB, ESI: mass spectrometry data. In Structure, HCl includes both monohydrochloride and dihydrochloride.

TABLE 1

| Rf | Structure | DATA |
|---|---|---|
| 1 | | ESI+: 244 |
| 2 | | ESI+: 230 |
| 3 | | ESI+: 190 |
| 4 | | FAB+: 245 |
| 5 | 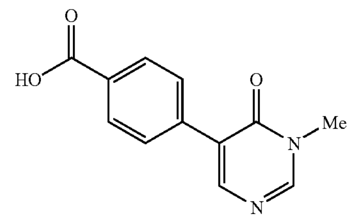 | FAB−: 230 |
| 6 | 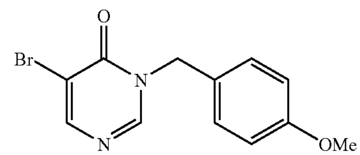 | FAB+: 297 |
| 7 | 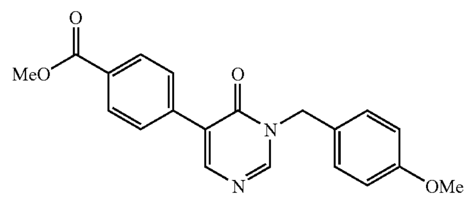 | FAB+: 351 |
| 8 | 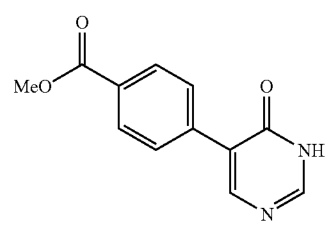 | FAB−: 229 |
| 9 | 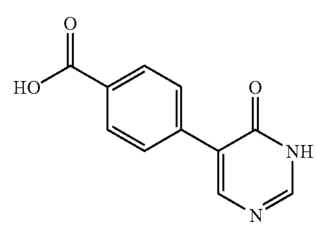 | FAB+: 217 |
| 10 | 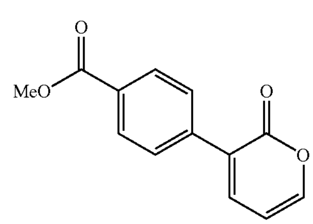 | FAB+: 231 |
| 11 | 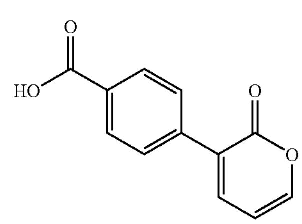 | FAB+: 217 |

TABLE 1-continued

| Rf | Structure | DATA |
|----|-----------|------|
| 12 | methyl 4-(6-oxocyclohex-1-en-1-yl)benzoate | FAB+: 231 |
| 13 | 4-(6-oxocyclohex-1-en-1-yl)benzoic acid | FAB+: 217 |
| 14 | methyl 4-(2-oxo-5,6-dihydro-2H-pyran-3-yl)benzoate | FAB+: 233 |
| 15 | 4-(2-oxo-5,6-dihydro-2H-pyran-3-yl)benzoic acid | FAB+: 219 |
| 16 | methyl 4-(1-methyl-2-oxo-1,2,5,6-tetrahydropyridin-3-yl)benzoate | ESI+: 246 |

TABLE 2

| Rf | Structure | DATA |
|----|-----------|------|
| 17 | 4-(1-methyl-2-oxo-1,2,5,6-tetrahydropyridin-3-yl)benzoic acid | ESI+: 232 |
| 18 | methyl 4-(pyridin-3-yl)benzoate | FAB+: 214 |
| 19 | methyl 4-(1-oxidopyridin-3-yl)benzoate | FAB+: 230 |
| 20 | methyl 4-(2-oxo-1,2-dihydropyridin-3-yl)benzoate | FAB+: 230 |

TABLE 2-continued
| 21 | 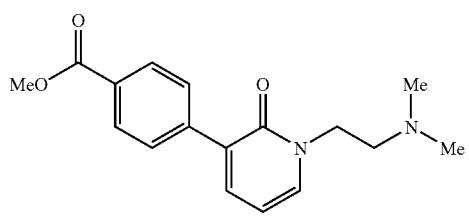 | FAB+: 301 |
| 22 | 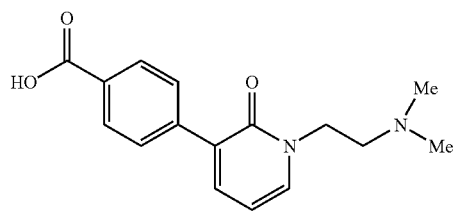 | FAB+: 287 |
| 23 | 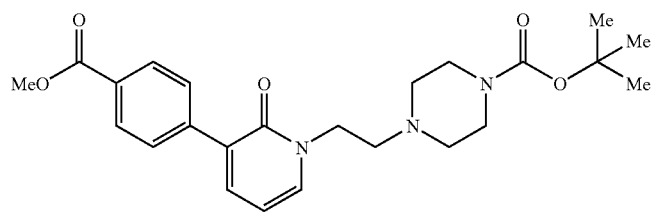 | FAB+: 442 |
| 24 | 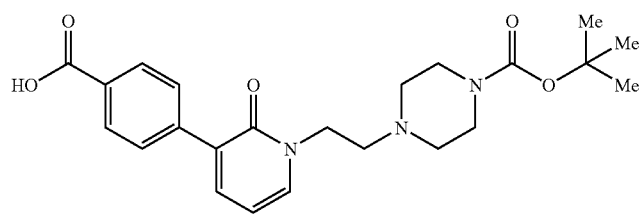 | FAB+: 428 |
| 25 | 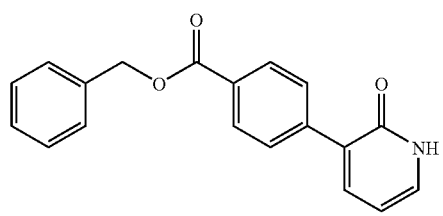 | FAB+: 306 |
| 26 | 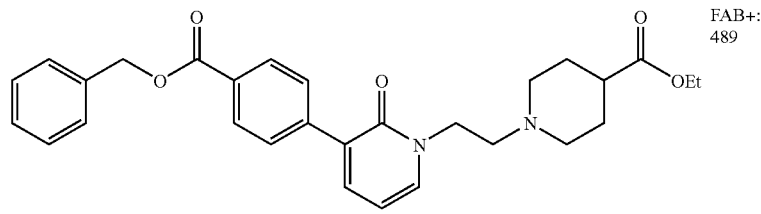 | FAB+: 489 |
| 27 | 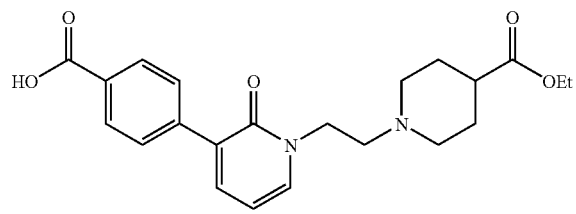 | FAB+: 399 |

TABLE 2-continued
| | | |
|---|---|---|
| 28 | 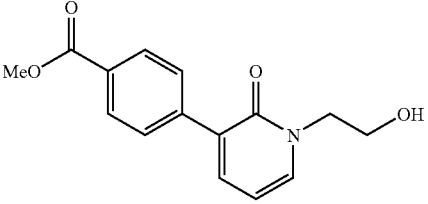 | FAB+: 274 |
| 29 | 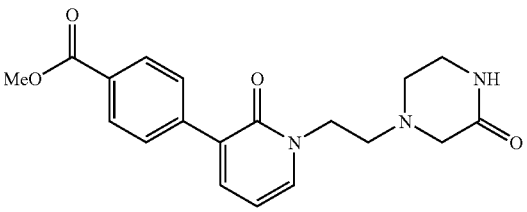 | FAB+: 356 |
| 30 | 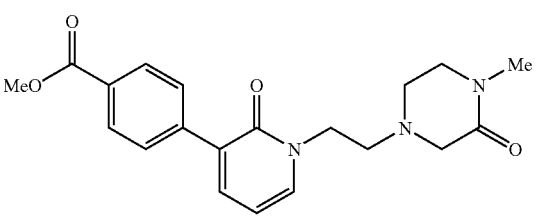 | ESI+: 370 |
| 31 | 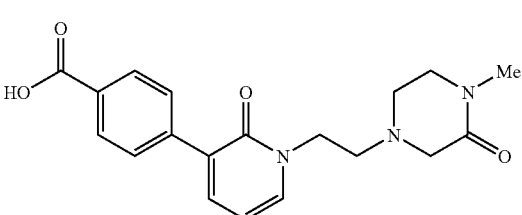 | ESI+: 356 |
| 32 | 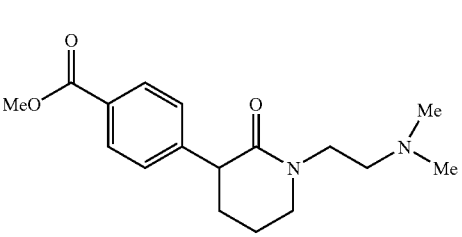 | FAB+: 305 |
| 33 | 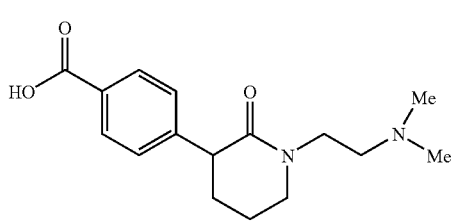 | FAB+: 291 |
| 34 | 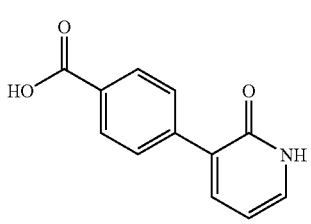 | FAB+: 216 |

TABLE 3
| 35 | 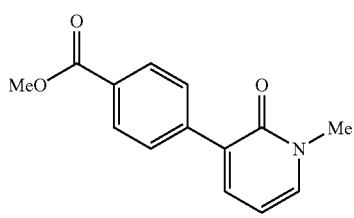 | FAB+: 244 |
| --- | --- | --- |
| 36 | 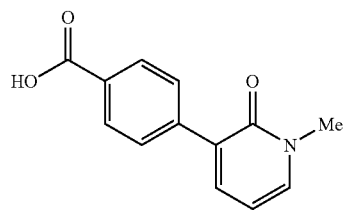 | FAB+: 230 |
| 37 | 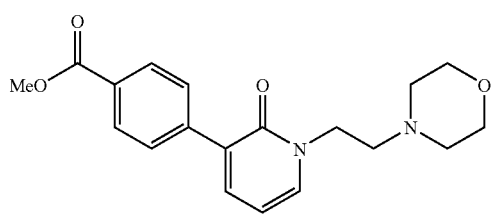 | ESI+: 343 |
| 38 | 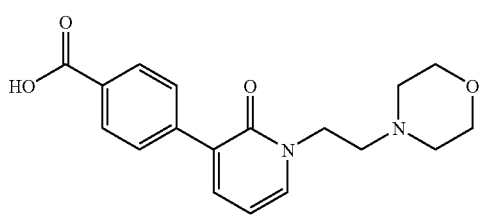 | ESI+: 329 |
| 39 | 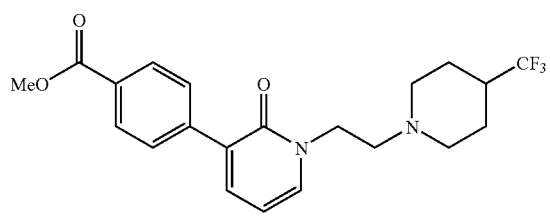 | ESI+: 409 |
| 40 | 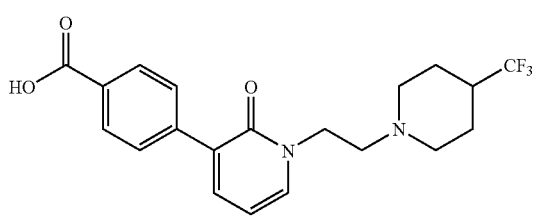 | ESI+: 395 |
| 41 | 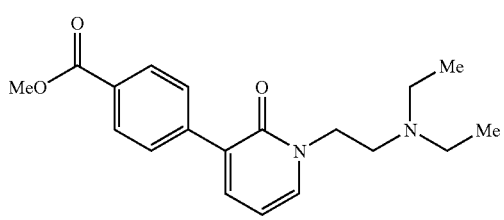 | FAB+: 230 |

TABLE 3-continued
| 42 | 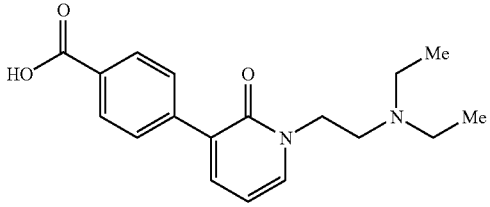 | FAB+: 301 |
| --- | --- | --- |
| 43 | 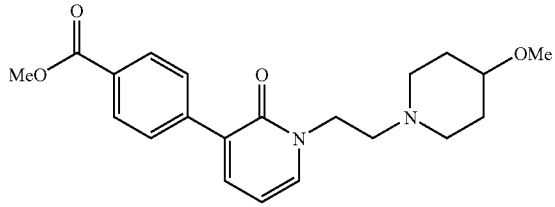 | FAB+: 287 |
| 44 | 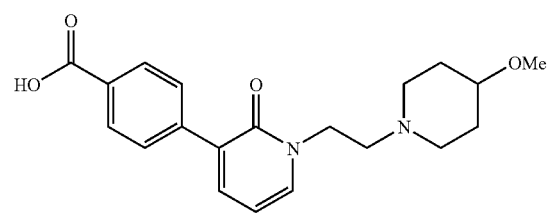 | FAB+: 244 |
| 45 | 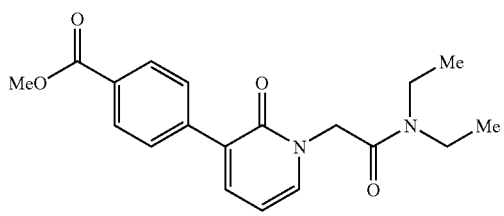 | FAB+: 230 |
| 46 | 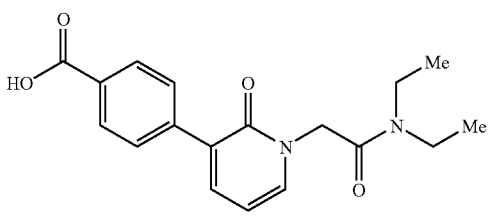 | FAB+: 329 |
| 47 | 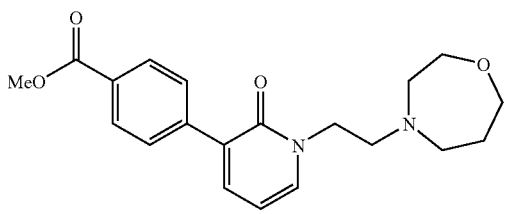 | ESI+: 357 |
| 48 | 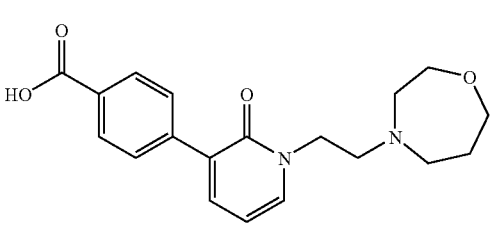 | ESI+: 343 |

TABLE 3-continued

| | Structure | MS |
|---|---|---|
| 49 | Methyl 4-[1-[2-(1,1-dioxo-1,4-thiazinan-4-yl)ethyl]-2-oxo-1,2-dihydropyridin-3-yl]benzoate | ESI+: 391 |
| 50 | 4-[1-[2-(1,1-dioxo-1,4-thiazinan-4-yl)ethyl]-2-oxo-1,2-dihydropyridin-3-yl]benzoic acid | ESI+: 377 |
| 51 | Methyl 4-[1-[3-(diethylamino)propyl]-2-oxo-1,2-dihydropyridin-3-yl]benzoate | ESI+: 343 |
| 52 | 4-[1-[3-(diethylamino)propyl]-2-oxo-1,2-dihydropyridin-3-yl]benzoic acid | ESI+: 329 |
| 53 | Methyl 4-[1-[2-[N-(2-methoxyethyl)-N-methylamino]ethyl]-2-oxo-1,2-dihydropyridin-3-yl]benzoate | ESI+: 345 |
| 54 | 4-[1-[2-[N-(2-methoxyethyl)-N-methylamino]ethyl]-2-oxo-1,2-dihydropyridin-3-yl]benzoic acid | ESI+: 331 |

TABLE 4
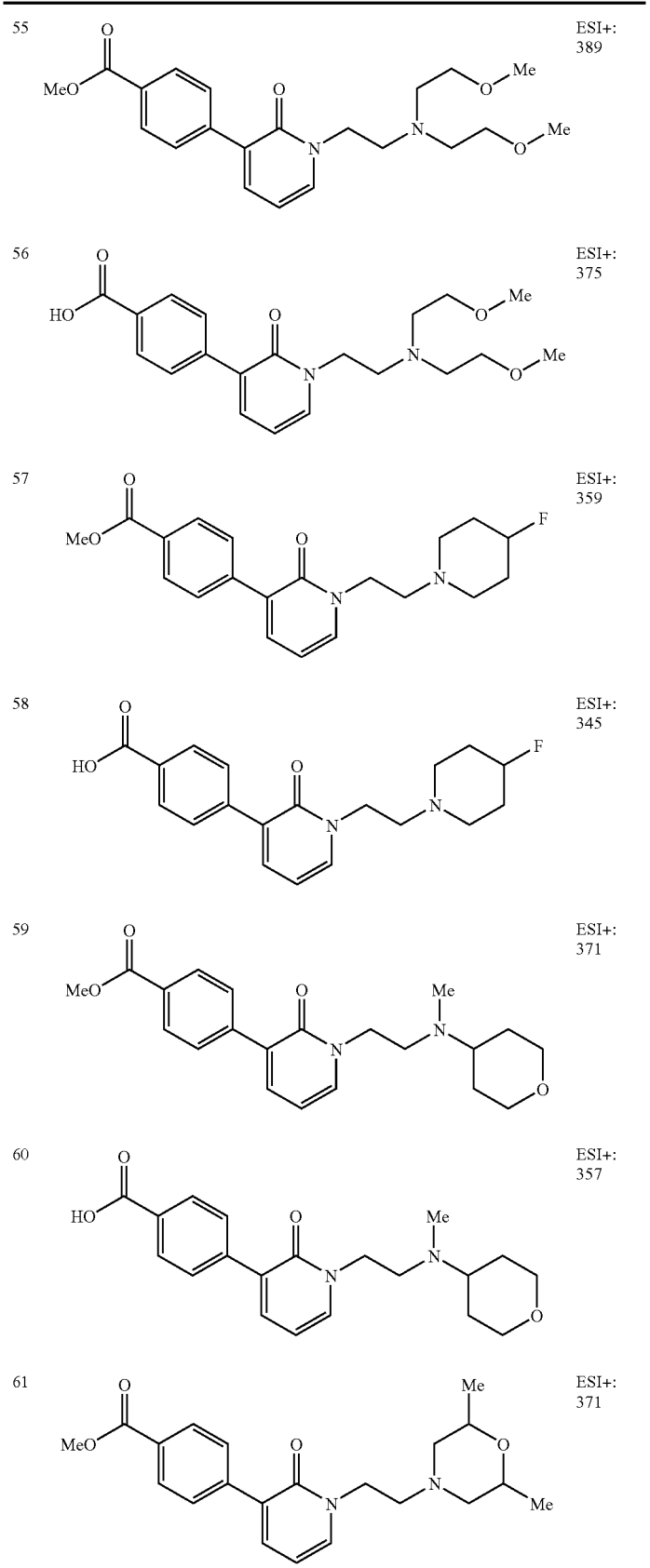

TABLE 4-continued

| | | |
|---|---|---|
| 62 | | ESI+: 357 |
| 63 | | ESI+: 357 |
| 64 | | ESI+: 343 |
| 65 | | ESI+: 315 |
| 66 | | ESI+: 301 |
| 67 | | ESI+: 355 |
| 68 | | ESI+: 341 |

TABLE 4-continued
| 69 | 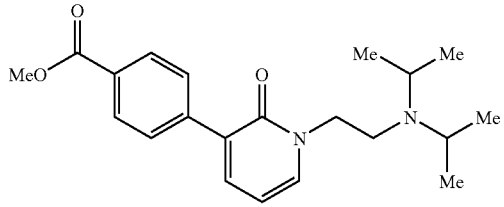 | FAB+: 357 |
|---|---|---|
| 70 | 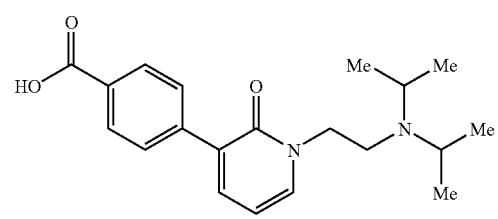 | FAB+: 343 |
| 71 | 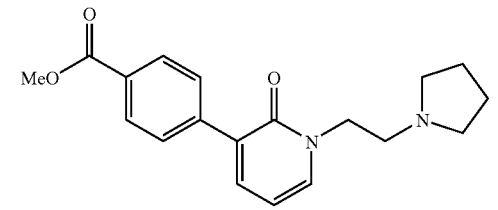 | FAB+: 327 |
| 72 | 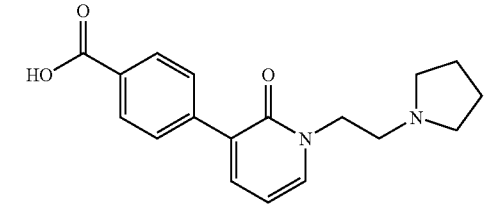 | ESI+: 313 |
| 73 | 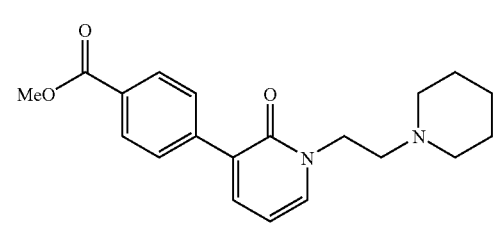 | FAB+: 341 |
| 74 | 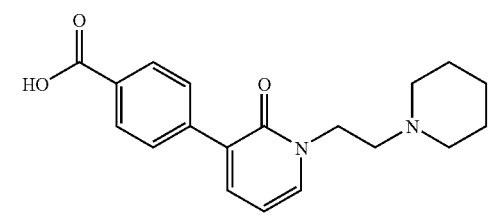 | ESI+: 327 |

TABLE 5

| | | |
|---|---|---|
| 75 | (structure) | FAB+: 419 |
| 76 | (structure) | FAB+: 405 |
| 77 | (structure) | ESI+: 456 |
| 78 | (structure) | ESI−: 440 |
| 79 | (structure) | FAB+: 387 |
| 80 | (structure) | ESI−: 371 |
| 81 | (structure) | FAB+: 457 |

TABLE 5-continued
| 82 | 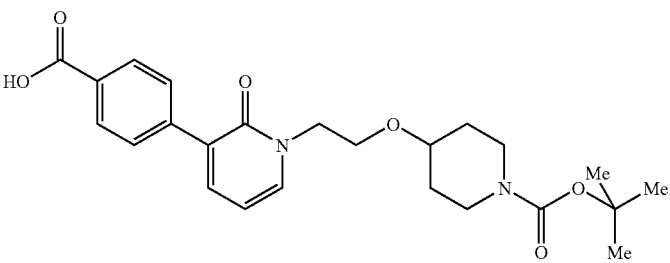 | ESI+: 443 |
| 83 | 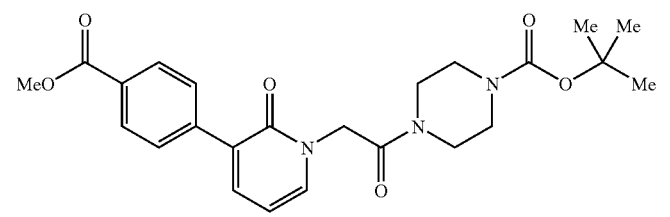 | FAB+: 456 |
| 84 | 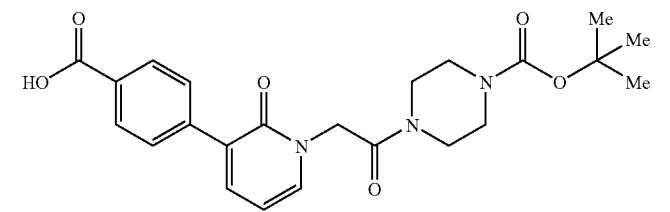 | FAB+: 442 |
| 85 | 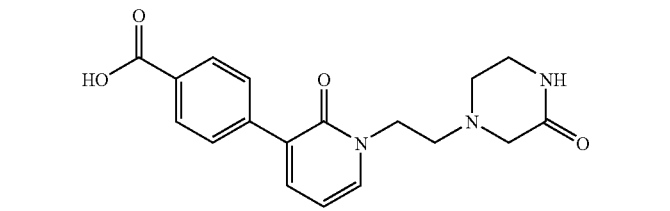 | ESI+: 342 |
| 86 | 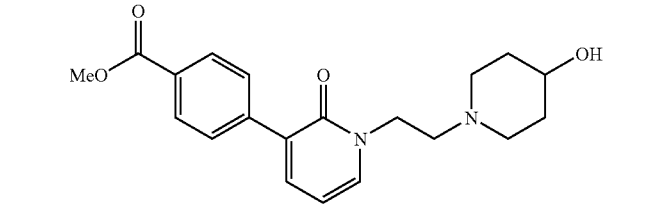 | FAB+: 357 |
| 87 | 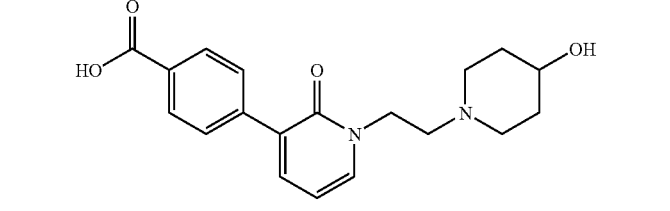 | ESI+: 343 |
| 88 | 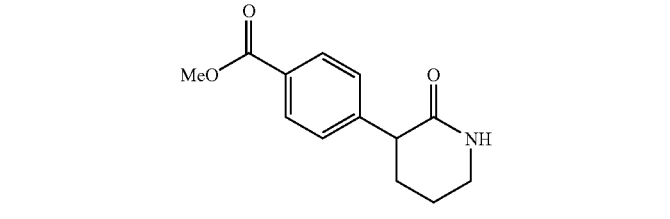 | ESI+: 248 |

TABLE 5-continued
| 89 | 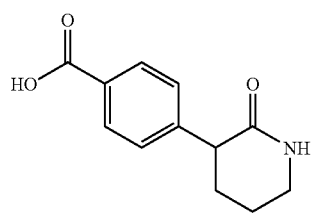 | ESI+: 220 |
| --- | --- | --- |
| 90 | 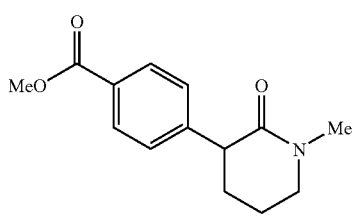 | FAB+: 248 |
| 91 | 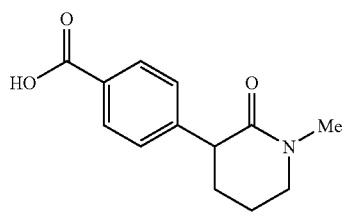 | ESI+: 234 |
| 92 | 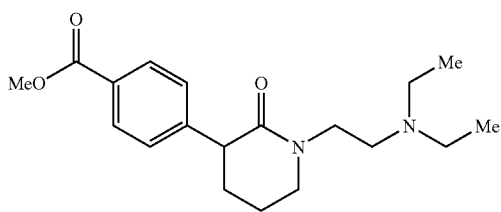 | FAB+: 333 |
TABLE 6
| 93 | 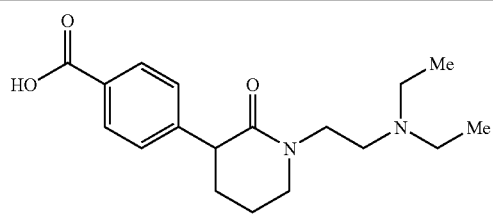 | FAB+: 319 |
| --- | --- | --- |
| 94 | 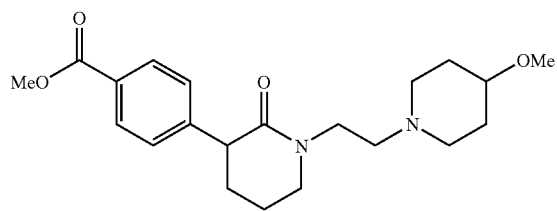 | FAB+: 375 |
| 95 | 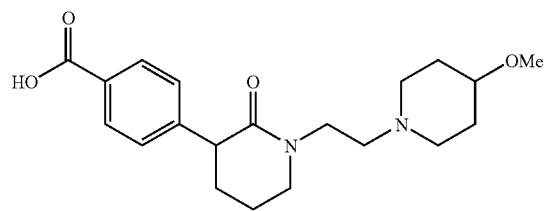 | FAB+: 361 |

TABLE 6-continued
| 96 | 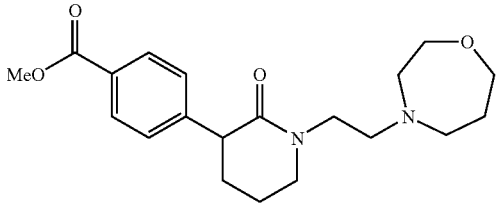 | ESI+: 361 |
| --- | --- | --- |
| 97 | 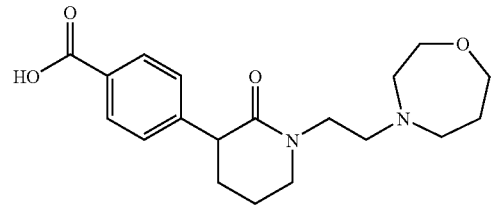 | ESI+: 347 |
| 98 | 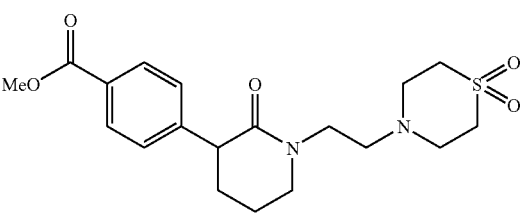 | ESI+: 395 |
| 99 | 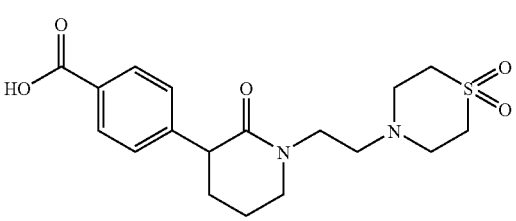 | ESI+: 381 |
| 100 | 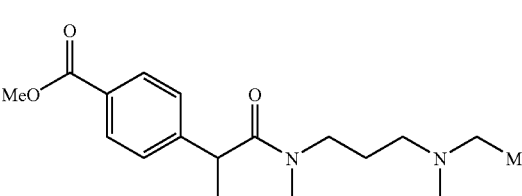 | ESI+: 347 |
| 101 | 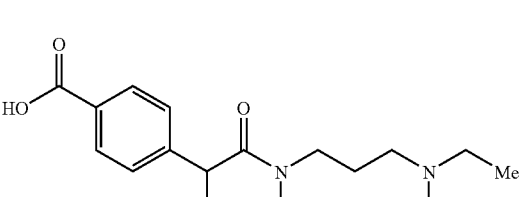 | ESI+: 333 |
| 102 | 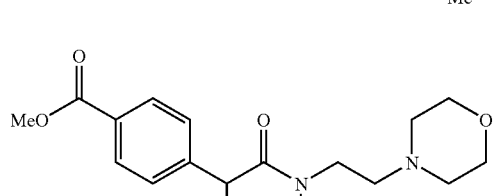 | ESI+: 347 |

TABLE 6-continued
| 103 | 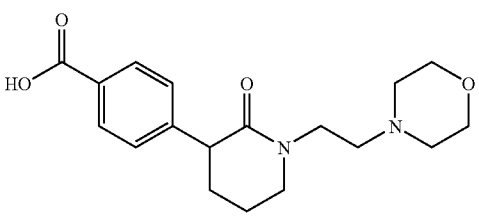 | ESI+: 343 |
| 104 | 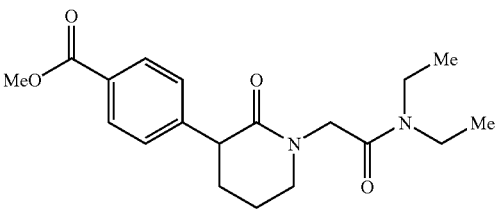 | ESI+: 347 |
| 105 | 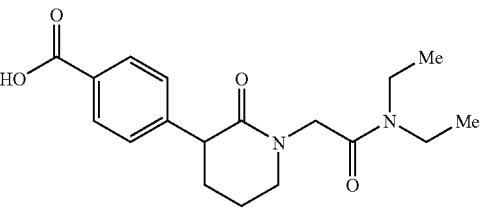 | ESI+: 333 |
| 106 | 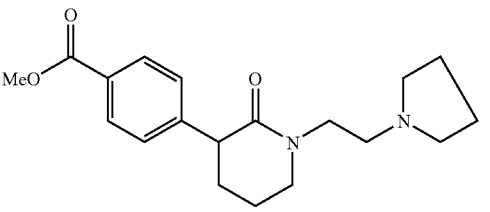 | FAB+: 331 |
| 107 | 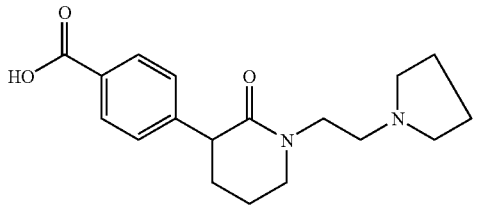 | ESI+: 317 |
| 108 | 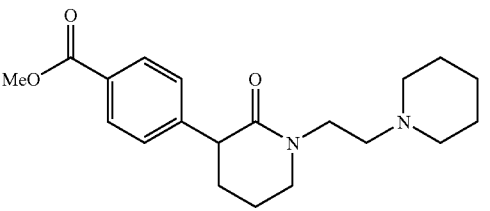 | FAB+: 345 |
| 109 | 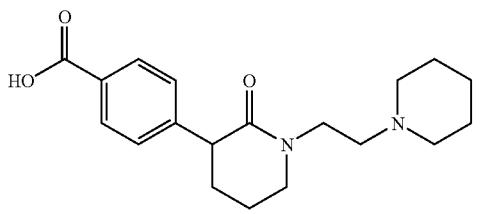 | ESI+: 331 |

TABLE 6-continued

| 110 | [Structure: methyl 4-(2-oxo-1-(2-(diisopropylamino)ethyl)piperidin-3-yl)benzoate with MeO-C(=O)-phenyl and N(iPr)₂ group] | FAB+: 361 |
| 111 | [Structure: 4-(2-oxo-1-(2-(diisopropylamino)ethyl)piperidin-3-yl)benzoic acid] | FAB+: 347 |
| 112 | [Structure: methyl 4-(2-oxo-1-(3-(piperidin-1-yl)propyl)piperidin-3-yl)benzoate] | ESI+: 359 |

TABLE 7

| 113 | [Structure: 4-(2-oxo-1-(3-(piperidin-1-yl)propyl)piperidin-3-yl)benzoic acid] | ESI+: 345 |
| 114 | [Structure: methyl 4-(2-oxo-1-(2-(4-Boc-piperazin-1-yl)ethyl)piperidin-3-yl)benzoate] | FAB+: 446 |
| 115 | [Structure: 4-(2-oxo-1-(2-(4-Boc-piperazin-1-yl)ethyl)piperidin-3-yl)benzoic acid] | ESI+: 432 |
| 116 | [Structure: methyl 4-(2-oxo-1-(2-((S)-2-methylpyrrolidin-1-yl)ethyl)piperidin-3-yl)benzoate] | FAB+: 345 |

TABLE 7-continued
| 117 | 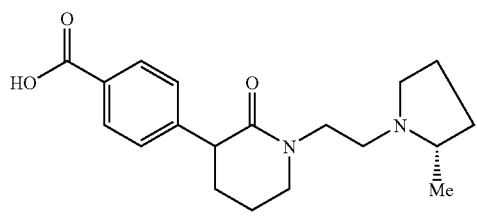 | FAB+: 331 |
| 118 | 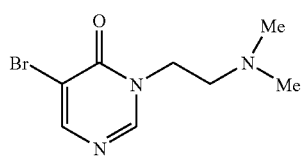 | FAB+: 246 |
| 119 | 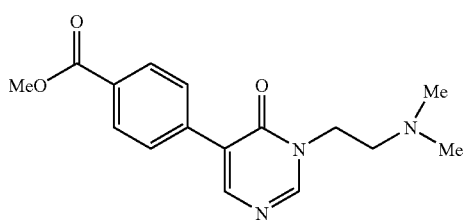 | FAB+: 302 |
| 120 | 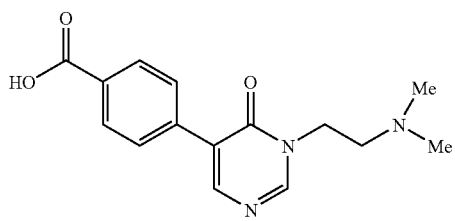 | ESI+: 288 |
| 121 | 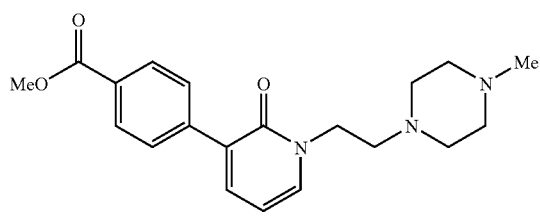 | FAB+: 356 |
| 122 | 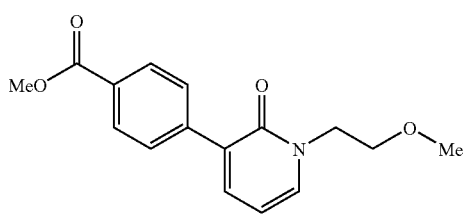 | FAB+: 288 |
| 123 | 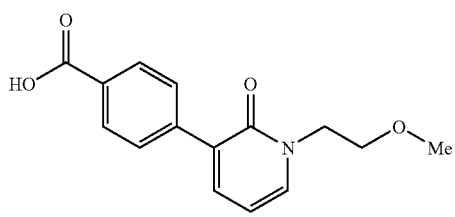 | FAB+: 274 |

TABLE 7-continued
| 124 | 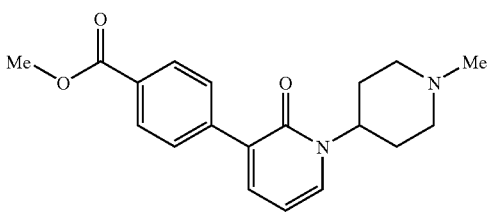 | FAB+: 327 |
| 125 | 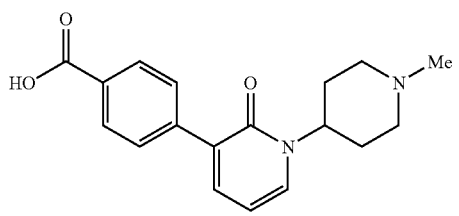 | FAB+: 313 |
| 126 | 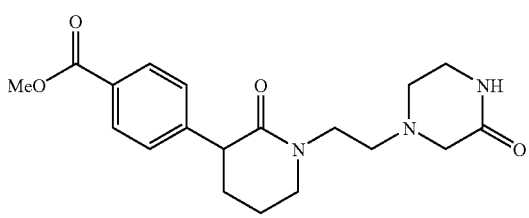 | ESI+: 360 |
| 127 | 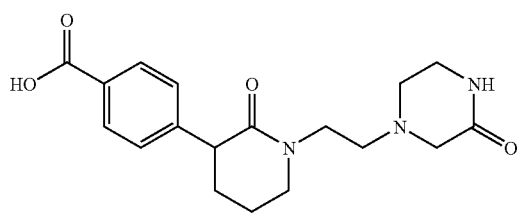 | ESI−: 344 |
| 128 | 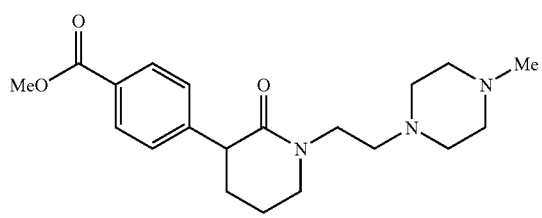 | FAB+: 360 |
| 129 | 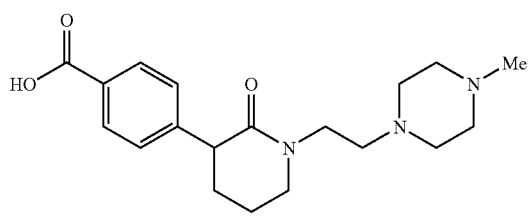 | FAB+: 346 |
| 130 | 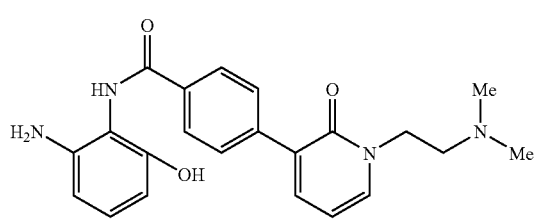 | FAB+: 393 |

TABLE 8
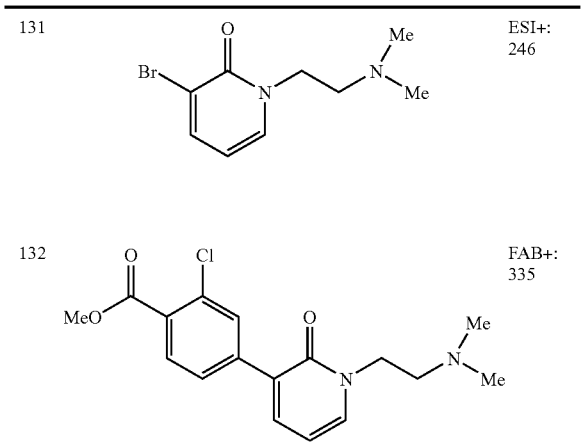
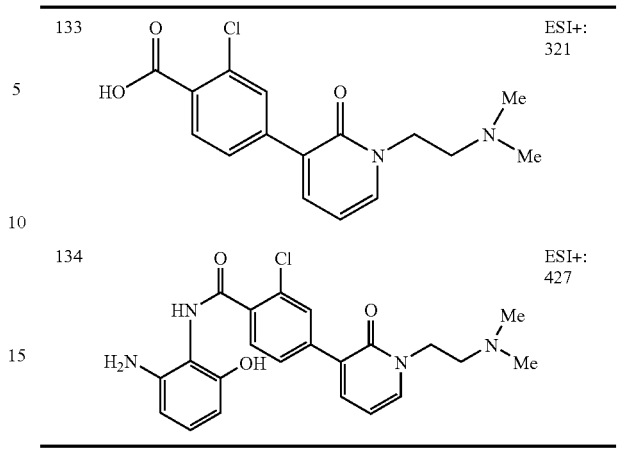
TABLE 9
| Ex | Structure | DATA |
| --- | --- | --- |
| 1 | 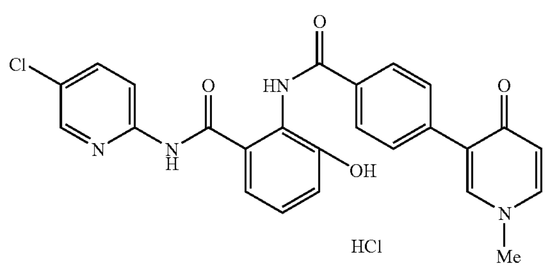 | NMR(DMSO-d6): 4.10 (3H, s), 7.09-7.19 (2H, m), 7.26 (1H, t, J = 7.9 Hz), 7.41 (1H, d, J = 7.0 Hz), 7.73-7.79 (2H, m), 7.88 (1H, dd, J = 2.8, 8.9 Hz), 8.00-8.07 (2H, m), 8.11 (1H, d, J = 8.9 Hz), 8.34 (1H, d, J = 2.8 Hz), 8.44-8.50 (1H, m), 8.71-8.77 (1H, m), 9.83 (1H, s), 9.93(1H, s), 10.54 (1H, s)<br>FAB+: 474 |
| 2 | 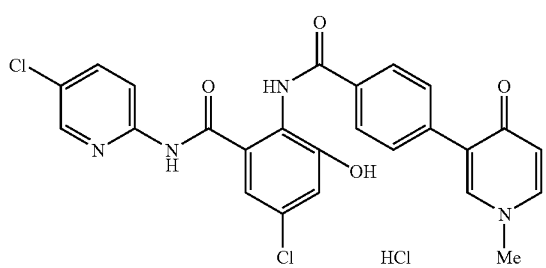 | NMR(DMSO-d6): 4.06 (3H, s), 7.16 (2H, s), 7.26 (1H, d, J = 7.0 Hz), 7.76 (2H, d, J = 8.5 Hz), 7.88 (1H, dd, J = 2.7, 8.9 Hz), 8.01 (2H, d, J = 8.4 Hz), 8.08 (1H, d, J = 8.9 Hz), 8.33-8.44 (2H, m), 8.62-8.73 (1H, m), 9.80 (1H, s), 10.47 (1H, s), 10.74 (1H, s)<br>FAB+: 509 |
| 3 | 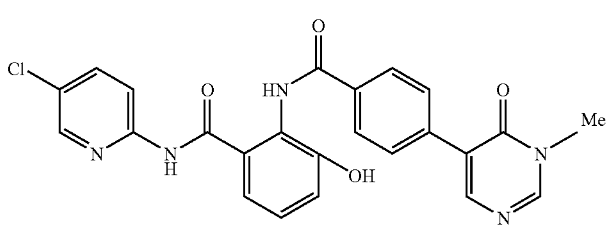 | FAB+: 476 |
| 4 | 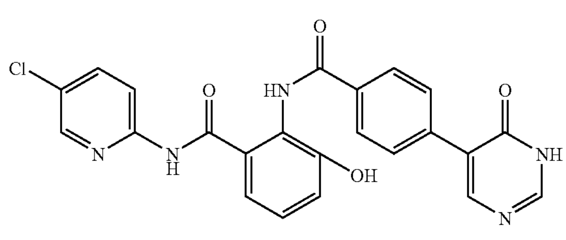 | ESI−: 460 |

TABLE 9-continued

| Ex | Structure | DATA |
|---|---|---|
| 5 | 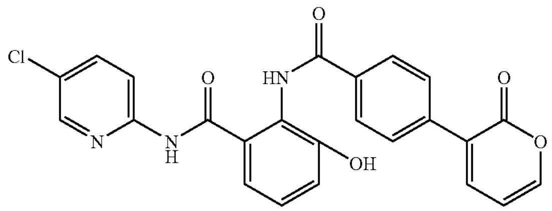 | ESI−: 460 |
| 6 | 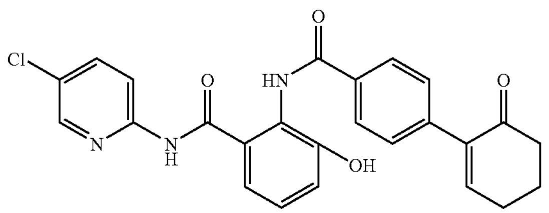 | FAB+: 462 |

TABLE 10

| Ex | Structure | DATA |
|---|---|---|
| 7 | 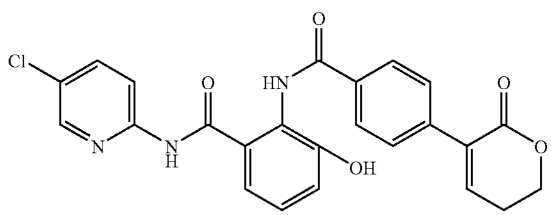 | ESI−: 462 |
| 8 | 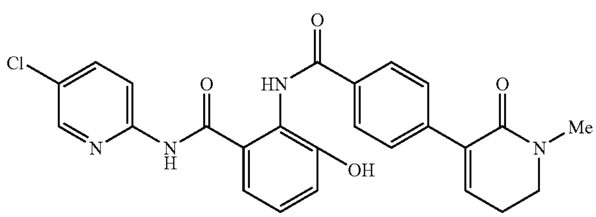 | FAB+: 477 |
| 9 | 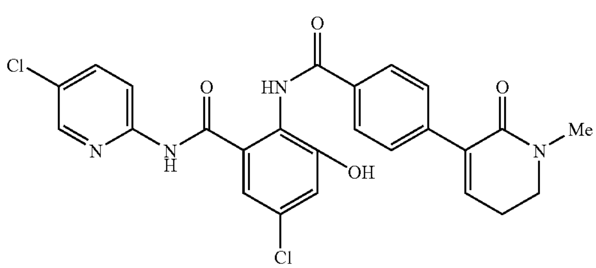 | FAB+: 511 |
| 10 | 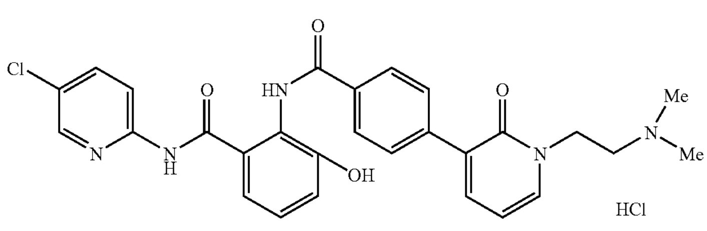 | NMR(DMSO-d6): 2.86 (3H, s), 2.87 (3H, s), 3.40-3.49 (2H, m), 4.37 (2H, t, J = 6.4 Hz), 6.48 (1H, t, J = 6.9 Hz), 7.11-7.17 (2H, m), 7.25 (1H, t, J = 7.9 Hz), 7.75-7.98 (7H, m), 8.13 (1H, d, J = 8.9 Hz), 8.34 (1H, d, J = 3.1 Hz), 9.71-10.20 (3H, m), 10.53 (1H, s) ESI+: 532 |

TABLE 10-continued
| 11 | 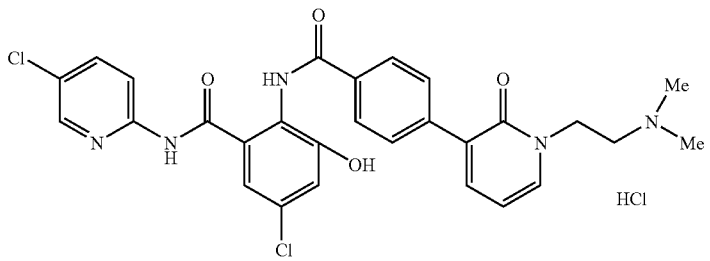 | NMR(DMSO-d6):<br>2.86 (3H, s), 2.87 (3H, s), 3.28-3.58 (2H, m), 4.37 (2H, t, J = 6.4 Hz), 6.48 (1H, t, J = 6.9 Hz), 7.14-7.19 (2H, m), 7.75-7.96 (7H, m), 8.08 (1H, d, J = 8.9 Hz), 8.36 (1H, d, J = 2.3 Hz), 9.72 (1H, s), 9.99 (1H, s), 10.49 (1H, s), 10.71 (1H, s)<br>ESI+: 566 |
|---|---|---|
| 12 | 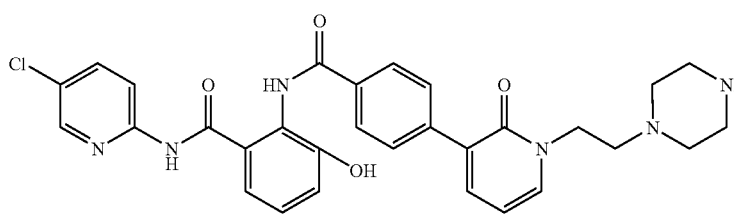 | NMR(DMSO-d6):<br>2.37-2.45 (4H, m), 2.58 (2H, t, J = 6.4 Hz), 2.68-2.76 (4H, m), 4.08 (2H, t, J = 6.4 Hz), 6.35 (1H, t, J = 6.9 Hz), 7.08 (1H, d, J = 8.8 Hz), 7.15-7.31 (2H, m), 7.66-7.75 (2H, m), 7.81 (2H, d, J = 8.2 Hz), 7.86-7.91 (1H, m), 7.99 (2H, d, J = 8.0 Hz), 8.17 (1H, d, J = 9.0 Hz), 8.34 (1H, d, J = 2.6 Hz)<br>FAB+: 573 |
TABLE 11
| 13 | 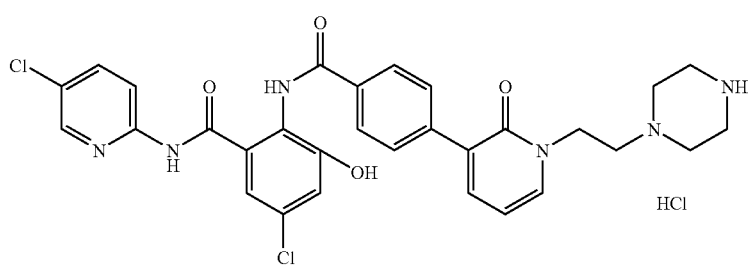 | ESI+: 607 |
|---|---|---|
| 14 | 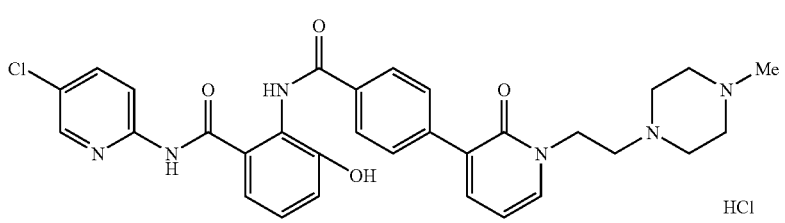 | NMR(DMSO-d6):<br>2.83 (3H, s), 3.12-4.57 (12H, m), 6.46 (1H, t, J = 6.9 Hz), 7.11-7.18 (2H, m), 7.25 (1H, t, J = 7.8 Hz), 7.71-7.97 (7H, m), 8.13 (1H, d, J = 9.0 Hz), 8.35 (1H, d, J = 2.8 Hz), 9.53-10.21 (2H, m), 10.54 (1H, s), 11.86 (1H, s)<br>ESI+: 587 |
| 15 | 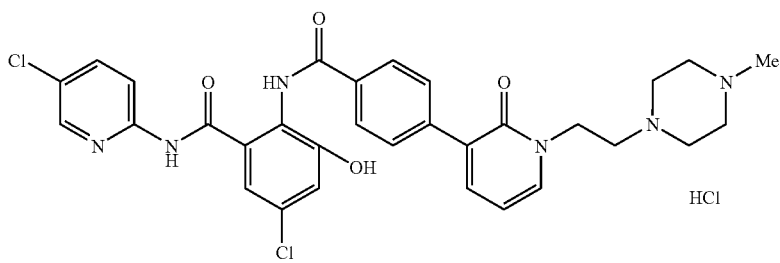 | ESI+: 621 |
| 16 | 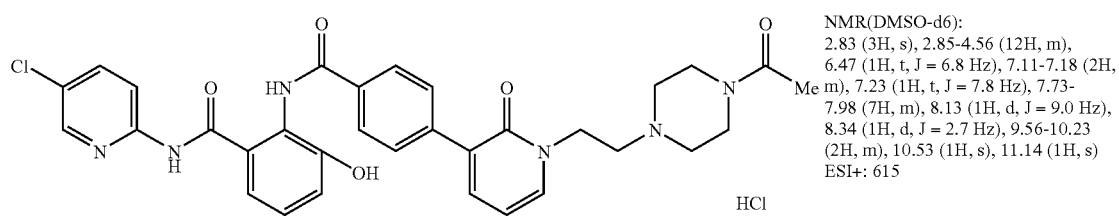 | NMR(DMSO-d6):<br>2.83 (3H, s), 2.85-4.56 (12H, m), 6.47 (1H, t, J = 6.8 Hz), 7.11-7.18 (2H, m), 7.23 (1H, t, J = 7.8 Hz), 7.73-7.98 (7H, m), 8.13 (1H, d, J = 9.0 Hz), 8.34 (1H, d, J = 2.7 Hz), 9.56-10.23 (2H, m), 10.53 (1H, s), 11.14 (1H, s)<br>ESI+: 615 |

TABLE 11-continued
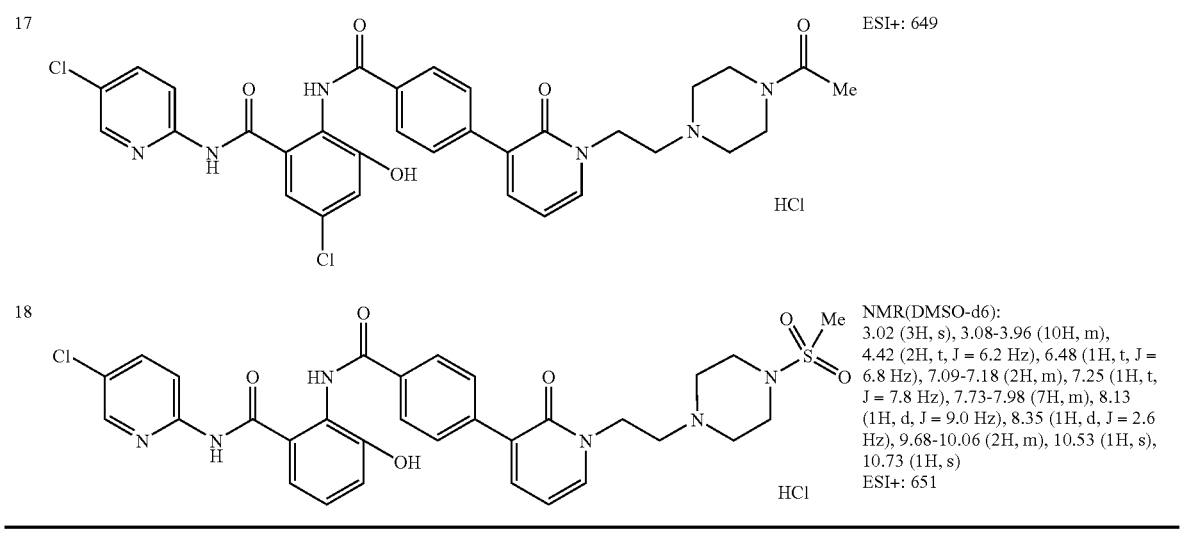
| 17 | ESI+: 649 · HCl |
| 18 | NMR(DMSO-d6): 3.02 (3H, s), 3.08-3.96 (10H, m), 4.42 (2H, t, J = 6.2 Hz), 6.48 (1H, t, J = 6.8 Hz), 7.09-7.18 (2H, m), 7.25 (1H, t, J = 7.8 Hz), 7.73-7.98 (7H, m), 8.13 (1H, d, J = 9.0 Hz), 8.35 (1H, d, J = 2.6 Hz), 9.68-10.06 (2H, m), 10.53 (1H, s), 10.73 (1H, s) ESI+: 651 · HCl |
TABLE 12
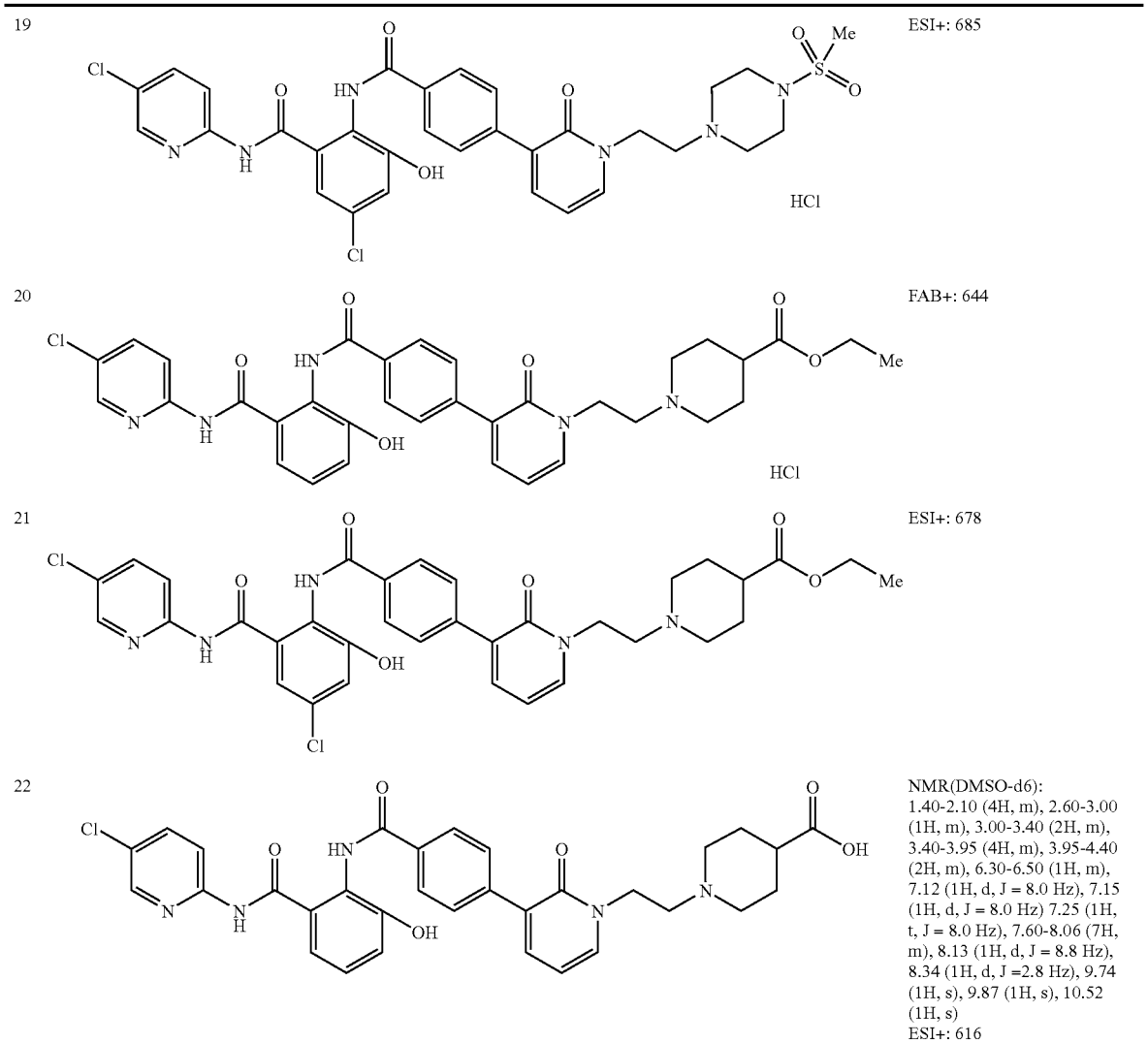
| 19 | ESI+: 685 · HCl |
| 20 | FAB+: 644 · HCl |
| 21 | ESI+: 678 |
| 22 | NMR(DMSO-d6): 1.40-2.10 (4H, m), 2.60-3.00 (1H, m), 3.00-3.40 (2H, m), 3.40-3.95 (4H, m), 3.95-4.40 (2H, m), 6.30-6.50 (1H, m), 7.12 (1H, d, J = 8.0 Hz), 7.15 (1H, d, J = 8.0 Hz) 7.25 (1H, t, J = 8.0 Hz), 7.60-8.06 (7H, m), 8.13 (1H, d, J = 8.8 Hz), 8.34 (1H, d, J = 2.8 Hz), 9.74 (1H, s), 9.87 (1H, s), 10.52 (1H, s) ESI+: 616 |

TABLE 12-continued

| # | Structure | Data |
|---|---|---|
| 23 | (structure) | ESI+: 650 |
| 24 | (structure) | NMR(DMSO-d6): 2.89 (3H, s), 3.20-3.70 (6H, m), 3.70-4.20 (2H, m), 4.30-4.60 (2H, m), 6.48 (1H, t, J = 6.9 Hz), 7.09-7.19 (2H, m), 7.25 (1H, t, J = 7.8 Hz), 7.77 (1H, dd, J = 1.9, 7.1 Hz), 7.80-7.91 (4H, m), 7.91-8.00 (2H, m), 8.13 (1H, d, J = 9.0 Hz), 8.34 (1H, d, J = 2.8 Hz), 9.60-10.20 (2H, m), 10.53 (1H, s)<br>ESI+: 601 |

TABLE 13

| # | Structure | Data |
|---|---|---|
| 25 | (structure) | ESI+: 635 |
| 26 | (structure) | NMR(DMSO-d6):<br>1.79-2.21 (4H, m), 2.75-2.84 (6H, m), 3.19-3.82 (7H, m), 7.09-7.18 (2H, m), 7.20-7.28 (1H, m), 7.33 (2H, d, J = 8.3 Hz), 7.81-7.91 (3H, m), 8.13 (1H, d, J = 9.0 Hz), 8.34 (1H, d, J = 2.4 Hz), 9.69 (1H, s), 9.89 (1H, s), 10.11 (1H, s), 10.51 (1H, s)<br>ESI+: 536 |
| 27 | (structure) | NMR (DMSO-d6):<br>1.80-2.12 (4H, m), 2.77-2.84 (6H, m), 3.17-3.82 (7H, m), 7.13-7.16 (2H, m), 7.32 (2H, d, J = 8.3 Hz), 7.83 (2H, d, J = 8.3 Hz), 7.88 (1H, dd, J = 8.9, 2.5 Hz), 8.08 (1H, d, J = 8.9 Hz), 8.36 (1H, d, J = 2.5 Hz), 9.64 (1H, s), 9.87 (1H, s), 10.43 (1H, s), 10.70 (1H, s)<br>FAB+: 570 |
| 28 | (structure) | NMR (DMSO-d6):<br>6.33 (1H, t, J = 6.4 Hz), 7.07-7.19 (2H, m), 7.21-7.29 (1H, m), 7.40-7.47 (1H, m), 7.71-7.99 (6H, m), 8.14 (1H, d, J =8.9 Hz), 8.31-8.37 (1H, m), 9.74 (1H, s), 9.84 (1H, s), 10.52 (1H, s), 11.88 (1H, s)<br>FAB−: 459 |

TABLE 13-continued

| | | |
|---|---|---|
| 29 | 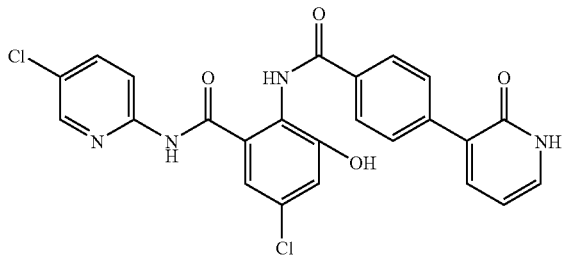 | NMR (DMSO-d6):<br>6.32 (1H, t, J = 6.7 Hz), 7.09-7.19 (2H, m), 7.44 (1H, dd, J = 6.4, 1.9 Hz), 7.74 (1H, dd, J = 7.0, 2.0 Hz), 7.81-7.94 (5H, m), 8.10 (1H, d, J = 8.9 Hz), 8.36 (1H, d, J = 2.6 Hz), 9.69 (1H, s), 10.37 (1H, s), 10.71 (1H, s), 11.88 (1H, s)<br>FAB+: 495 |
| 30 | 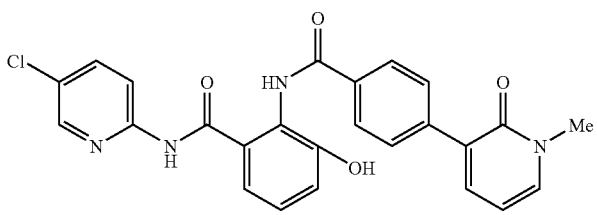 | NMR (DMSO-d6):<br>3.52 (3H, s), 6.35 (1H, t, J = 6.9 Hz), 7.07-7.19 (2H, m), 7.25 (1H, t, J = 7.8 Hz), 7.71 (1H, dd, J = 7.0, 2.0 Hz), 7.75-7.97 (6H, m), 8.14 (1H, d, J = 8.9 Hz), 8.35 (1H, d, J = 2.9 Hz), 9.74 (1H, s), 9.84 (1H, s), 10.53 (1H, s)<br>ESI+: 475 |

TABLE 14

| | | |
|---|---|---|
| 31 | 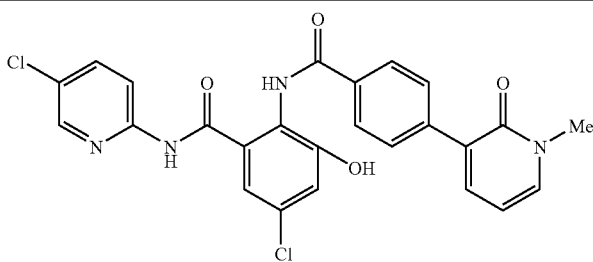 | FAB+: 509 |
| 32 | 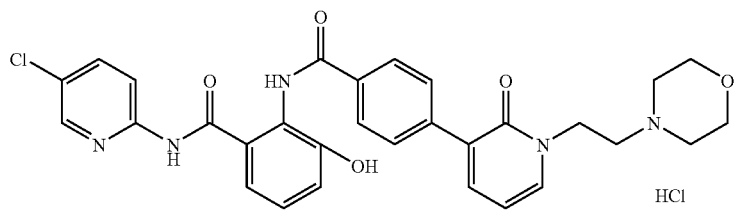 | NMR (DMSO-d6):<br>3.07-3.24 (2H, m), 3.40-3.84 (6H, m), 3.93-4.10 (2H, m), 4.41 (2H, t, J = 6.5 Hz), 6.49 (1H, t, J = 6.9 Hz), 7.09-7.18 (2H, m), 7.25 (1H, t, J = 7.9 Hz), 7.78 (1H, dd, J = 1.9, 7.2 Hz), 7.81-7.86 (3H, m), 7.88 (1H, dd, J = 2.7, 8.9 Hz), 7.95 (2H, d, J = 8.4 Hzm), 8.13 (1H, d, J = 9.0 Hz), 8.35 (1H, d, J = 2.3 Hz), 9.70-9.99 (2H, m), 10.39-10.57 (2H, m)<br>FAB+: 574 |
| 33 | 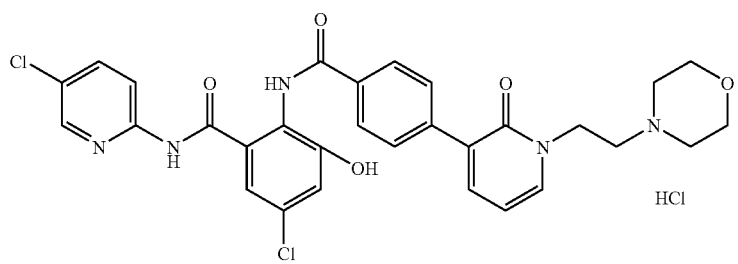 | NMR (DMSO-d6):<br>3.09-3.24 (2H, m), 3.46-3.82 (6H, m), 3.95-4.07 (2H, m), 4.40 (2H, t, J = 6.3 Hz), 6.49 (1H, t, J = 6.8 Hz), 7.15 (2H, s), 7.75-7.96 (7H, m), 8.08 (1H, d, J = 9.0 Hz), 8.36 (1H, d, J = 3.0 Hz), 9.71 (1H, s), 10.45 (2H, s), 10.72 (1H, s)<br>FAB+: 608 |
| 34 | 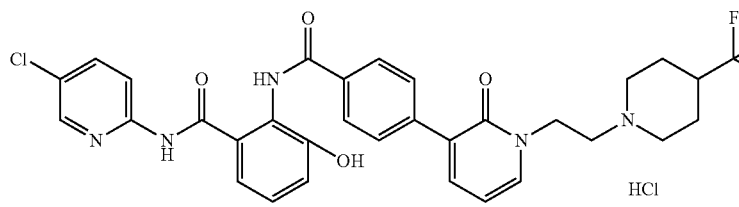 | NMR (DMSO-d6):<br>1.79-2.13 (4H, m), 2.60-2.80 (1H, m), 3.00-3.14 (2H, m), 3.33-3.79 (4H, m), 4.42 (2H, t, J = 6.7 Hz), 6.48 (1H, t, J = 6.9 Hz), 7.14 (2H, t, 7.8 Hz), 7.25 (1H, t, J = 7.9 Hz), 7.74-7.91 (5H, m), 7.95 (2H, d, J = 8.4 Hz), 8.13 (1H, d, J = 9.0 Hz), 8.34 (1H, d, J = 2.5 Hz), 9.69-10.05 (2H, m), 10.41-10.58 (2H, m)<br>FAB+: 640 |

TABLE 14-continued

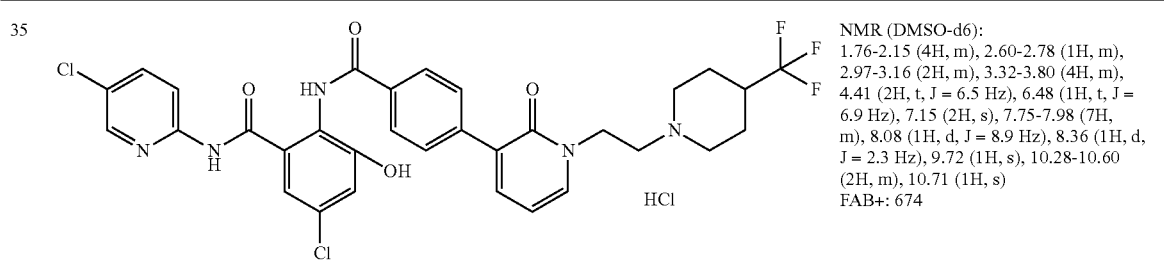

| 35 | NMR (DMSO-d6): 1.76-2.15 (4H, m), 2.60-2.78 (1H, m), 2.97-3.16 (2H, m), 3.32-3.80 (4H, m), 4.41 (2H, t, J = 6.5 Hz), 6.48 (1H, t, J = 6.9 Hz), 7.15 (2H, s), 7.75-7.98 (7H, m), 8.08 (1H, d, J = 8.9 Hz), 8.36 (1H, d, J = 2.3 Hz), 9.72 (1H, s), 10.28-10.60 (2H, m), 10.71 (1H, s) FAB+: 674 |

TABLE 15

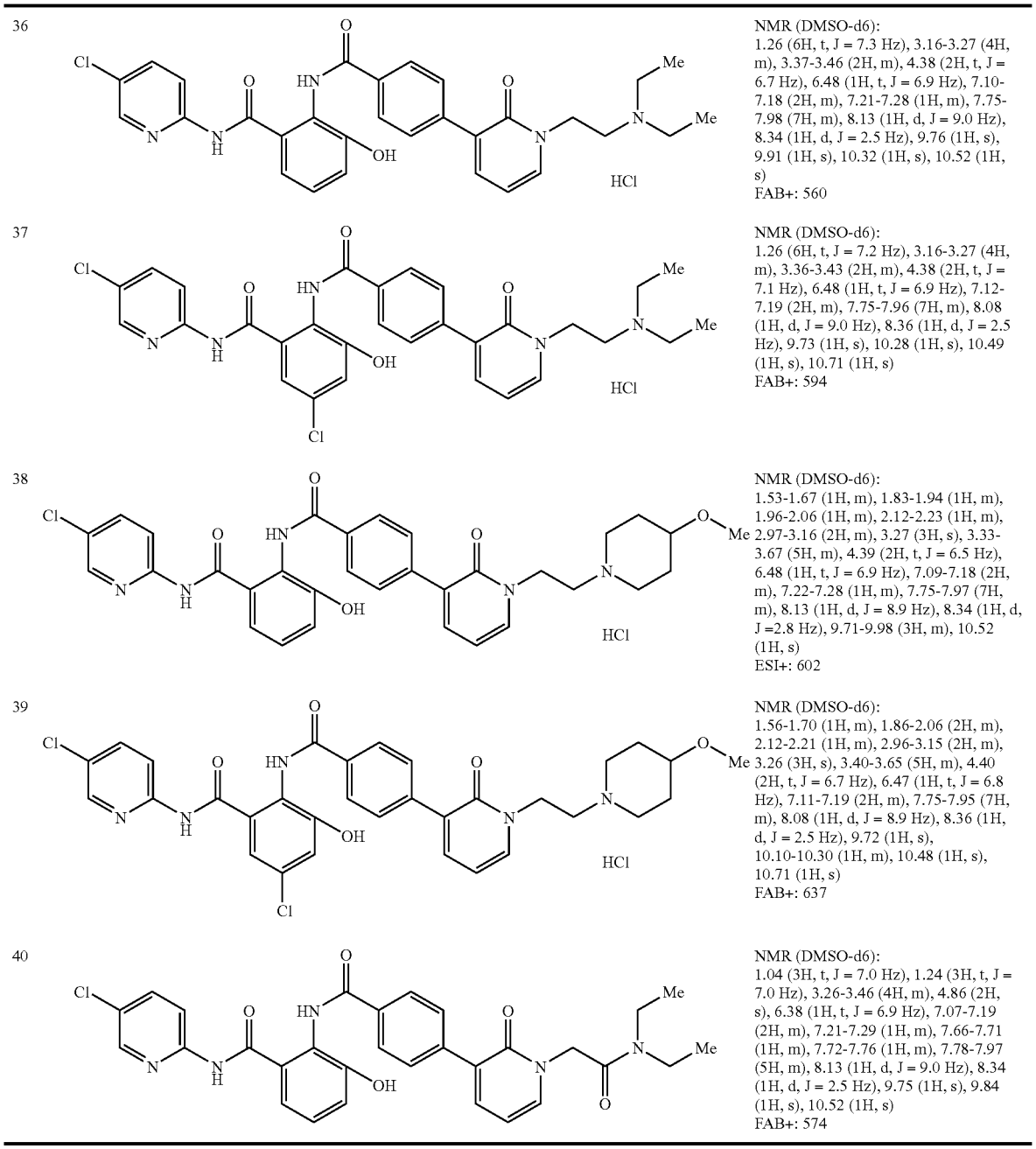

| 36 | NMR (DMSO-d6): 1.26 (6H, t, J = 7.3 Hz), 3.16-3.27 (4H, m), 3.37-3.46 (2H, m), 4.38 (2H, t, J = 6.7 Hz), 6.48 (1H, t, J = 6.9 Hz), 7.10-7.18 (2H, m), 7.21-7.28 (1H, m), 7.75-7.98 (7H, m), 8.13 (1H, d, J = 9.0 Hz), 8.34 (1H, d, J = 2.5 Hz), 9.76 (1H, s), 9.91 (1H, s), 10.32 (1H, s), 10.52 (1H, s) FAB+: 560 |
| 37 | NMR (DMSO-d6): 1.26 (6H, t, J = 7.2 Hz), 3.16-3.27 (4H, m), 3.36-3.43 (2H, m), 4.38 (2H, t, J = 7.1 Hz), 6.48 (1H, t, J = 6.9 Hz), 7.12-7.19 (2H, m), 7.75-7.96 (7H, m), 8.08 (1H, d, J = 9.0 Hz), 8.36 (1H, d, J = 2.5 Hz), 9.73 (1H, s), 10.28 (1H, s), 10.49 (1H, s), 10.71 (1H, s) FAB+: 594 |
| 38 | NMR (DMSO-d6): 1.53-1.67 (1H, m), 1.83-1.94 (1H, m), 1.96-2.06 (1H, m), 2.12-2.23 (1H, m), 2.97-3.16 (2H, m), 3.27 (3H, s), 3.33-3.67 (5H, m), 4.39 (2H, t, J = 6.5 Hz), 6.48 (1H, t, J = 6.9 Hz), 7.09-7.18 (2H, m), 7.22-7.28 (1H, m), 7.75-7.97 (7H, m), 8.13 (1H, d, J = 8.9 Hz), 8.34 (1H, d, J = 2.8 Hz), 9.71-9.98 (3H, m), 10.52 (1H, s) ESI+: 602 |
| 39 | NMR (DMSO-d6): 1.56-1.70 (1H, m), 1.86-2.06 (2H, m), 2.12-2.21 (1H, m), 2.96-3.15 (2H, m), 3.26 (3H, s), 3.40-3.65 (5H, m), 4.40 (2H, t, J = 6.7 Hz), 6.47 (1H, t, J = 6.8 Hz), 7.11-7.19 (2H, m), 7.75-7.95 (7H, m), 8.08 (1H, d, J = 8.9 Hz), 8.36 (1H, d, J = 2.5 Hz), 9.72 (1H, s), 10.10-10.30 (1H, m), 10.48 (1H, s), 10.71 (1H, s) FAB+: 637 |
| 40 | NMR (DMSO-d6): 1.04 (3H, t, J = 7.0 Hz), 1.24 (3H, t, J = 7.0 Hz), 3.26-3.46 (4H, m), 4.86 (2H, s), 6.38 (1H, t, J = 6.9 Hz), 7.07-7.19 (2H, m), 7.21-7.29 (1H, m), 7.66-7.71 (1H, m), 7.72-7.76 (1H, m), 7.78-7.97 (5H, m), 8.13 (1H, d, J = 9.0 Hz), 8.34 (1H, d, J = 2.5 Hz), 9.75 (1H, s), 9.84 (1H, s), 10.52 (1H, s) FAB+: 574 |

TABLE 16
| 41 | 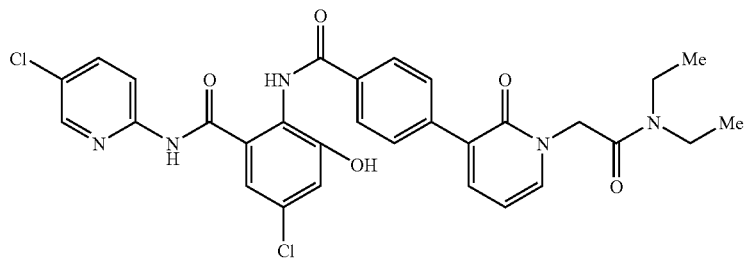 | NMR (DMSO-d6):<br>1.04 (3H, t, J = 7.1 Hz), 1.23 (3H, t, J = 7.1 Hz), 3.25-3.45 (4H, m), 4.86 (2H, s), 6.37 (1H, t, J = 6.8 Hz), 7.10-7.18 (2H, m), 7.65-7.71 (1H, m), 7.72-7.77 (1H, m), 7.78-7.94 (5H, m), 8.09 (1H, d, J = 9.0 Hz), 8.36 (1H, d, J = 2.7 Hz), 9.70 (1H, s), 10.36 (1H, s), 10.70 (1H, s)<br>FAB+: 608 |
|---|---|---|
| 42 | 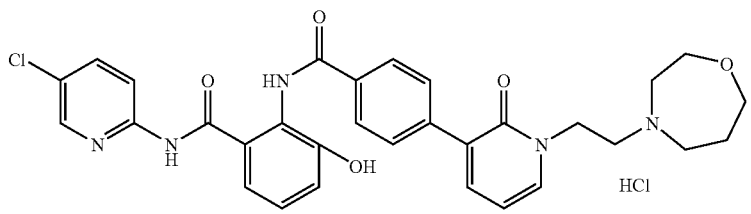 | ESI+: 588 |
| 43 | 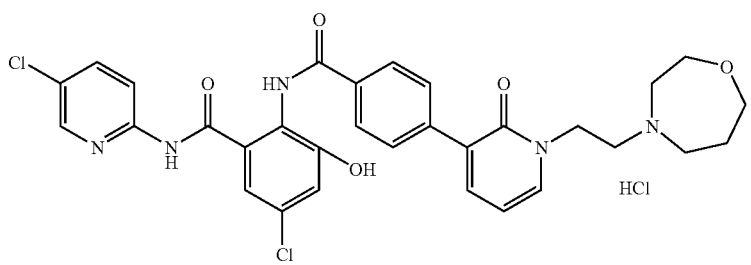 | ESI+: 622 |
| 44 | 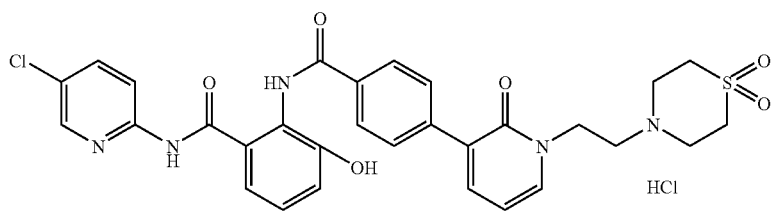 | NMR (DMSO-d6):<br>3.19-4.50 (12H, m), 6.40-6.51 (1H, m), 7.08-7.33 (3H, m), 7.68-8.04 (7H, m), 8.13 (1H, d, J = 9.0 Hz), 8.31-8.40 (1H, m), 9.75 (1H, s), 10.48-10.59 (1H, s)<br>ESI+: 622 |
| 45 | 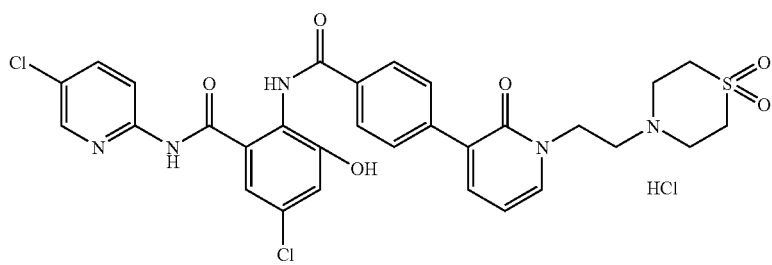 | NMR (DMSO-d6):<br>3.12-4.50 (12H, m), 6.44 (1H, t, J = 7.0 Hz), 7.04-7.23 (2H, m), 7.67-8.00 (7H, m), 8.09 (1H, d, J = 8.8 Hz), 8.31-8.41 (1H, m), 9.62-8.50 (1H, m), 10.25-10.59 (1H, m), 10.64-10.78 (1H, m)<br>ESI+: 656 |
| 46 | 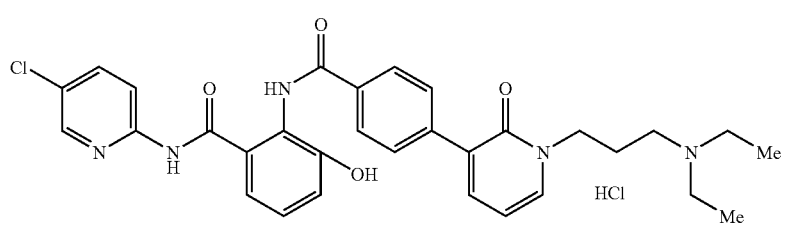 | NMR (DMSO-d6):<br>1.13-1.28 (6H, m), 2.04-2.18 (2H, m), 3.01-3.25 (6H, m), 3.98-4.17 (2H, m), 6.43 (1H, t, J = 6.8 Hz), 7.11-7.32 (3H, m), 7.69-8.04 (7H, m), 8.10-8.19 (1H, m), 8.33-8.39 (1H, m), 9.76 (1H, s), 10.27 (1H, s), 10.54 (1H, s)<br>ESI+: 574 |

TABLE 17

| | | |
|---|---|---|
| 47 | (structure) HCl | NMR (DMSO-d6): 1.19 (6H, t, J = 7.5 Hz), 2.02-2.19 (2H, m), 2.97-3.22 (6H, m), 3.97-4.18 (2H, m), 6.43 (1H, t, J = 6.8 Hz), 7.16 (2H, s), 7.65-8.02 (7H, m), 8.09 (1H, d, J = 8.8 Hz), 8.36 (1H, d, J = 2.6 Hz), 9.72 (1H, s), 9.98 (1H, s), 10.47 (1H, s), 10.71 (1H, s) ESI+: 608 |
| 48 | (structure) HCl | ESI+: 576 |
| 49 | (structure) HCl | FAB+: 610 |
| 50 | (structure) HCl | FAB+: 620 |
| 51 | (structure) HCl | FAB+: 654 |
| 52 | (structure) HCl | FAB+: 590 |

TABLE 17-continued
| 53 | 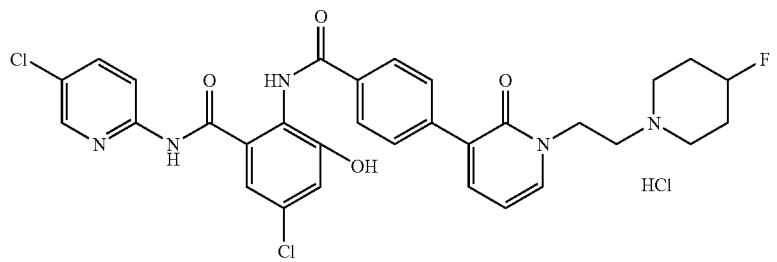 | FAB+: 624 |
TABLE 18
| 54 | 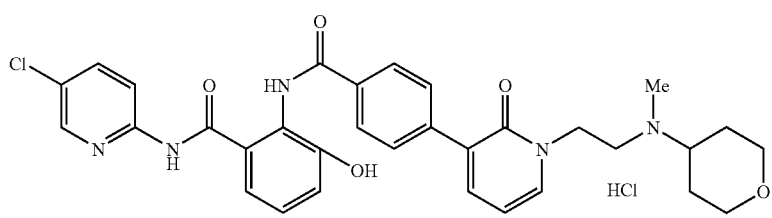 | FAB+: 602 |
| 55 | 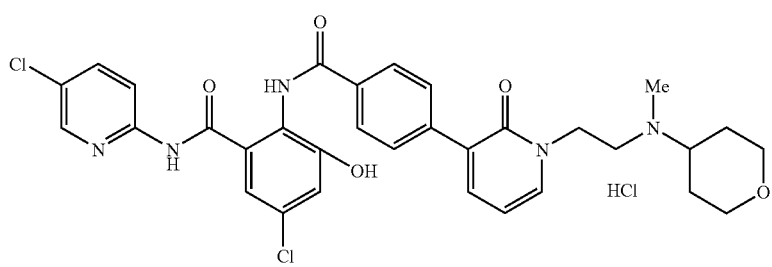 | FAB+: 636 |
| 56 | 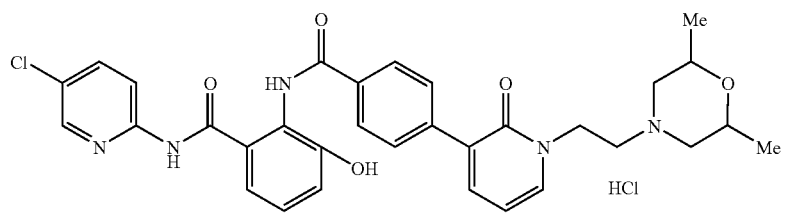 | FAB+: 602 |
| 57 | 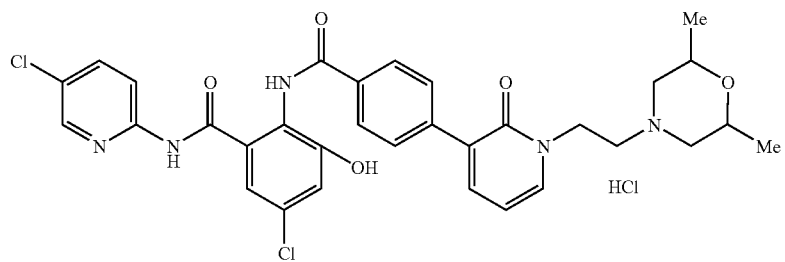 | FAB+: 636 |
| 58 | 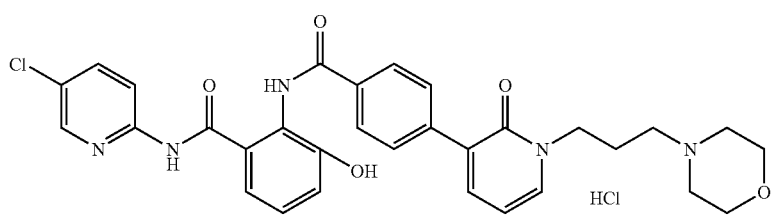 | FAB+: 588 |

TABLE 18-continued
| 59 | 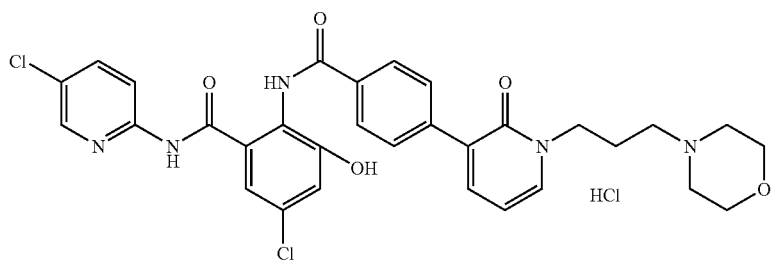 | FAB+: 622 |
| 60 | 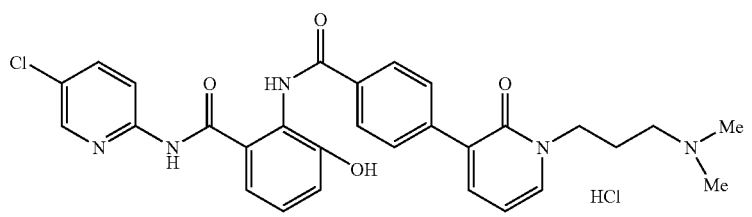 | NMR (DMSO-d6) 2.05-2.19 (2H, m), 2.70-2.80 (6H, m), 3.03-3.17 (2H, m), 3.60-4.30 (2H, m), 6.43 (1H, t, J = 6.8 Hz), 7.08-7.20 (2H, m), 7.20-7.30 (1H, m), 7.68-8.03 (7H, m), 8.08-8.17 (1H, m), 8.27-8.39 (1H, m), 9.68-9.86 (1H, m), 10.38 (1H, s), 10.54 (1H, d, J = 3.1 Hz) FAB+: 546 |
TABLE 19
| 61 | 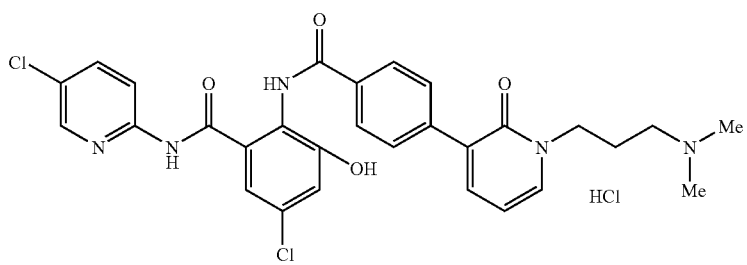 | NMR (DMSO-d6) 2.02-2.21 (2H, 2.02), 2.64-2.86 (6H, m), 3.00-3.20 (2H, m), 3.94-4.14 (2H, m), 6.42 (1H, t, J = 6.9 Hz), 7.15 (1H, d, J = 2.3 Hz), 7.21 (1H, d, J = 2.3 Hz), 7.64-8.02 (7H, m), 8.09 (1H, d, J = 8.9 Hz), 8.36 (1H, d, J = 2.5 Hz), 9.75 (1H, s), 10.53 (1H, s), 10.73 (1H, s) FAB+: 580 |
| 62 | 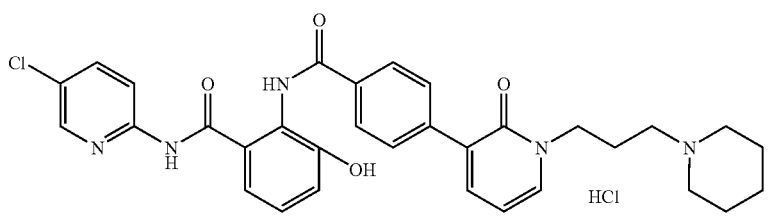 | ESI+: 586 |
| 63 | 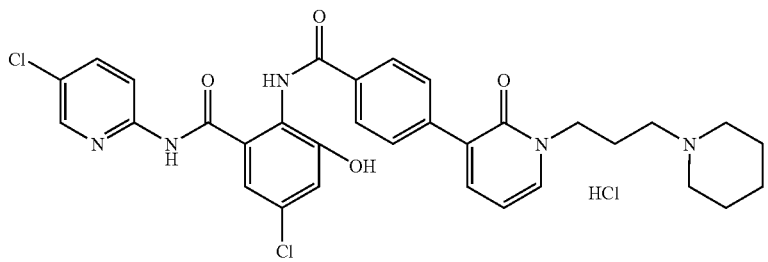 | ESI+: 620 |
| 64 | 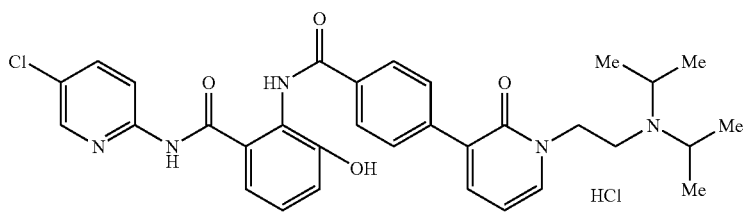 | ESI+: 588 |

TABLE 19-continued

| 65 | (structure) | FAB+: 622 |
| --- | --- | --- |
| 66 | (structure) | NMR (DMSO-d6): 1.86-2.01 (4H, m), 3.04-3.08 (2H, m), 3.51-3.62 (4H, m), 4.36-4.39 (2H, m), 6.46 (1H, t, J = 6.9 Hz), 7.13-7.16 (2H, m), 7.25 (1H, t, J = 7.9 Hz), 7.76-7.90 (5H, m), 7.95 (2H, d, J = 8.4 Hz), 8.13 (1H, d, 9.0 Hz), 8.34 (1H, d, J = 2.6 Hz), 9.77 (1H, s), 10.53 (1H, s), 10.68 (1H, bs) ESI+: 558 |

TABLE 20

| 67 | (structure) | NMR (DMSO-d6): 1.86-2.01 (4H, m), 3.06-3.09 (2H, m), 3.51-3.62 (4H, m), 4.34-4..37 (2H, m), 6.46 (1H, t, J = 6.9 Hz), 7.15 (1H, d, J = 2.4 Hz), 7.17 (1H, d, J = 2.4 Hz), 7.76 (1H, d, J = 2.0 Hz), 7.78 (1H, d, J = 2.0 Hz), 7.81-7.94 (5H, m), 8.08 (1H, d, J = 9.0 Hz), 8.36 (1H, d, J = 2.9 Hz), 9.73 (1H, s), 10.42 (1H, bs), 10.71 (1H, s) ESI+: 592 |
| --- | --- | --- |
| 68 | (structure) | NMR (DMSO-d6): 1.37-1.85 (6H, m), 2.92-2.99 (2H, m), 3.41-3.57 (4H, m), 4.38-4.42 (2H, m), 6.48 (1H, t, J = 6.8 Hz), 7.12-7.16 (2H, m), 7.25 (1H, t, J = 7.9 Hz), 7.77-7.90 (5H, m), 7.94 (2H, d, J = 8.4 Hz), 8.13 (1H, d, J = 9.1 Hz), 8.34 (1H, d, J = 2.4 Hz), 9.75 (1H, s), 9.93 (1H, bs), 10.52 (1H, s) ESI+: 572 |
| 69 | (structure) | NMR (DMSO-d6): 1.37-1.84 (6H, m), 2.92-2.99 (2H, m), 3.36-3.57 (4H, m), 4.39-4.42 (2H, m), 6.47 (1H, t, J = 6.9 Hz), 7.15 (1H, d, J = 2.2), 7.18 (1H, d, J = 2.4 Hz), 7.77 (1H, dd, J = 1.9, 7.0), 7.81-7.89 (4H, m), 7.93 (2H, d, J = 8.4 Hz), 8.09 (1H, d, J = 8.8 Hz), 8.35 (1H, d, 3.2 Hz), 9.73 (1H, s), 10.09 (1H, bs), 10.72 (1H, s) ESI+: 606 |
| 70 | (structure) | ESI+: 650 |

TABLE 20-continued
| 71 | 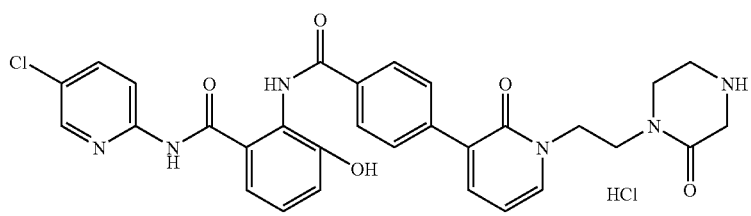 | ESI+: 587 |
| 72 | 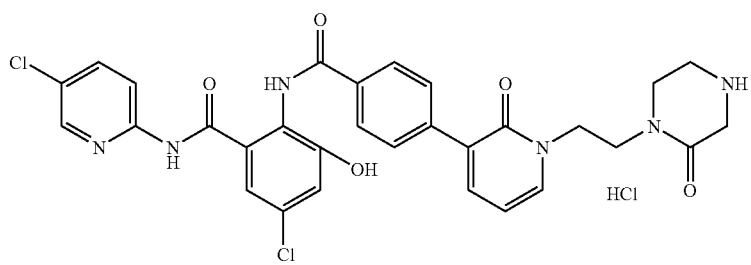 | ESI+: 621 |
TABLE 21
| 73 | 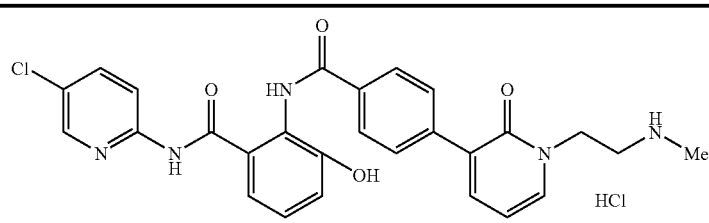 | NMR (DMSO-d6) 2.59 (3H, t, J = 2.8 Hz), 3.20-3.36 (2H, m), 4.30 (2H, t, J = 5.5 Hz), 6.46 (1H, t, J = 6.9 Hz), 7.09-7.19 (2H, m), 7.25 (1H, t, J = 7.9 Hz), 7.72-7.99 (7H, m), 8.12 (1H, d, J = 9.3 Hz), 8.35 (1H, d, J = 2.6 Hz), 8.76-8.97 (1H, m), 9.76 (1H, s), 10.49-10.58 (1H, m) FAB+: 518 |
| 74 | 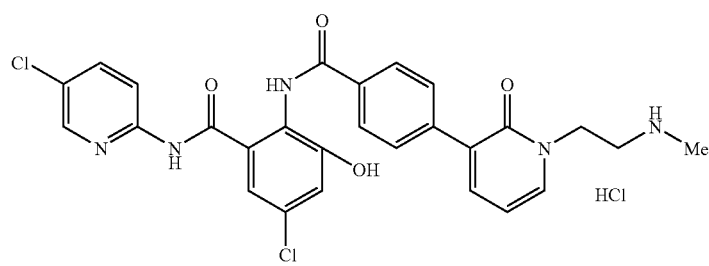 | NMR (DMSO-d6) 2.55-2.64 (3H, m), 3.24-3.36 (2H, m), 4.23-4.36 (2H, m), 6.46 (1H, t, J = 6.7 Hz), 7.10-7.22 (2H, m), 7.70-7.99 (7H, m), 8.08 (1H, d, J = 8.8 Hz), 8.36 (1H, d, J = 2.8 Hz), 8.67-8.93 (1H, m), 9.73 (1H, s), 10.51 (1H, s), 10.72 (1H, s) FAB+: 552 |
| 75 | 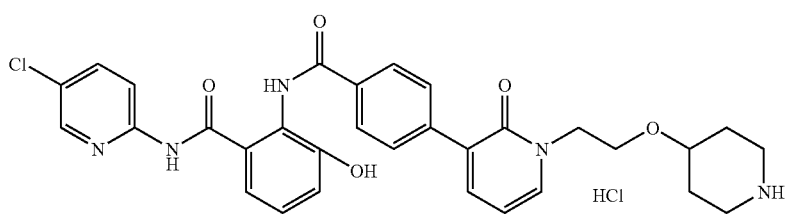 | ESI+: 588 |
| 76 | 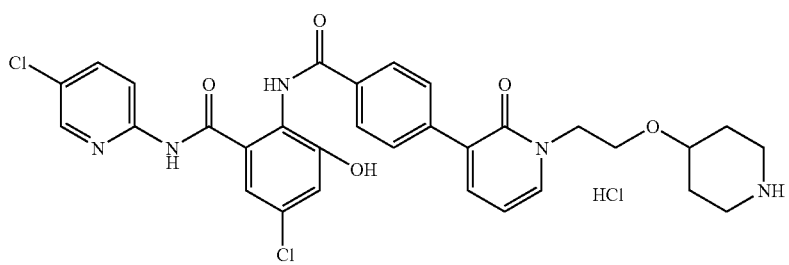 | ESI+: 622 |

TABLE 21-continued
| 77 | 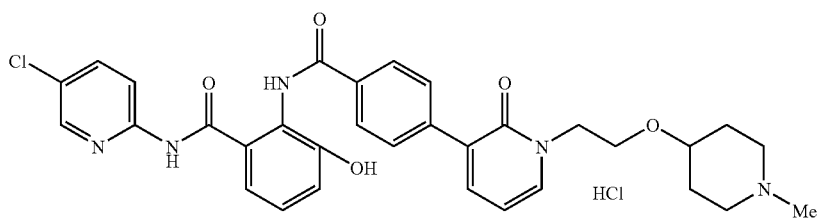 | ESI+: 602 |
|---|---|---|
| 78 | 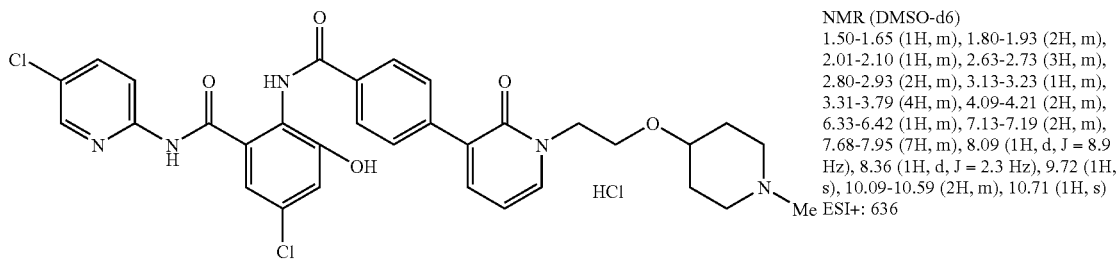 | NMR (DMSO-d6) 1.50-1.65 (1H, m), 1.80-1.93 (2H, m), 2.01-2.10 (1H, m), 2.63-2.73 (3H, m), 2.80-2.93 (2H, m), 3.13-3.23 (1H, m), 3.31-3.79 (4H, m), 4.09-4.21 (2H, m), 6.33-6.42 (1H, m), 7.13-7.19 (2H, m), 7.68-7.95 (7H, m), 8.09 (1H, d, J = 8.9 Hz), 8.36 (1H, d, J = 2.3 Hz), 9.72 (1H, s), 10.09-10.59 (2H, m), 10.71 (1H, s) ESI+: 636 |
TABLE 22
| 79 | 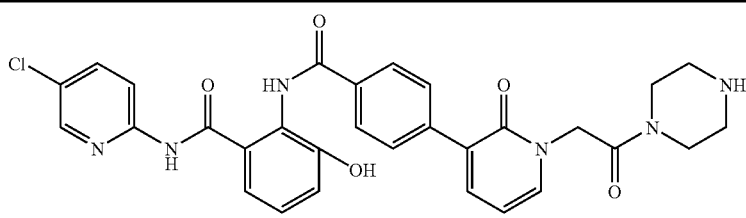 | FAB+: 587 |
|---|---|---|
| 80 | 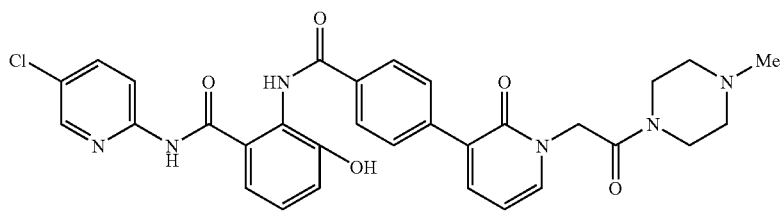 | ESI+: 601 |
| 81 | 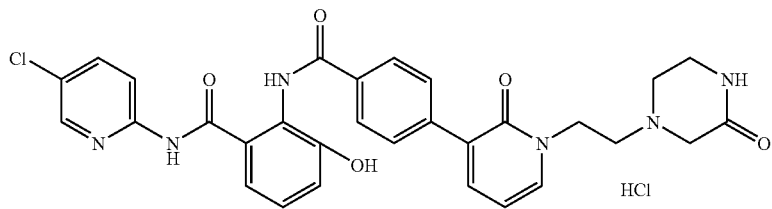 | ESI+: 587 |
| 82 | 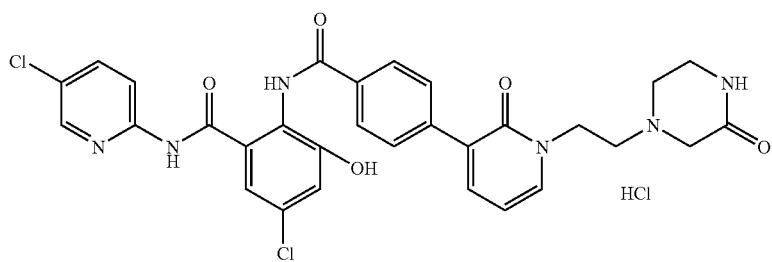 | ESI+: 621 |

TABLE 22-continued

| 83 | [structure] | NMR (DMSO-d6): 1.58-1.84 (2H, m), 1.88-2.06 (2H, m), 2.90-3.30 (2H, m), 3.30-4.00 (5H, m), 4.41 (2H, dd, J = 6.3, 12.8 Hz), 6.47 (1H, t, J = 6.9 Hz), 7.09-7.19 (2H, m), 7.25 (1H, t, J = 7.8 Hz), 7.77 (1H, dd, J = 1.9, 7.1 Hz), 7.80-7.91 (4H, m), 7.91-8.00 (2H, m), 8.13 (1H, d, J = 9.0 Hz), 8.34 (1H, d, J = 2.8 Hz), 9.76 (1H, s), 9.80-10.35 (1H, m), 10.53 (1H, s) ESI+: 588 |
| --- | --- | --- |
| 84 | [structure] | NMR (DMSO-d6): 1.54-1.84 (2H, m), 1.86-2.06 (2H, m), 2.90-3.30 (2H, m), 3.30-4.00 (5H, m), 4.40 (2H, dd, J = 6.2, 12.8 Hz), 6.47 (1H, t, J = 6.9 Hz), 7.15 (1H, d, J = 2.4 Hz), 7.18 (1H, d, J = 2.4 Hz), 7.72-8.00 (7H, m), 8.09 (1H, d, J = 8.9 Hz), 8.36 (1H, d, J = 2.4 Hz), 9.73 (1H, s), 9.90-10.66 (1H, m), 10.71 (1H, s) ESI+: 622 |
| 85 | [structure] | NMR (DMSO-d6) 1.62-1.92 (3H, m), 1.98-2.13 (1H, m), 3.17-3.48 (2H, m), 7.10 (1H, d, J = 7.8 Hz), 7.14 (1H, d, J = 7.8 Hz), 7.20-7.36 (3H, m), 7.66 (1H, s), 7.79-7.94 (3H, m), 8.13 (1H, d, J = 8.7 Hz), 8.34 (1H, d, J = 2.9 Hz), 9.67 (1H, s), 9.83 (1H, s), 10.51 (1H, s) FAB+: 465 |

TABLE 23

| 86 | [structure] | NMR (DMSO-d6): 1.64-1.88 (3H, m), 1.99-2.09 (1H, m), 3.18-3.34 (2H, m), 3.53-3.61 (1H, m), 7.08-7.17 (2H, m), 7.28 (2H, d, J = 8.3 Hz), 7.66 (1H, s), 7.82 (2H, d, J = 8.3 Hz), 7.87 (1H, dd, J = 8.9, 2.5 Hz), 8.09 (1H, d, J = 8.9 Hz), 8.35 (1H, d, J = 2.5 Hz), 9.62 (1H, s), 10.34 (1H, s), 10.69 (1H, s) FAB+: 499 |
| --- | --- | --- |
| 87 | [structure] | ESI+: 479 |
| 88 | [structure] | FAB+: 518 |

TABLE 23-continued

| | | |
|---|---|---|
| 89 | | NMR (DMSO-d6): 1.18-1.27 (6H, m), 1.76-2.12 (4H, m), 3.08-3.78 (11H, m), 7.08-7.17 (2H, m), 7.20-7.27 (1H, m), 7.31 (2H, d, J = 8.3 Hz), 7.81-7.90 (3H, m), 8.12 (1H, d, J = 9.0 Hz), 8.34 (1H, d, J = 2.4 Hz), 9.68 (1H, s), 9.80-9.96 (2H, m), 10.51 (1H, s) FAB+: 564 |
| 90 | | NMR (DMSO-d6): 1.19-1.27 (6H, m), 1.79-2.11 (4H, m), 3.06-3.77 (11H, m), 7.12-7.18 (2H, m), 7.31 (2H, d, J = 8.4 Hz), 7.83 (2H, d, J = 8.3 Hz), 7.87 (1H, dd, J = 8.9, 2.8 Hz), 8.08 (1H, d, J = 8.9 Hz), 8.35 (1H, d, J = 2.5 Hz), 9.65 (1H, s), 10.18 (1H, s), 10.47 (1H, s), 10.69 (1H, s) FAB+: 598 |
| 91 | | ESI+: 606 |

TABLE 24

| | | |
|---|---|---|
| 92 | | ESI+: 640 |
| 93 | | ESI+: 592 |
| 94 | | ESI+: 626 |

TABLE 24-continued
| 95 | 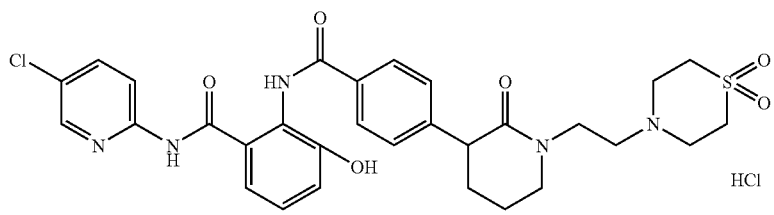 HCl | NMR (DMSO-d6) 1.74-2.14 (4H, m), 3.62-3.90 (15H, m), 7.13 (2H, dd, J = 4.6, 12.6 Hz), 7.24 (1H, t, J = 7.8 Hz), 7.35 (2H, d, J = 8.6 Hz), 7.78-7.96 (3H, m), 8.12 (1H, d, J = 8.1 Hz), 8.34 (1H, d, J = 2.9 Hz), 9.68 (1H, s), 10.49-10.54 (1H, m) ESI+: 626 |
| --- | --- | --- |
| 96 | 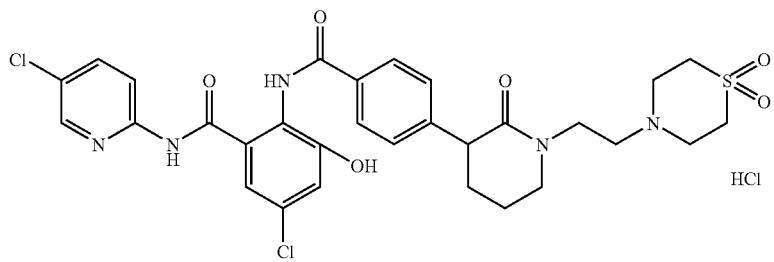 HCl | NMR (DMSO-d6) 1.71-2.17 (4H, m), 3.26-4.16 (15H, m), 7.15 (2H, s), 7.35 (2H, d, J = 8.6 Hz), 7.77-7.92 (3H, m), 8.09 (1H, d, J = 9.2 Hz), 8.36 (1H, d, J = 2.4 Hz), 9.64 (1H, s), 10.66-10.73 (1H, m) ESI+: 660 |
| 97 | 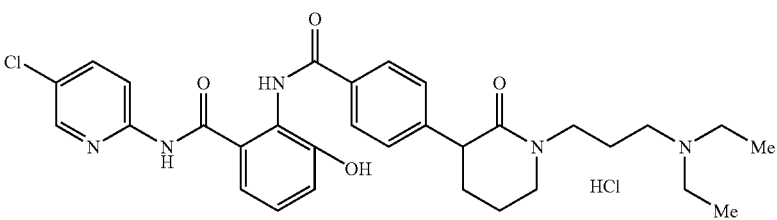 HCl | ESI+: 578 |
| 98 | 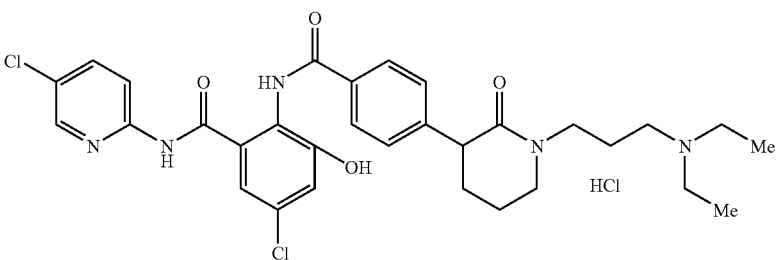 HCl | ESI+: 612 |
TABLE 25
| 99 | 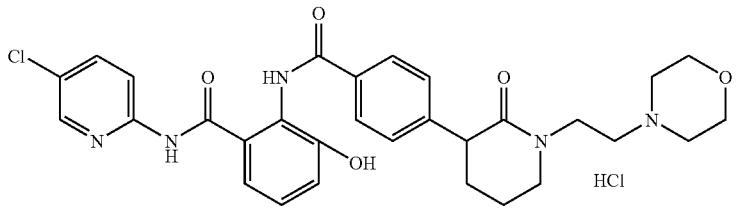 HCl | FAB+: 578 |
| --- | --- | --- |
| 100 | 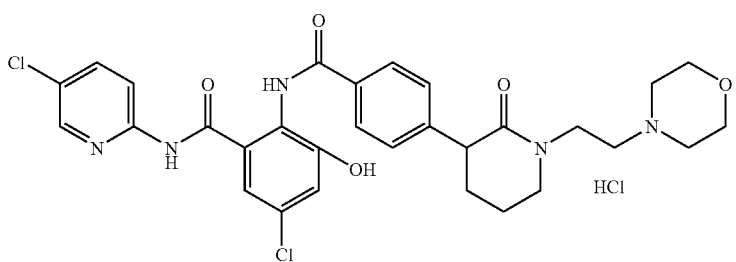 HCl | NMR (DMSO-d6): 1.80-2.12 (4H, m), 3.00-4.05 (15H, m), 7.14 (2H, s), 7.32 (2H, d, J = 8.2 Hz), 7.83 (2H, d, J = 8.2 Hz), 7.88 (1H, dd, J = 2.7, 9.0 Hz), 8.08 (1H, d, J = 9.0 Hz), 8.35 (1H, d, J = 2.7 Hz), 9.64 (1H, s), 10.43 (1H, s), 10.70 (2H, s) FAB+: 612 |

TABLE 25-continued
| 101 | 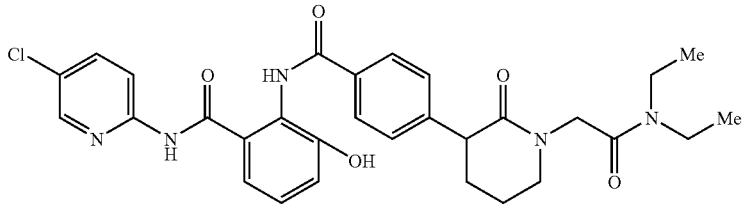 | ESI+: 578 |
| 102 | 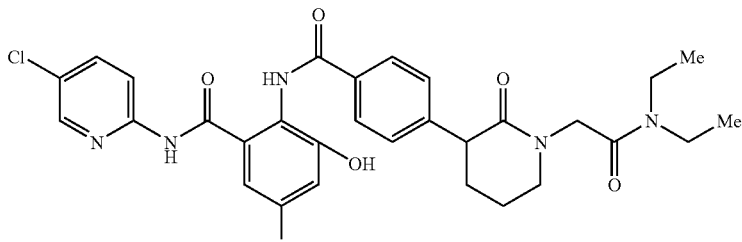 | ESI+: 612 |
| 103 | 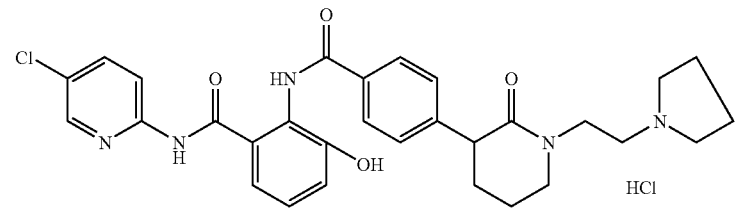 | ESI+: 562 |
| 104 | 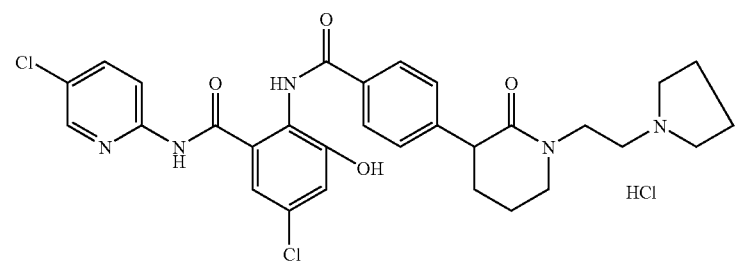 | ESI+: 596 |
| 105 | 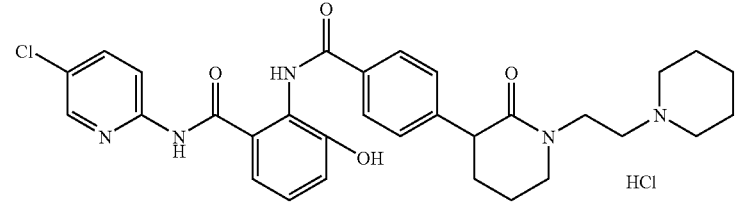 | NMR (DMSO-d6):<br>1.30-2.11 (10H, m), 2.82-2.97 (2H, m),<br>3.18-3.76 (9H, m), 7.09-7.17 (2H, m),<br>7.20-7.28 (1H, m), 7.32 (2H, d, J = 8.3 Hz), 7.81-7.91 (3H, m), 8.12 (1H, d, J = 9.0 Hz), 8.34 (1H, d, J = 2.5 Hz),<br>9.62-10.06 (3H, m), 10.51 (1H, s)<br>ESI+: 576 |
TABLE 26
| 106 | 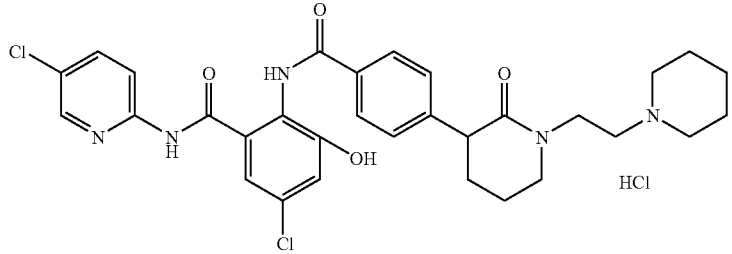 | NMR (DMSO-d6):<br>1.28-2.11 (10H, m), 2.82-2.95 (2H, m),<br>3.18-3.76 (9H, m), 7.12-7.18 (2H, m),<br>7.31 (2H, d, J = 8.3 Hz), 7.83 (2H, d, J = 8.3 Hz), 7.88 (1H, dd, J = 8.9, 2.7 Hz),<br>8.08 (1H, d, J = 8.9 Hz), 8.35 (1H, d, J = 2.5 Hz), 9.65 (1H, s), 10.07 (1H, s),<br>10.48 (1H, s), 10.70 (1H, s)<br>ESI+: 610 |

TABLE 26-continued

| # | Structure | Data |
|---|---|---|
| 107 | 5-chloropyridin-2-yl carbamoyl - 3-hydroxyphenyl - NH-C(O) - [4-(2-oxo-piperidin-3-yl)phenyl] with N-CH2CH2-N(iPr)2 · HCl | ESI+: 592 |
| 108 | 5-chloropyridin-2-yl carbamoyl - 3-hydroxy-5-chlorophenyl - NH-C(O) - [4-(2-oxo-piperidin-3-yl)phenyl] with N-CH2CH2-N(iPr)2 · HCl | ESI+: 626 |
| 109 | 5-chloropyridin-2-yl carbamoyl - 3-hydroxyphenyl - NH-C(O) - [4-(2-oxo-piperidin-3-yl)phenyl] with N-(CH2)3-piperidinyl · HCl | NMR (DMSO-d6): 1.28-1.46 (1H, m), 1.58-2.19 (11H, m), 2.74-3.04 (4H, m), 3.26-3.95 (7H, m), 7.09-7.18 (2H, m), 7.20-7.36 (3H, m), 7.79-7.95 (3H, m), 8.12 (1H, d, J = 9.0 Hz), 8.34 (1H, d, J = 2.6 Hz), 9.70 (1H, s), 10.10 (1H, s), 10.52 (1H, s) FAB+: 590 |
| 110 | 5-chloropyridin-2-yl carbamoyl - 3-hydroxy-5-chlorophenyl - NH-C(O) - [4-(2-oxo-piperidin-3-yl)phenyl] with N-(CH2)3-piperidinyl · HCl | NMR (DMSO-d6) 1.28-1.45 (1H, m), 1.62-2.11 (11H, m), 2.76-3.02 (4H, m), 3.28-3.88 (7H, m), 7.12-7.19 (2H, m), 7.29 (2H, d, J = 8.1 Hz), 7.78-7.94 (3H, m), 8.08 (1H, d, J = 8.4 Hz), 8.35 (1H, d, J = 2.9 Hz), 9.66 (1H, s), 9.91 (1H, s), 10.48 (1H, s), 10.66-10.73 (1H, m) FAB+: 624 |
| 111 | 5-chloropyridin-2-yl carbamoyl - 3-hydroxyphenyl - NH-C(O) - [4-(2-oxo-piperidin-3-yl)phenyl] with N-CH2CH2-piperazinyl · HCl | ESI+: 577 |
| 112 | 5-chloropyridin-2-yl carbamoyl - 3-hydroxy-5-chlorophenyl - NH-C(O) - [4-(2-oxo-piperidin-3-yl)phenyl] with N-CH2CH2-piperazinyl · HCl | ESI+: 611 |

TABLE 27

| | | |
|---|---|---|
| 113 | [structure] | ESI+: 576 |
| 114 | [structure] | ESI+: 610 |
| 115 | [structure] | NMR (DMSO-d6): 2.85 (3H, s), 2.87 (3H, s), 3.47-3.55 (2H, m), 4.39 (2H, t, J = 6.2 Hz), 7.11-7.18 (2H, m), 7.25 (1H, t, J = 7.9 Hz), 7.81-7.91 (3H, m), 7.98 (2H, d, J = 8.4 Hz), 8.12 (1H, d, J = 9.0 Hz), 8.28 (1H, s), 8.35 (1H, d, J = 2.8 Hz), 8.63 (1H, s), 9.74-10.05 (2H, m), 10.27 (1H, s), 10.54 (1H, s)<br>ESI+: 533 |
| 116 | [structure] | NMR (DMSO-d6) 3.26 (3H, s), 3.63 (2H, t, J = 5.3 Hz), 4.15 (2H, t, J = 5.3 Hz), 6.35 (1H, t, J = 6.9 Hz), 7.08-7.18 (2H, m), 7.25 (1H, t, J = 7.9 Hz), 7.68-7.74 (2H, m), 7.78-7.96 (5H, m), 8.14 (1H, d, J = 8.9 Hz), 8.35 (1H, d, J = 2.6 Hz), 9.75 (1H, s), 9.85 (1H, s), 10.53 (1H, s)<br>FAB+: 519 |
| 117 | [structure] | NMR (DMSO-d6) 2.01-2.10 (2H, m), 2.21-2.36 (2H, m), 2.78 (3H, d, J = 4.7 Hz), 3.15-3.29 (2H, m), 3.41-3.68 (2H, m), 4.99-5.13 (1H, m), 6.49 (1H, t, J = 6.9 Hz), 7.09-7.19 (2H, m), 7.25 (1H, t, J = 7.9 Hz), 7.59-7.66 (1H, m), 7.68-7.74 (1H, m), 7.80 (2H, d, J = 8.2 Hz), 7.85-7.97 (3H, m), 8.13 (1H, d, J = 8.9 Hz), 8.35 (1H, d, J = 2.6 Hz), 9.72-10.00 (2H, m), 10.50-10.68 (2H, m)<br>ESI+: 558 |

TABLE 28

| | | |
|---|---|---|
| 118 | [structure] | FAB+: 591 |

TABLE 28-continued

| 119 | 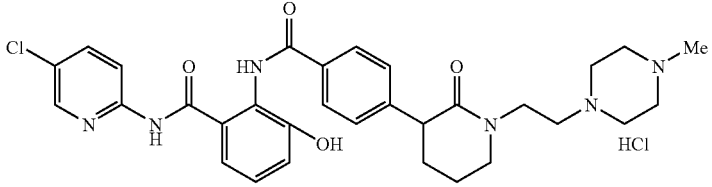 | ESI+: 591 |
|---|---|---|
| 120 | 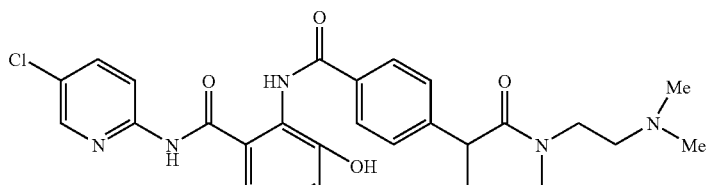 | HPLC condition<br>Column: CHIRALPAK AS-H<br>(0.46 cm(ID). × 25 cm(L))<br>Eluent: Hexane/Ethanol/Diethylamine =<br>50/50/0.1<br>Flow rate: 1.0 mL/min<br>Column temp: 40° C.<br>Detection: UV 254 nm<br>Retension time: 5.97 min |
| 121 | 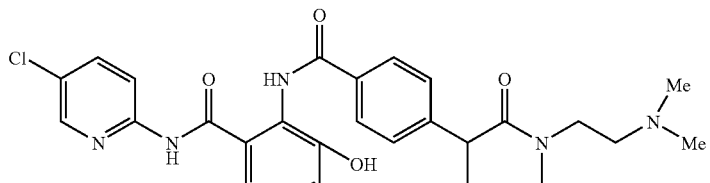 | HPLC condition<br>Column: CHIRALPAK AS-H<br>(0.46 cm(ID). × 25 cm(L))<br>Eluent: Hexane/Ethanol/Diethylamine =<br>50/50/0.1<br>Flow rate: 1.0 mL/min<br>Column temp: 40° C.<br>Detection: UV 254 nm<br>Retension time: 8.57 min |
| 122 | 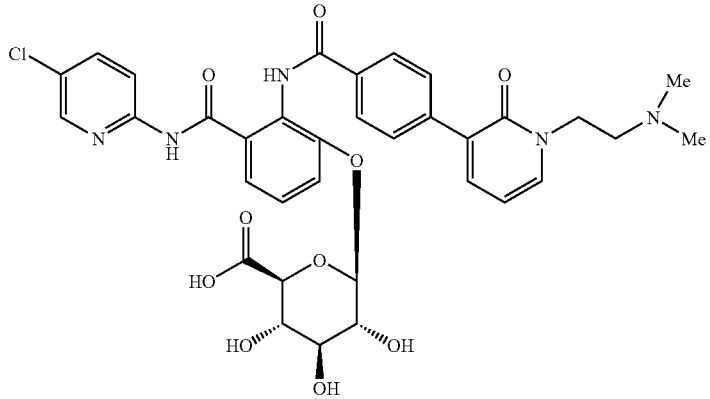 | NMR (DMSO-d6 + D$_2$O)<br>2.20 (6H, s), 2.57 (2H, t, J = 6.4 Hz), 3.18-<br>3.38 (3H, m), 3.51 (1H, d, J = 9.8 Hz), 4.07<br>(2H, t, J = 6.4 Hz), 4.88 (1H, d, J = 7.5 Hz),<br>6.39 (1H, t, J = 6.8 Hz), 7.32-7.50<br>(3H, m), 7.67-7.74 (2H, m), 7.80 (2H, d,<br>J = 8.4 Hz), 7.87 (1H, dd, J = 2.5,<br>9.0 Hz), 7.96 (2H, d, J = 8.4 Hz), 8.1 (1H, d,<br>J = 9.0), 8.3 (1H, d, J = 2.5 Hz)<br>ESI+: 708 |

TABLE 29

| 123 | 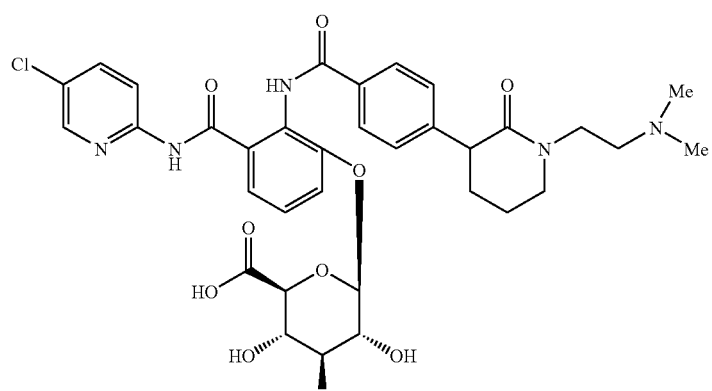 | NMR (DMSO-d6 + D$_2$O)<br>1.69-1.87 (3H, m), 1.96-2.11 (1H,<br>m), 2.48 (6H, s), 2.72-2.92 (2H,<br>m), 3.20-3.76 (9H, m), 4.91 (1H, d,<br>J = 7.6 Hz), 7.27 (2H, d, J =<br>8.2 Hz), 7.33-7.46 (3H, m), 7.80-<br>7.90 (3H, m), 8.10 (1H, d, J =<br>9.0 Hz), 8.31 (1H, d, J = 2.8 Hz)<br>ESI+: 712 |

TABLE 29-continued
| 124 | 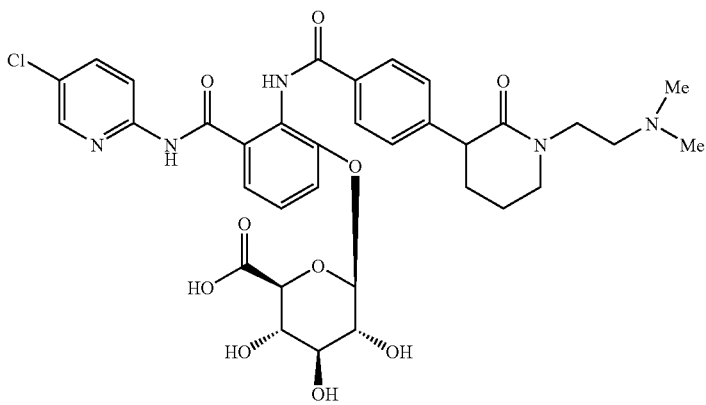 | NMR (DMSO-d6 + D₂O) 1.55-1.98 (3H, m), 2.00-2.11 (1H, m), 2.60 (6H, s), 2.90-3.06 (2H, m), 3.18-3.79 (9H, m), 4.92 (1H, d, J = 7.6 Hz), 7.30 (2H, d, J = 8.2 Hz), 7.34-7.45 (3H, m), 7.82-7.90 (3H, m), 8.10 (1H, d, J = 9.0 Hz), 8.31 (1H, d, J = 2.5 Hz) ESI+: 712 |
|---|---|---|
| 125 | 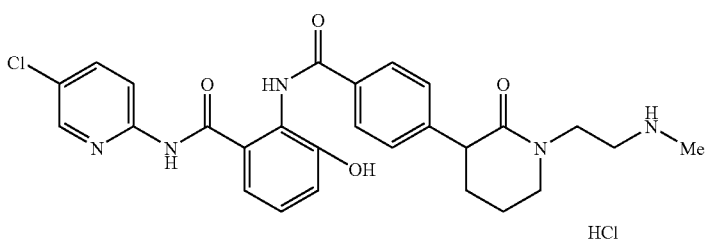 | NMR (DMSO-d6) 1.80-2.00 (3H, m), 2.01-2.13 (1H, m), 2.53-2.60 (3H, m), 3.01-3.19 (2H, m), 3.34-3.60 (3H, m), 3.63-3.77 (2H, m), 7.07-7.17 (2H, m), 7.24 (1H, t, J = 7.8 Hz), 7.33 (2H, d, J = 8.3 Hz), 7.79-7.93 (3H, m), 8.13 (1H, d, J = 8.9 Hz), 8.35 (1H, d, J = 2.4 Hz), 8.74 (2H, s), 9.70 (1H, s), 9.90 (1H, s), 10.53 (1H, s) ESI+: 522 |
| 126 | 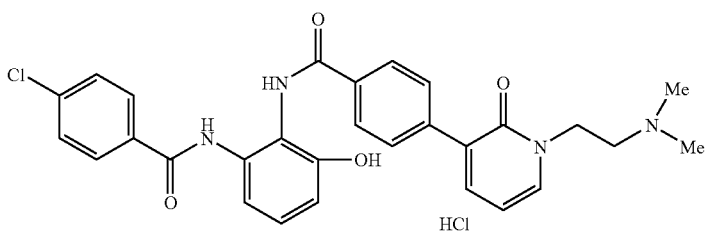 | ESI+: 531 |
| 127 | 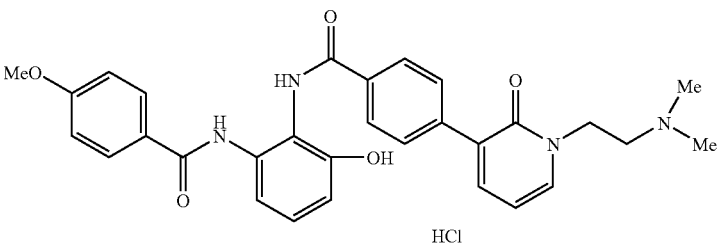 | NMR (DMSO-d6) 2.86 (6H, s), 3.46 (2H, t, J = 6.3 Hz), 3.81 (3H, s), 4.38 (2H, t, J = 6.3 Hz), 6.47 (1H, t, J = 6.9 Hz), 6.82 (1H, d, J = 7.8 Hz), 7.03 (2H, d, J = 8.8 Hz), 7.16 (1H, t, J = 8.1 Hz), 7.27 (1H, d, J = 7.9 Hz), 7.74-7.94 (6H, m), 8.04 (2H, d, J = 8.1 Hz), 9.65 (1H, s), 9.68 (1H, s), 9.80 (1H, s), 10.14 (1H, s) ESI+: 527 |
TABLE 30
| 128 | 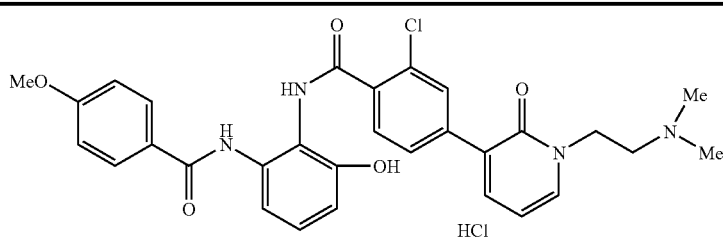 | FAB+: 561 |
|---|---|---|

TABLE 31
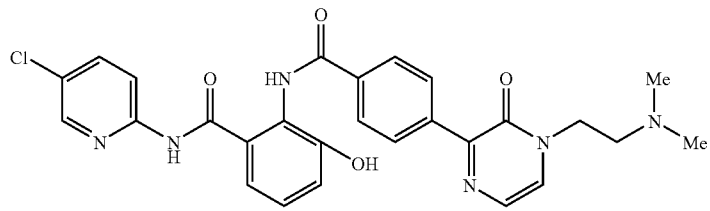
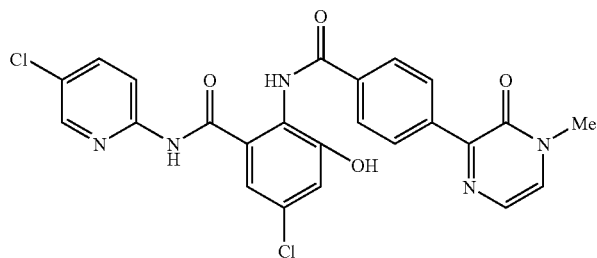
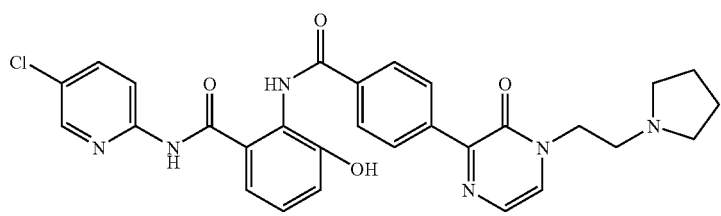
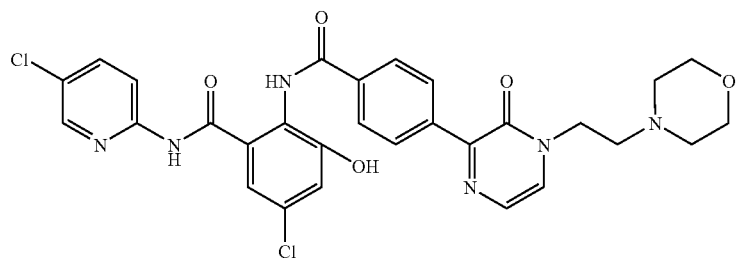
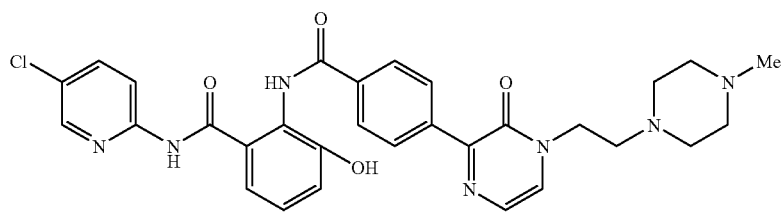
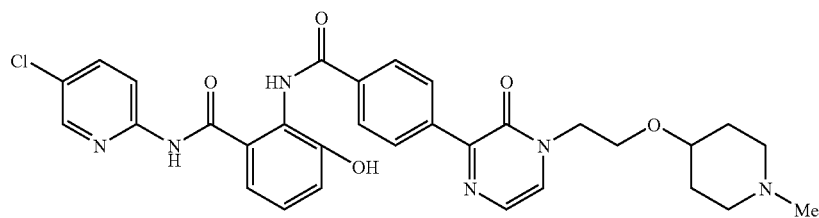

TABLE 31-continued
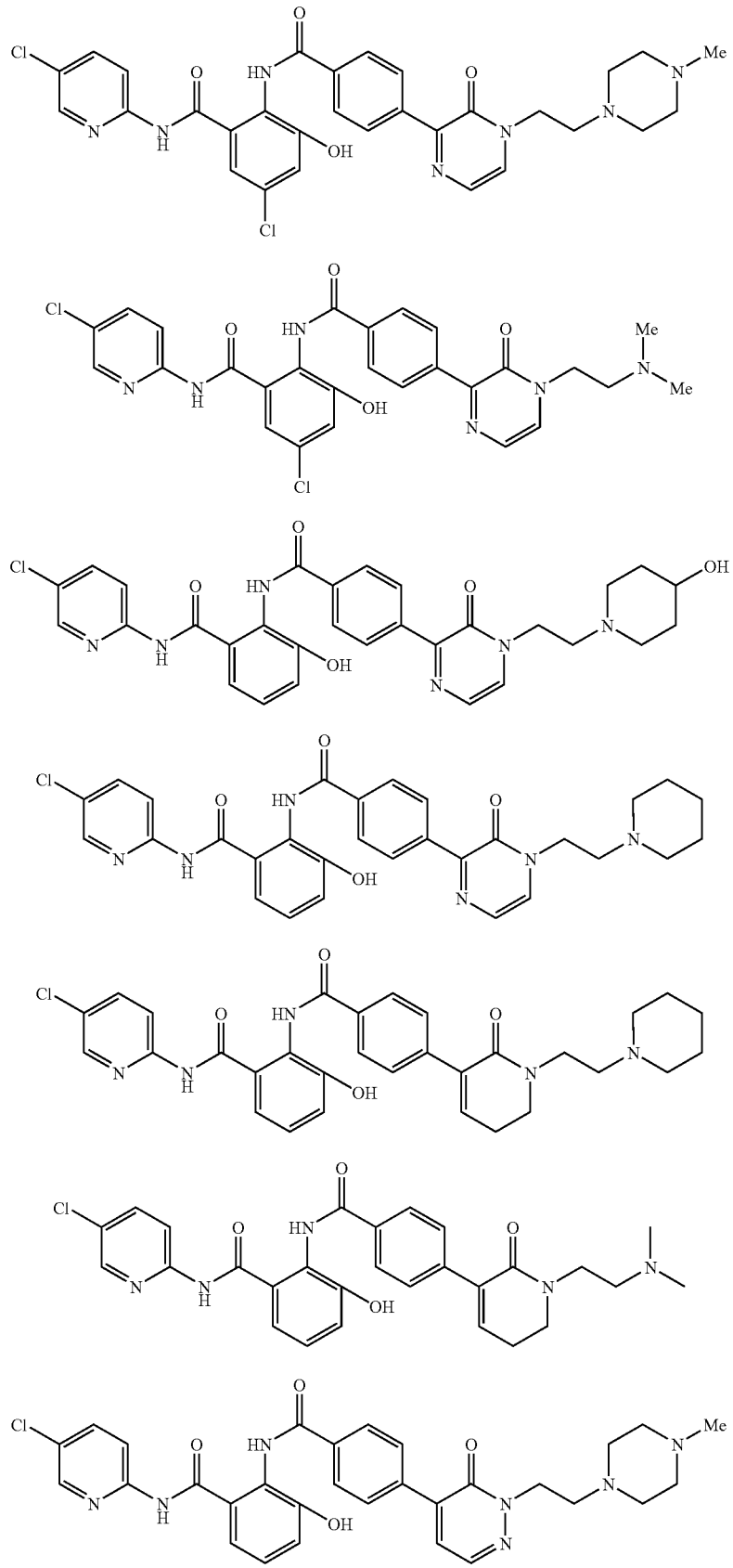

TABLE 31-continued
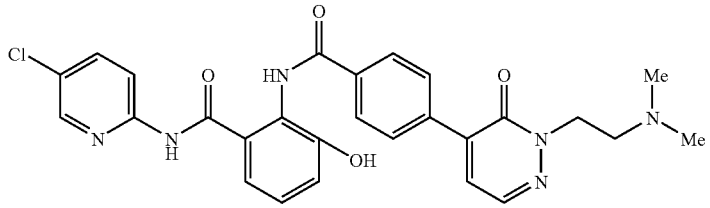
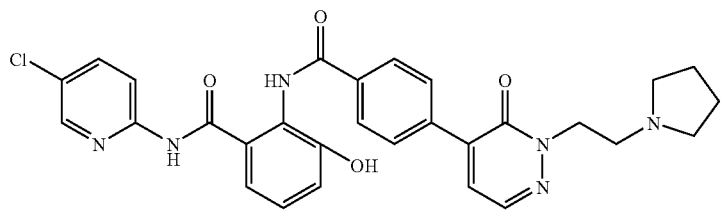
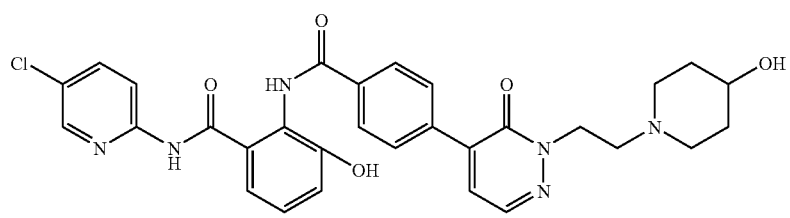
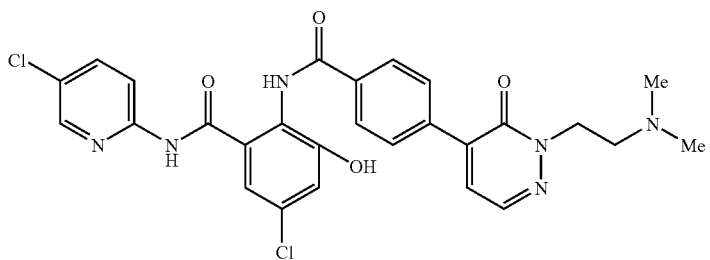
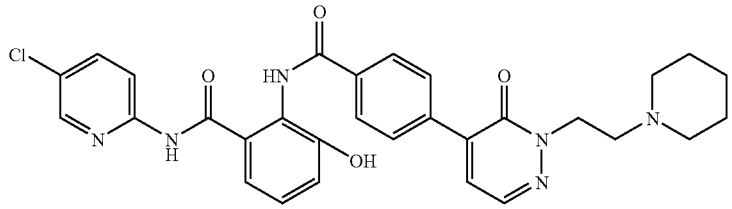
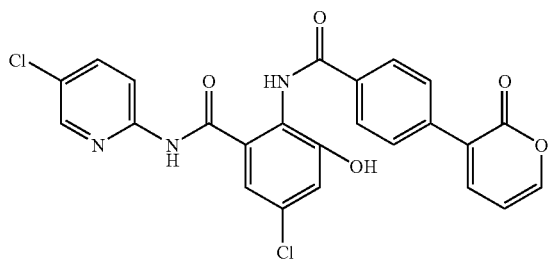

TABLE 31-continued
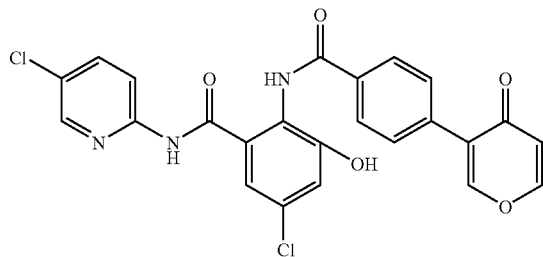
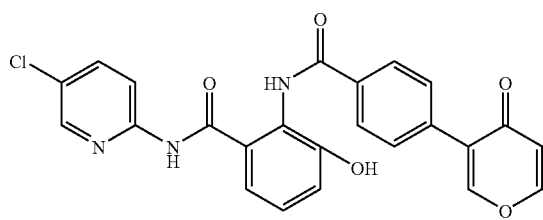
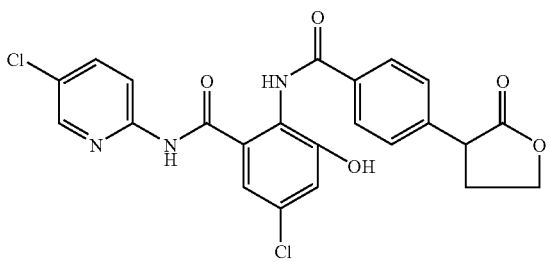
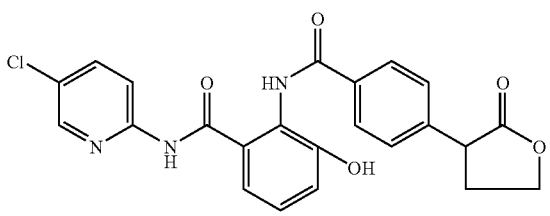
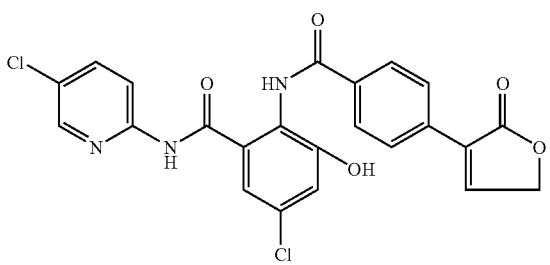
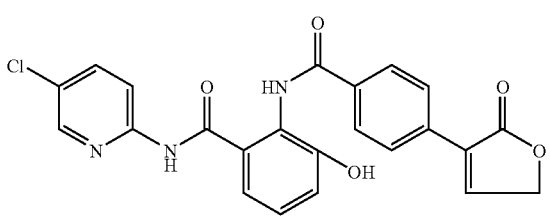

TABLE 31-continued
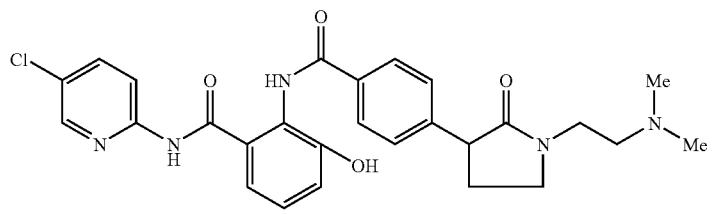
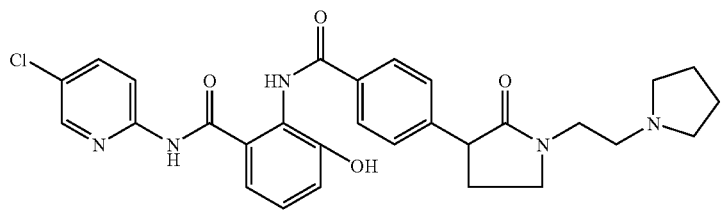
TABLE 32
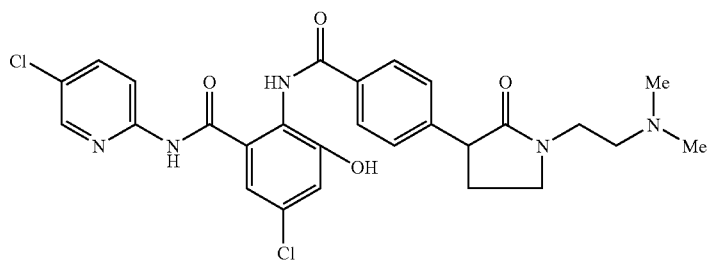
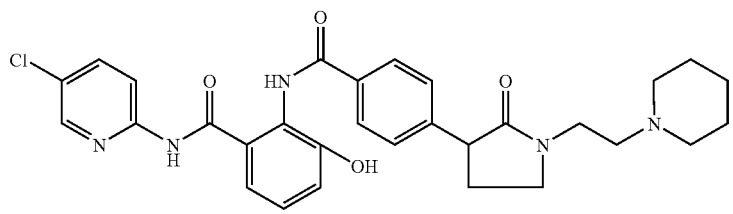
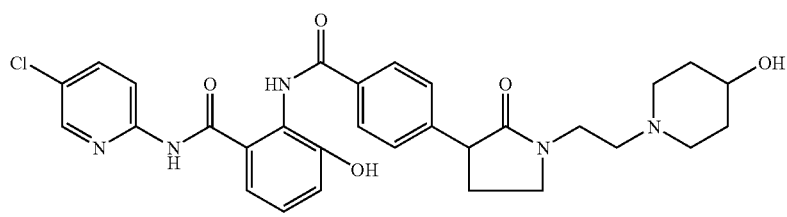
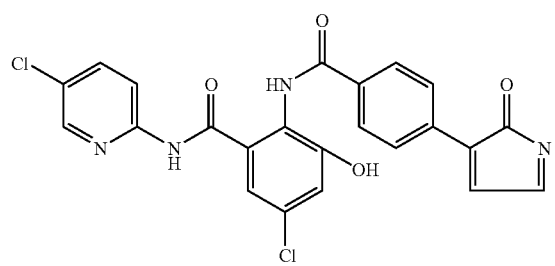

TABLE 32-continued
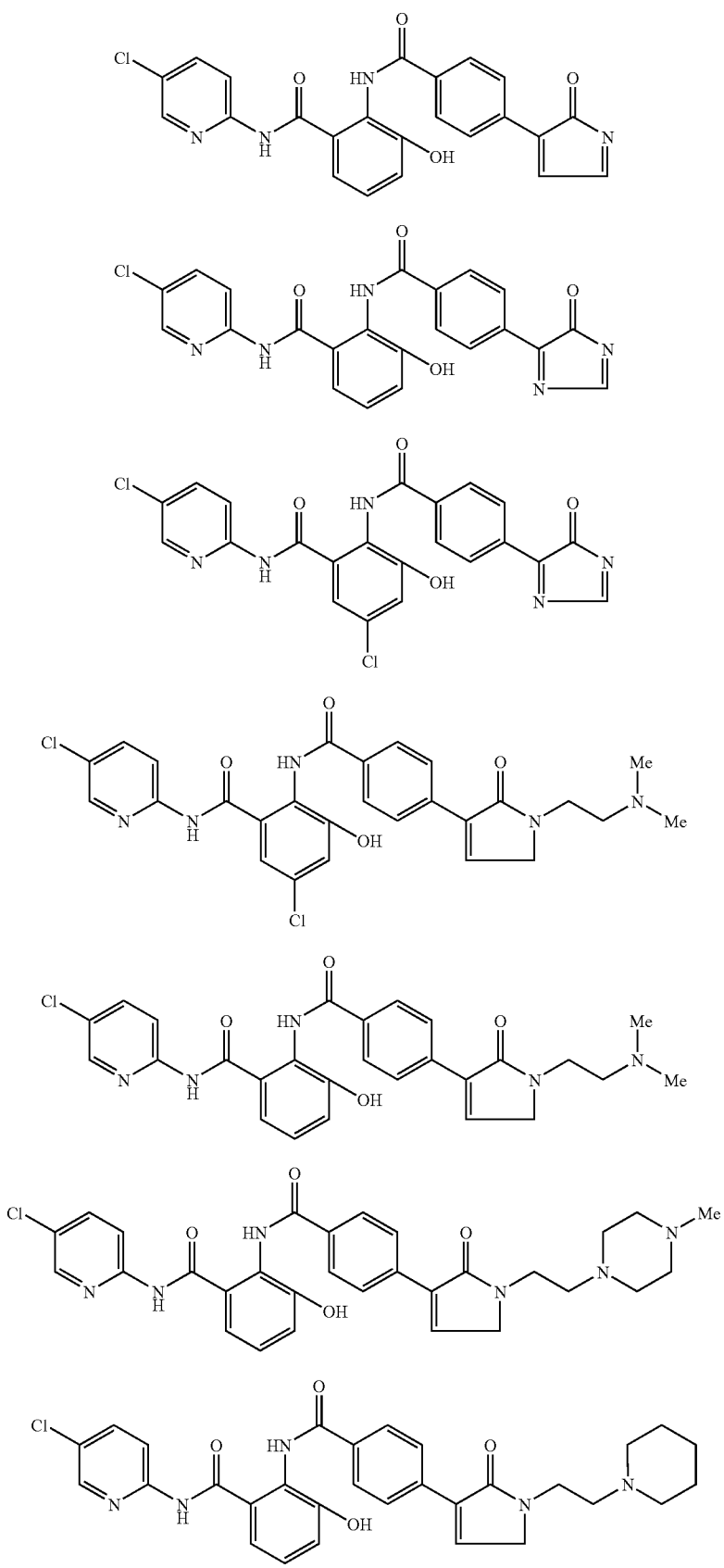

TABLE 32-continued
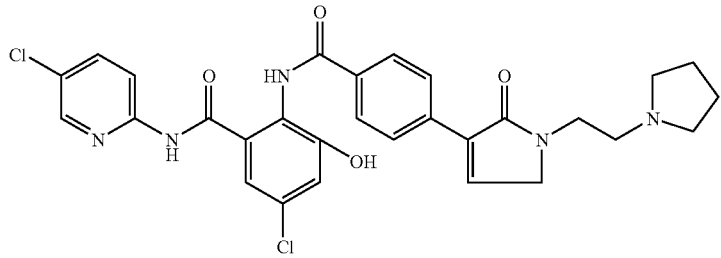
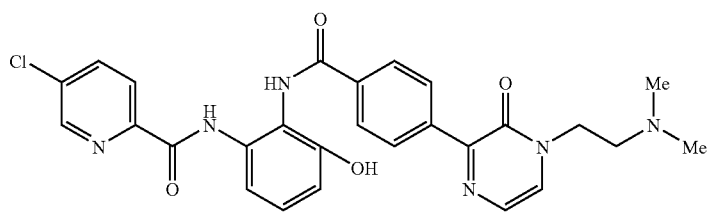
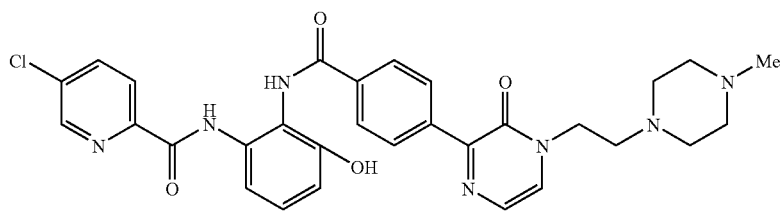
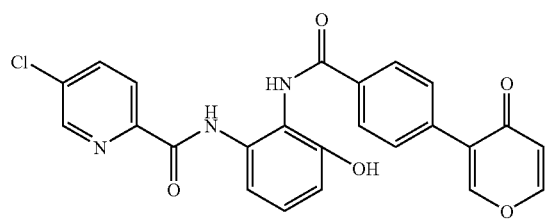
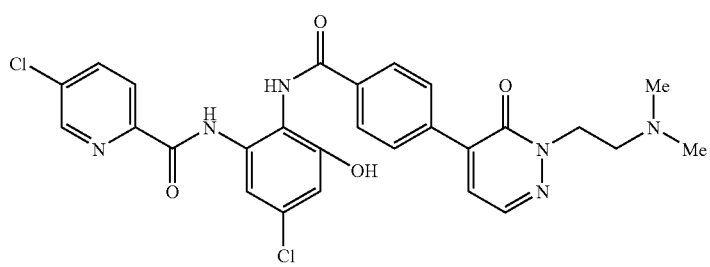
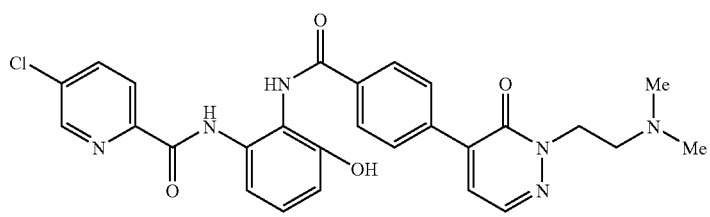

TABLE 32-continued
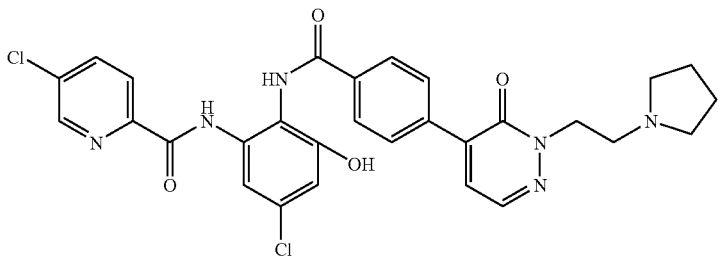
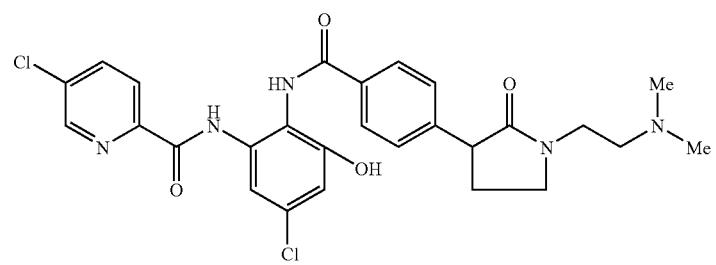
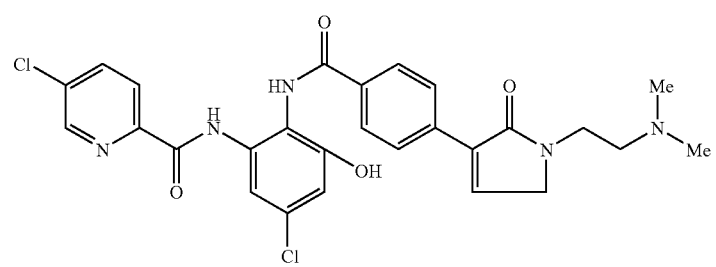
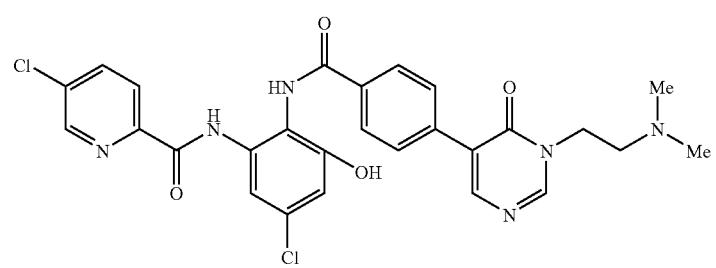
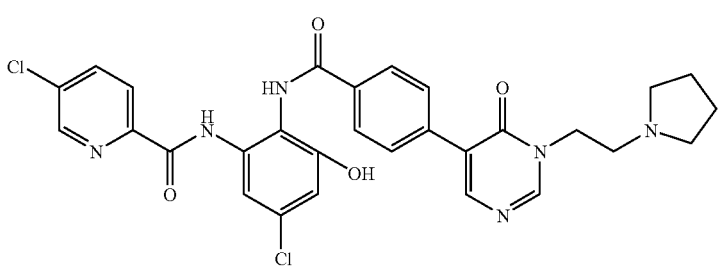
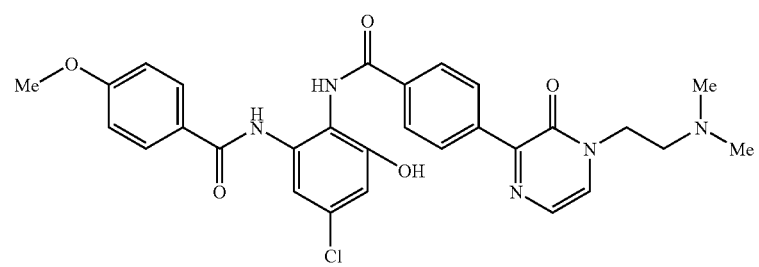

TABLE 32-continued

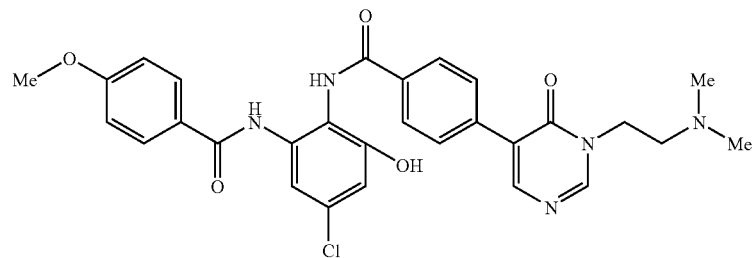

TABLE 33

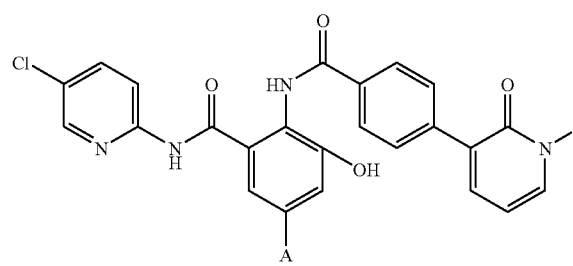

| No. | A | B |
|---|---|---|
| 1 | F | $CH_2CH_2N(Me)_2$ |
| 2 | H | $CH_2CH_2NH_2$ |
| 3 | Br | $CH_2CH_2N(Me)_2$ |
| 4 | F | $CH_2CH_2$—azetidinyl |
| 5 | Me | $CH_2CH_2N(Me)_2$ |
| 6 | Br | $CH_2CH_2$—azetidinyl |
| 7 | F | $CH_2CH_2NH(Me)$ |
| 8 | Me | $CH_2CH_2$—azetidinyl |
| 9 | Br | $CH_2CH_2NH(Me)$ |
| 10 | Cl | $CH_2CH_2$—azetidinyl |
| 11 | Me | $CH_2CH_2NH(Me)$ |
| 12 | H | $CH_2CH_2$—azetidinyl |
| 13 | F | $CH_2CH_2$—pyrrolidinyl |
| 14 | Cl | $CH_2CH_2CH_2$—azetidinyl |

TABLE 33-continued

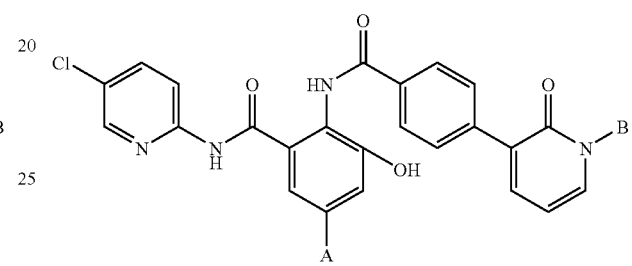

| No. | A | B |
|---|---|---|
| 15 | Br | $CH_2CH_2$—pyrrolidinyl |
| 16 | H | $CH_2CH_2CH_2$—azetidinyl |
| 17 | Me | $CH_2CH_2$—pyrrolidinyl |
| 18 | F | $CH_2CH_2CH_2$—pyrrolidinyl |
| 19 | F | $CH_2CH_2$—piperidinyl |
| 20 | Br | $CH_2CH_2CH_2$—pyrrolidinyl |
| 21 | Br | $CH_2CH_2$—piperidinyl |
| 22 | Me | $CH_2CH_2CH_2$—pyrrolidinyl |
| 23 | Me | $CH_2CH_2$—piperidinyl |

TABLE 33-continued

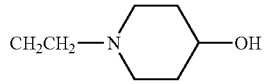

| No. | A | B |
|---|---|---|
| 24 | F | CH₂CH₂—N(piperidine-4-OH) |
| 25 | F | CH₂CH₂—N(piperazine-N'-Me) |
| 26 | Br | CH₂CH₂—N(piperidine-4-OH) |
| 27 | Br | CH₂CH₂—N(piperazine-N'-Me) |
| 28 | Me | CH₂CH₂—N(piperidine-4-OH) |
| 29 | Me | CH₂CH₂—N(piperazine-N'-Me) |
| 30 | F | CH₂CH₂—N(3-oxopiperazine-N'-Me) |
| 31 | F | CH₂CH₂—N(morpholine) |
| 32 | Br | CH₂CH₂—N(3-oxopiperazine-N'-Me) |
| 33 | Br | CH₂CH₂—N(morpholine) |
| 34 | Me | CH₂CH₂—N(3-oxopiperazine-N'-Me) |
| 35 | Me | CH₂CH₂—N(morpholine) |

TABLE 33-continued

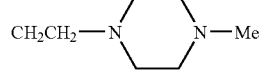

| No. | A | B |
|---|---|---|
| 36 | H | CH₂CH₂N(Me)₂ |
| 37 | Cl | CH₂CH₂NH₂ |
| 38 | Cl | CH₂CH₂N(Me)₂ |

TABLE 34

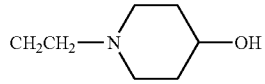

| No. | A | B |
|---|---|---|
| 39 | H | CH₂CH₂NH(Me) |
| 40 | Cl | CH₂CH₂—N(azetidine) |
| 41 | Cl | CH₂CH₂NH(Me) |
| 42 | H | CH₂CH₂CH₂—N(azetidine) |
| 43 | H | CH₂CH₂—N(pyrrolidine) |
| 44 | Cl | CH₂CH₂CH₂—N(azetidine) |
| 45 | Cl | CH₂CH₂—N(pyrrolidine) |
| 46 | H | CH₂CH₂CH₂—N(piperazine-N'-Me) |
| 47 | H | CH₂CH₂—N(piperidine) |

TABLE 34-continued

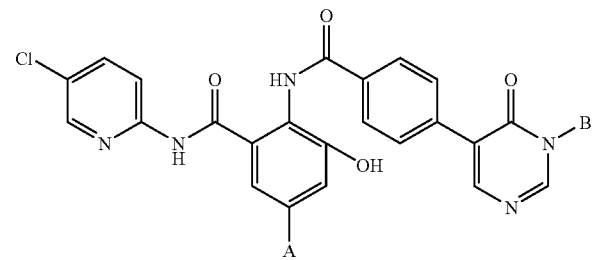

| No. | A | B |
|---|---|---|
| 48 | Cl | CH₂CH₂CH₂—N(piperazine)N—Me |
| 49 | Cl | CH₂CH₂—N(piperidine) |
| 50 | H | CH₂CH₂CH₂—N(pyrrolidine) |
| 51 | H | CH₂CH₂—N(piperazine)N—Me |
| 52 | Cl | CH₂CH₂CH₂—N(pyrrolidine) |
| 53 | Cl | CH₂CH₂—N(piperazine)N—Me |
| 54 | H | CH₂CH₂—N(piperidine)—OH |
| 55 | H | CH₂CH₂—N(morpholine) |
| 56 | Cl | CH₂CH₂—N(piperidine)—OH |
| 57 | Cl | CH₂CH₂—N(morpholine) |
| 58 | H | CH₂CH₂—N(piperazinone)N—Me |
| 59 | H | CH₂CH₂N(Et)₂ |
| 60 | Cl | CH₂CH₂—N(piperazinone)N—Me |

TABLE 34-continued

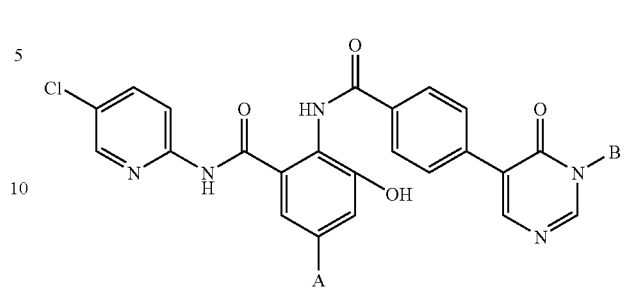

| No. | A | B |
|---|---|---|
| 61 | Cl | CH₂CH₂N(Et)₂ |
| 62 | F | CH₂CH₂N(Me)₂ |
| 63 | H | CH₂CH₂NH(Et) |
| 64 | Br | CH₂CH₂N(Me)₂ |
| 65 | Cl | CH₂CH₂NH(Et) |
| 66 | Me | CH₂CH₂N(Me)₂ |
| 67 | H | CH₂CH₂NH₂ |
| 68 | Cl | CH₂CH₂N(Me)₂ |
| 69 | Cl | CH₂CH₂NH₂ |
| 70 | H | CH₂CH₂—N(pyrrolidine) |
| 71 | H | CH₂CH₂—N(piperazine)N—Et |
| 72 | F | CH₂CH₂—N(pyrrolidine) |
| 73 | Cl | CH₂CH₂—N(piperazine)N—Et |
| 74 | Br | CH₂CH₂—N(pyrrolidine) |
| 75 | H | CH₂CH₂—N(azetidine) |
| 76 | Me | CH₂CH₂—N(pyrrolidine) |

TABLE 35

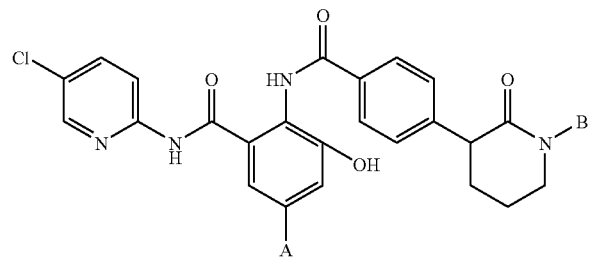

| No. | A | B |
|---|---|---|
| 77 | F | CH₂CH₂—piperidinyl |
| 78 | Cl | CH₂CH₂—N(piperidinyl)—OH |
| 79 | Br | CH₂CH₂—piperidinyl |
| 80 | H | CH₂CH₂—N(piperidinyl)—OH |
| 81 | Me | CH₂CH₂—piperidinyl |
| 82 | Me | CH₂CH₂—N(piperidinyl)—OH |
| 83 | H | CH₂CH₂—N-methylpiperazinyl |
| 84 | Cl | CH₂CH₂—N-methyl-3-oxopiperazinyl |
| 85 | Cl | CH₂CH₂—N-methylpiperazinyl |
| 86 | H | CH₂CH₂—N-methyl-3-oxopiperazinyl |
| 87 | F | CH₂CH₂—morpholinyl |
| 88 | Cl | CH₂CH₂CH₂—pyrrolidinyl |

TABLE 35-continued

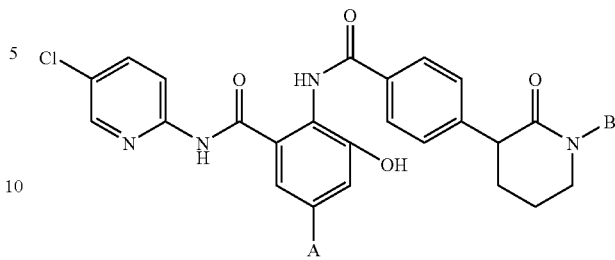

| No. | A | B |
|---|---|---|
| 89 | Br | CH₂CH₂—morpholinyl |
| 90 | H | CH₂CH₂CH₂—pyrrolidinyl |
| 91 | Me | CH₂CH₂—morpholinyl |
| 92 | Me | CH₂CH₂—N-methylpiperazinyl |
| 93 | Cl | CH₂CH₂NH₂ |
| 94 | Br | CH₂CH₂—N-methylpiperazinyl |
| 95 | H | CH₂CH₂NH₂ |
| 96 | F | CH₂CH₂—N-methylpiperazinyl |
| 97 | Cl | CH₂CH₂—azetidinyl |
| 98 | Me | CH₂CH₂—pyrrolidinyl |
| 99 | H | CH₂CH₂—azetidinyl |
| 100 | Br | CH₂CH₂—pyrrolidinyl |
| 101 | F | CH₂CH₂—azetidinyl |
| 102 | F | CH₂CH₂—pyrrolidinyl |
| 103 | Br | CH₂CH₂—azetidinyl |

TABLE 35-continued

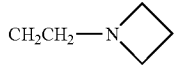

| No. | A | B |
|---|---|---|
| 104 | F | CH$_2$CH$_2$NH(Me) |
| 105 | Me | CH$_2$CH$_2$-N(azetidine) |
| 106 | Br | CH$_2$CH$_2$NH(Me) |
| 107 | Cl | CH$_2$CH$_2$CH$_2$-N(azetidine) |
| 108 | Me | CH$_2$CH$_2$NH(Me) |
| 109 | H | CH$_2$CH$_2$CH$_2$-N(azetidine) |
| 110 | F | CH$_2$CH$_2$NH$_2$ |
| 111 | Cl | CH$_2$CH$_2$CH$_2$-N(piperazine)N—Me |
| 112 | Br | CH$_2$CH$_2$NH$_2$ |
| 113 | H | CH$_2$CH$_2$CH$_2$-N(piperazine)N—Me |
| 114 | Me | CH$_2$CH$_2$NH$_2$ |

TABLE 36

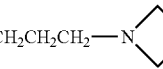

| No. | A | B |
|---|---|---|
| 115 | 4-Cl-phenyl (Me para) | CH$_2$CH$_2$-N(piperazine)N—Me |
| 116 | 3-Cl-6-Me-pyridazine | CH$_2$CH$_2$-N(morpholine) |
| 117 | 4-Cl-phenyl (Me) | CH$_2$CH$_2$N(Me)$_2$ |
| 118 | 4-MeO-phenyl (Me) | CH$_2$CH$_2$-N(piperazine)N—Me |
| 119 | 4-Cl-phenyl (Me) | CH$_2$CH$_2$-N(morpholine) |
| 120 | 4-MeO-phenyl (Me) | CH$_2$CH$_2$N(Me)$_2$ |
| 121 | 4-Br-phenyl (Me) | CH$_2$CH$_2$-N(piperazine)N—Me |
| 122 | 4-MeO-phenyl (Me) | CH$_2$CH$_2$-N(morpholine) |
| 123 | 4-Br-phenyl (Me) | CH$_2$CH$_2$N(Me)$_2$ |
| 124 | 4-MeO-3-F-phenyl (Me) | CH$_2$CH$_2$-N(piperazine)N—Me |
| 125 | 4-Br-phenyl (Me) | CH$_2$CH$_2$-N(morpholine) |
| 126 | 4-MeO-3-F-phenyl (Me) | CH$_2$CH$_2$N(Me)$_2$ |

TABLE 36-continued

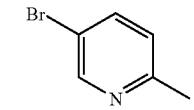

| No. | A | B |
|---|---|---|
| 127 | 5-bromo-2-methylpyridin-3-yl | CH₂CH₂-(4-methylpiperazin-1-yl) |
| 128 | 2-methoxy-6-fluoro-4-methylphenyl | CH₂CH₂-morpholin-4-yl |
| 129 | 5-bromo-2-methylpyridin-3-yl | CH₂CH₂N(Me)₂ |
| 130 | 4-fluoro-2-methylphenyl | CH₂CH₂-(4-methylpiperazin-1-yl) |
| 131 | 5-bromo-2-methylpyridin-3-yl | CH₂CH₂-morpholin-4-yl |
| 132 | 4-fluoro-2-methylphenyl | CH₂CH₂N(Me)₂ |
| 133 | 5-chloro-2-methylthien-3-yl | CH₂CH₂-(4-methylpiperazin-1-yl) |
| 134 | 4-fluoro-2-methylphenyl | CH₂CH₂-morpholin-4-yl |
| 135 | 5-chloro-2-methylthien-3-yl | CH₂CH₂N(Me)₂ |
| 136 | 5-chloro-2-methylpyrimidin-4-yl | CH₂CH₂-(4-methylpiperazin-1-yl) |
| 137 | 5-chloro-2-methylthien-3-yl | CH₂CH₂-morpholin-4-yl |

TABLE 36-continued

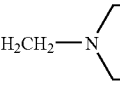

| No. | A | B |
|---|---|---|
| 138 | 5-chloro-2-methylpyrimidin-4-yl | CH₂CH₂N(Me)₂ |
| 139 | 5-bromo-2-methylthien-3-yl | CH₂CH₂-(4-methylpiperazin-1-yl) |
| 140 | 5-chloro-2-methylpyrimidin-4-yl | CH₂CH₂-morpholin-4-yl |
| 141 | 5-bromo-2-methylthien-3-yl | CH₂CH₂N(Me)₂ |
| 142 | 5-chloro-2-methyloxazol-4-yl | CH₂CH₂-(4-methylpiperazin-1-yl) |
| 143 | 5-bromo-2-methylthien-3-yl | CH₂CH₂-morpholin-4-yl |
| 144 | 5-chloro-2-methyloxazol-4-yl | CH₂CH₂N(Me)₂ |
| 145 | 5-chloro-2-methylthiazol-4-yl | CH₂CH₂-(4-methylpiperazin-1-yl) |
| 146 | 5-chloro-2-methyloxazol-4-yl | CH₂CH₂-morpholin-4-yl |
| 147 | 5-chloro-2-methylthiazol-4-yl | CH₂CH₂N(Me)₂ |
| 148 | 5-methoxy-2-methylpyridin-3-yl | CH₂CH₂-(4-methylpiperazin-1-yl) |
| 149 | 5-chloro-2-methylthiazol-4-yl | CH₂CH₂-morpholin-4-yl |

TABLE 36-continued

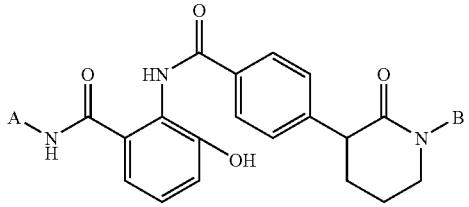

| No. | A | B |
|---|---|---|
| 150 | 5-methoxy-2-methylpyridin-3-yl | CH₂CH₂N(Me)₂ |
| 151 | 6-chloro-3-methylpyridazin-4-yl | CH₂CH₂—N(piperazinyl)—Me |
| 152 | 5-methoxy-2-methylpyridin-3-yl | CH₂CH₂—N(morpholinyl) |
| 153 | 6-chloro-3-methylpyridazin-4-yl | CH₂CH₂N(Me)₂ |
| 154 | 5-methoxy-2-methylpyridin-3-yl | CH₂CH₂CH₂N(Me)₂ |

TABLE 37

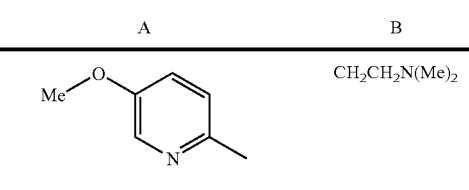

| No. | A | B |
|---|---|---|
| 155 | 4-chloro-3-methylphenyl | CH₂CH₂—N(piperazinyl)—Me |
| 156 | 6-chloro-3-methylpyridazin-4-yl | CH₂CH₂—N(morpholinyl) |
| 157 | 4-chloro-3-methylphenyl | CH₂CH₂N(Me)₂ |
| 158 | 4-methoxy-3-methylphenyl | CH₂CH₂—N(piperazinyl)—Me |
| 159 | 4-chloro-3-methylphenyl | CH₂CH₂—N(morpholinyl) |
| 160 | 4-methoxy-3-methylphenyl | CH₂CH₂N(Me)₂ |
| 161 | 4-bromo-3-methylphenyl | CH₂CH₂—N(piperazinyl)—Me |
| 162 | 4-methoxy-3-methylphenyl | CH₂CH₂—N(morpholinyl) |
| 163 | 4-bromo-3-methylphenyl | CH₂CH₂N(Me)₂ |
| 164 | 4-methoxy-3-fluoro-5-methylphenyl | CH₂CH₂—N(piperazinyl)—Me |
| 165 | 4-bromo-3-methylphenyl | CH₂CH₂—N(morpholinyl) |
| 166 | 4-methoxy-3-fluoro-5-methylphenyl | CH₂CH₂N(Me)₂ |
| 167 | 5-bromo-2-methylpyridin-3-yl | CH₂CH₂—N(piperazinyl)—Me |
| 168 | 4-methoxy-3-fluoro-5-methylphenyl | CH₂CH₂—N(morpholinyl) |

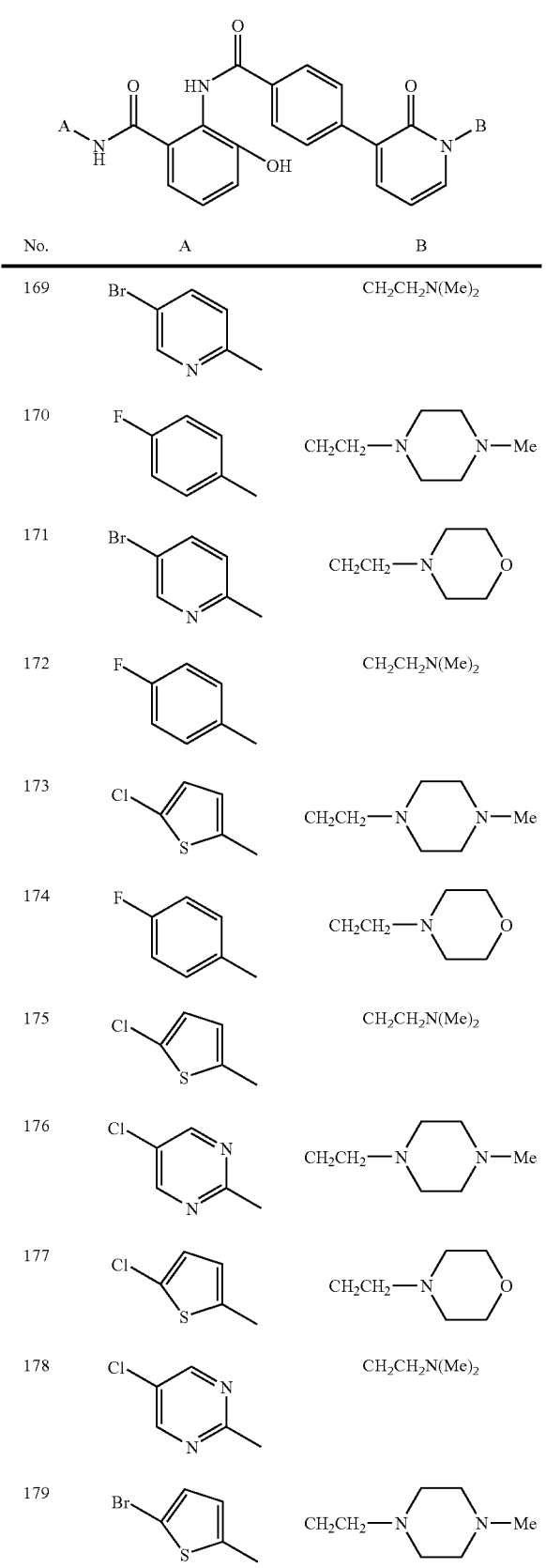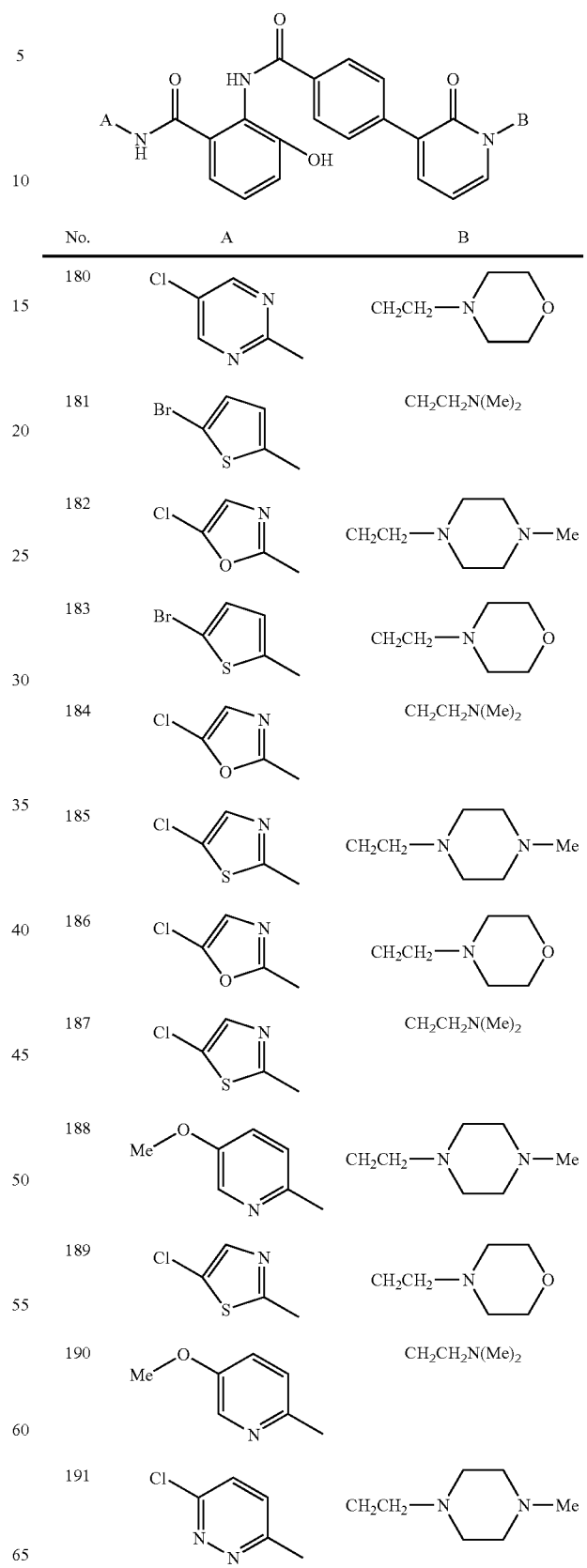

TABLE 37-continued

[Structure: A-NH-C(=O)-phenyl(OH)-NH-C(=O)-phenyl-pyridinone-N-B]

| No. | A | B |
|-----|---|---|
| 192 | 5-methoxy-2-methylpyridin-yl | CH₂CH₂-morpholino |
| 193 | 6-chloro-3-methylpyridazin-yl | CH₂CH₂N(Me)₂ |
| 194 | 5-methoxy-2-methylpyridin-yl | CH₂CH₂CH₂N(Me)₂ |

TABLE 38

[Structure: A-C(=O)-NH-phenyl(OH)-NH-C(=O)-phenyl-pyridinone-N-B]

| No. | A | B |
|-----|---|---|
| 195 | 4-chlorophenyl | CH₂CH₂-(4-methylpiperazin-1-yl) |
| 196 | 6-chloro-3-methylpyridazin-yl | CH₂CH₂-pyrrolidin-1-yl |
| 197 | 4-chlorophenyl | CH₂CH₂N(Et)₂ |
| 198 | 4-methoxyphenyl | CH₂CH₂-(4-methylpiperazin-1-yl) |
| 199 | 4-chloro-phenyl (methyl) | CH₂CH₂-pyrrolidin-1-yl |

TABLE 38-continued

| No. | A | B |
|-----|---|---|
| 200 | 4-methoxyphenyl | CH₂CH₂N(Et)₂ |
| 201 | 4-bromophenyl | CH₂CH₂-(4-methylpiperazin-1-yl) |
| 202 | 4-methoxyphenyl | CH₂CH₂-pyrrolidin-1-yl |
| 203 | 4-bromophenyl | CH₂CH₂N(Me)₂ |
| 204 | 4-methoxy-3-fluorophenyl | CH₂CH₂-(4-methylpiperazin-1-yl) |
| 205 | 4-bromophenyl | CH₂CH₂-pyrrolidin-1-yl |
| 206 | 4-methoxy-3-fluorophenyl | CH₂CH₂N(Me)₂ |
| 207 | 5-bromo-2-methylpyridin-yl | CH₂CH₂-(4-methylpiperazin-1-yl) |
| 208 | 4-methoxy-3-fluorophenyl | CH₂CH₂-pyrrolidin-1-yl |
| 209 | 5-bromo-2-methylpyridin-yl | CH₂CH₂N(Me)₂ |
| 210 | 4-fluorophenyl | CH₂CH₂-(4-methylpiperazin-1-yl) |

TABLE 38-continued

Structure (left, Nos. 211–222 and right, Nos. 223–233):

A-C(=O)-NH-[phenyl(OH)]-NH-C(=O)-[phenyl]-[2-oxo-pyridin-3-yl]-N-B

| No. | A | B |
|---|---|---|
| 211 | 5-bromo-2-methylpyridin-3-yl | CH₂CH₂-(pyrrolidin-1-yl) |
| 212 | 4-fluoro-3-methylphenyl | CH₂CH₂N(Me)₂ |
| 213 | 5-chloro-2-methylthiophen-3-yl | CH₂CH₂-(4-methylpiperazin-1-yl) |
| 214 | 4-fluoro-3-methylphenyl | CH₂CH₂-(pyrrolidin-1-yl) |
| 215 | 5-chloro-2-methylthiophen-3-yl | CH₂CH₂N(Me)₂ |
| 216 | 5-chloro-2-methylpyrimidin-4-yl | CH₂CH₂-(4-methylpiperazin-1-yl) |
| 217 | 5-chloro-2-methylthiophen-3-yl | CH₂CH₂-(pyrrolidin-1-yl) |
| 218 | 5-chloro-2-methylpyrimidin-4-yl | CH₂CH₂N(Me)₂ |
| 219 | 5-bromo-2-methylthiophen-3-yl | CH₂CH₂-(4-methylpiperazin-1-yl) |
| 220 | 5-chloro-2-methylpyrimidin-4-yl | CH₂CH₂-(pyrrolidin-1-yl) |
| 221 | 5-bromo-2-methylthiophen-3-yl | CH₂CH₂N(Me)₂ |
| 222 | 5-chloro-2-methyloxazol-4-yl | CH₂CH₂-(4-methylpiperazin-1-yl) |
| 223 | 5-bromo-2-methylthiophen-3-yl | CH₂CH₂-(pyrrolidin-1-yl) |
| 224 | 5-chloro-2-methyloxazol-4-yl | CH₂CH₂N(Me)₂ |
| 225 | 5-chloro-2-methylthiazol-4-yl | CH₂CH₂-(4-methylpiperazin-1-yl) |
| 226 | 5-chloro-2-methyloxazol-4-yl | CH₂CH₂-(pyrrolidin-1-yl) |
| 227 | 5-chloro-2-methylthiazol-4-yl | CH₂CH₂N(Me)₂ |
| 228 | 5-methoxy-2-methylpyridin-3-yl | CH₂CH₂-(4-methylpiperazin-1-yl) |
| 229 | 5-chloro-2-methylthiazol-4-yl | CH₂CH₂-(pyrrolidin-1-yl) |
| 230 | 5-methoxy-2-methylpyridin-3-yl | CH₂CH₂N(Me)₂ |
| 231 | 6-chloro-3-methylpyridazin-4-yl | CH₂CH₂-(4-methylpiperazin-1-yl) |
| 232 | 5-methoxy-2-methylpyridin-3-yl | CH₂CH₂-(pyrrolidin-1-yl) |
| 233 | 6-chloro-3-methylpyridazin-4-yl | CH₂CH₂N(Me)₂ |

TABLE 38-continued

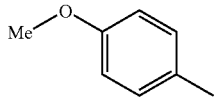

| No. | A | B |
|---|---|---|
| 234 | 4-MeO-C6H4- | CH2CH2-piperidinyl |

TABLE 39

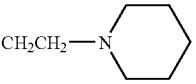

| No. | A | B |
|---|---|---|
| 235 | 4-Cl-C6H4- | CH2CH2-N(4-Me-piperazinyl) |
| 236 | 6-Cl-pyridazin-3-yl | CH2CH2-pyrrolidinyl |
| 237 | 4-Cl-C6H4- | CH2CH2N(Me)2 |
| 238 | 4-MeO-C6H4- | CH2CH2-N(4-Me-piperazinyl) |
| 239 | 4-Cl-C6H4- | CH2CH2-pyrrolidinyl |
| 240 | 4-MeO-C6H4- | CH2CH2N(Me)2 |

TABLE 39-continued

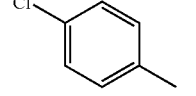

| No. | A | B |
|---|---|---|
| 241 | 4-Br-C6H4- | CH2CH2-N(4-Me-piperazinyl) |
| 242 | 4-MeO-C6H4- | CH2CH2-pyrrolidinyl |
| 243 | 4-Br-C6H4- | CH2CH2N(Me)2 |
| 244 | 4-MeO-3-F-C6H3- | CH2CH2-N(4-Me-piperazinyl) |
| 245 | C6H5- | CH2CH2-pyrrolidinyl |
| 246 | 4-MeO-3-F-C6H3- | CH2CH2N(Me)2 |
| 247 | 6-Me-pyridin-3-yl (5-Br) | CH2CH2-N(4-Me-piperazinyl) |
| 248 | 4-MeO-3-F-C6H3- | CH2CH2-pyrrolidinyl |
| 249 | 6-Me-pyridin-3-yl (5-Br) | CH2CH2N(Me)2 |
| 250 | 4-F-C6H4- | CH2CH2-N(4-Me-piperazinyl) |
| 251 | 6-Me-pyridin-3-yl (5-Br) | CH2CH2-pyrrolidinyl |

TABLE 39-continued

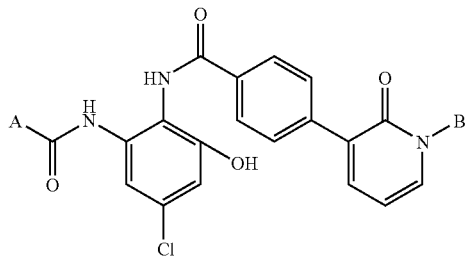

| No. | A | B |
|---|---|---|
| 252 | 4-F-phenyl | CH₂CH₂N(Me)₂ |
| 253 | 5-Cl-2-thienyl | CH₂CH₂-N(piperazine)-N-Me |
| 254 | 4-F-phenyl | CH₂CH₂-N(pyrrolidine) |
| 255 | 5-Cl-2-thienyl | CH₂CH₂N(Me)₂ |
| 256 | 5-Cl-2-methylpyrimidin | CH₂CH₂-N(piperazine)-N-Me |
| 257 | 5-Cl-2-thienyl | CH₂CH₂-N(pyrrolidine) |
| 258 | 5-Cl-2-methylpyrimidin | CH₂CH₂N(Me)₂ |
| 259 | 5-Br-2-thienyl | CH₂CH₂-N(piperazine)-N-Me |
| 260 | 5-Cl-2-methylpyrimidin | CH₂CH₂-N(pyrrolidine) |
| 261 | 5-Br-2-thienyl | CH₂CH₂N(Me)₂ |
| 262 | 5-Cl-2-methyloxazol | CH₂CH₂-N(piperazine)-N-Me |
| 263 | 5-Br-2-methylthienyl | CH₂CH₂-N(pyrrolidine) |
| 264 | 5-Cl-2-methyloxazol | CH₂CH₂N(Me)₂ |
| 265 | 5-Cl-2-methylthiazol | CH₂CH₂-N(piperazine)-N-Me |
| 266 | 5-Cl-2-methyloxazol | CH₂CH₂-N(pyrrolidine) |
| 267 | CH₂CH₂-N(piperazine)-N-Me | CH₂CH₂N(Me)₂ |
| 268 | 5-MeO-2-methylpyridyl | CH₂CH₂-N(piperazine)-N-Me |
| 269 | 5-Cl-2-methylthiazol | CH₂CH₂-N(pyrrolidine) |
| 270 | 5-MeO-2-methylpyridyl | CH₂CH₂N(Me)₂ |
| 271 | 6-Cl-3-methylpyridazin | CH₂CH₂-N(piperazine)-N-Me |
| 272 | 5-MeO-2-methylpyridyl | CH₂CH₂-N(pyrrolidine) |
| 273 | 6-Cl-3-methylpyridazin | CH₂CH₂N(Me)₂ |

TABLE 39-continued

Structure: A-NH-C(O)- attached to benzene ring with -OH and -Cl substituents, NH-C(O)-phenyl-pyridinone-B

| No. | A | B |
|-----|---|---|
| 274 | 4-MeO-C6H4- | CH2CH2-piperidinyl |

TABLE 40

Structure: A-NH-C(O)- attached to benzene ring with -OH, NH-C(O)-phenyl-piperidinone-B

| No. | A | B |
|-----|---|---|
| 275 | 4-Cl-C6H4- | CH2CH2-N(4-methylpiperazinyl) |
| 276 | 6-Cl-3-methylpyridazin-yl | CH2CH2-pyrrolidinyl |
| 277 | 4-Cl-C6H4- | CH2CH2N(Me)2 |
| 278 | 4-MeO-C6H4- | CH2CH2-N(4-methylpiperazinyl) |
| 279 | 4-Cl-C6H4- | CH2CH2-pyrrolidinyl |
| 280 | 4-MeO-C6H4- | CH2CH2N(Me)2 |
| 281 | 4-Br-C6H4- | CH2CH2-N(4-methylpiperazinyl) |

TABLE 40-continued

| No. | A | B |
|-----|---|---|
| 282 | 4-MeO-C6H4- | CH2CH2-pyrrolidinyl |
| 283 | 4-Br-C6H4- | CH2CH2N(Me)2 |
| 284 | 4-MeO-3-F-C6H3- | CH2CH2-N(4-methylpiperazinyl) |
| 285 | 4-Br-C6H4- | CH2CH2-pyrrolidinyl |
| 286 | 4-MeO-3-F-C6H3- | CH2CH2N(Me)2 |
| 287 | 5-Br-2-methylpyridin-yl | CH2CH2-N(4-methylpiperazinyl) |
| 288 | 4-MeO-3-F-C6H3- | CH2CH2-pyrrolidinyl |
| 289 | 5-Br-2-methylpyridin-yl | CH2CH2N(Me)2 |
| 290 | 4-F-C6H4- | CH2CH2-N(4-methylpiperazinyl) |
| 291 | 5-Br-2-methylpyridin-yl | CH2CH2-pyrrolidinyl |
| 292 | 4-F-C6H4- | CH2CH2N(Me)2 |

TABLE 40-continued

[Structure: A-C(=O)-NH- on benzene with OH, connected via -NH-C(=O)- to phenyl-piperidinone-N-B]

| No. | A | B |
|-----|---|---|
| 293 | 5-chloro-2-thienyl | CH₂CH₂-(4-methylpiperazin-1-yl) |
| 294 | 4-fluorophenyl | CH₂CH₂-pyrrolidin-1-yl |
| 295 | 5-chloro-2-thienyl | CH₂CH₂N(Me)₂ |
| 296 | 5-chloropyrimidin-2-yl | CH₂CH₂-(4-methylpiperazin-1-yl) |
| 297 | 5-chloro-2-thienyl | CH₂CH₂-pyrrolidin-1-yl |
| 298 | 5-chloropyrimidin-2-yl | CH₂CH₂N(Me)₂ |
| 299 | 5-bromo-2-thienyl | CH₂CH₂-(4-methylpiperazin-1-yl) |
| 300 | 5-chloropyrimidin-2-yl | CH₂CH₂-pyrrolidin-1-yl |
| 301 | 5-bromo-2-thienyl | CH₂CH₂N(Me)₂ |
| 302 | 5-chloro-2-oxazolyl | CH₂CH₂-(4-methylpiperazin-1-yl) |
| 303 | 5-bromo-2-thienyl | CH₂CH₂-pyrrolidin-1-yl |
| 304 | 5-chloro-2-oxazolyl | CH₂CH₂N(Me)₂ |

TABLE 40-continued

[Structure: pyridine variant with A-C(=O)-NH- and OH, connected via -NH-C(=O)- to phenyl-piperidinone-N-B]

| No. | A | B |
|-----|---|---|
| 305 | 5-chloro-2-thiazolyl | CH₂CH₂-(4-methylpiperazin-1-yl) |
| 306 | 5-chloro-2-oxazolyl | CH₂CH₂-pyrrolidin-1-yl |
| 307 | 5-chloro-2-thiazolyl | CH₂CH₂N(Me)₂ |
| 308 | 5-methoxy-2-methylpyridin-? (5-methoxy-pyridin-2-yl) | CH₂CH₂-(4-methylpiperazin-1-yl) |
| 309 | 5-chloro-2-thiazolyl | CH₂CH₂-pyrrolidin-1-yl |
| 340 | 5-methoxy-pyridin-2-yl | CH₂CH₂N(Me)₂ |
| 310 | 6-chloropyridazin-3-yl | CH₂CH₂-(4-methylpiperazin-1-yl) |
| 312 | 5-methoxy-pyridin-2-yl | CH₂CH₂-pyrrolidin-1-yl |
| 313 | 6-chloropyridazin-3-yl | CH₂CH₂N(Me)₂ |
| 314 | 4-methoxyphenyl | CH₂CH₂-piperidin-1-yl |

TABLE 41

| No. | A | B |
|---|---|---|
| 315 | 4-Cl-phenyl | CH2CH2-(4-methylpiperazin-1-yl) |
| 316 | 6-Cl-pyridazin-3-yl | CH2CH2-(pyrrolidin-1-yl) |
| 317 | 4-Cl-phenyl | CH2CH2N(Me)2 |
| 318 | 4-MeO-phenyl | CH2CH2-(4-methylpiperazin-1-yl) |
| 319 | 4-Cl-phenyl | CH2CH2-(pyrrolidin-1-yl) |
| 320 | 4-MeO-phenyl | CH2CH2N(Me)2 |
| 321 | 4-Br-phenyl | CH2CH2-(4-methylpiperazin-1-yl) |
| 322 | 4-MeO-phenyl | CH2CH2-(pyrrolidin-1-yl) |
| 323 | 4-Br-phenyl | CH2CH2N(Me)2 |
| 324 | 4-MeO-3-F-phenyl | CH2CH2-(4-methylpiperazin-1-yl) |
| 325 | 4-Br-phenyl | CH2CH2-(pyrrolidin-1-yl) |
| 326 | 4-MeO-3-F-phenyl | CH2CH2N(Me)2 |
| 327 | 5-Br-6-methylpyridin-2-yl | CH2CH2-(4-methylpiperazin-1-yl) |
| 328 | 4-MeO-3-F-phenyl | CH2CH2-(pyrrolidin-1-yl) |
| 329 | 5-Br-6-methylpyridin-2-yl | CH2CH2N(Me)2 |
| 330 | 4-F-phenyl | CH2CH2-(4-methylpiperazin-1-yl) |
| 331 | 5-Br-6-methylpyridin-2-yl | CH2CH2-(pyrrolidin-1-yl) |
| 332 | 4-F-phenyl | CH2CH2N(Me)2 |
| 333 | 5-Cl-2-methylthien-2-yl | CH2CH2-(4-methylpiperazin-1-yl) |
| 334 | 4-F-phenyl | CH2CH2-(pyrrolidin-1-yl) |
| 335 | 5-Cl-2-methylthien-2-yl | CH2CH2N(Me)2 |
| 336 | 5-Cl-2-methylpyrimidin-5-yl | CH2CH2-(4-methylpiperazin-1-yl) |

TABLE 41-continued

[Structure shown: A-NH-C(=O)- attached to benzene ring with OH and Cl substituents, connected via NH-C(=O) to phenyl-piperidinone-N-B]

| No. | A | B |
|---|---|---|
| 337 | 5-Cl-thiophen-2-yl (methyl) | CH₂CH₂-pyrrolidinyl |
| 338 | 5-Cl-pyrimidin-2-yl (methyl) | CH₂CH₂N(Me)₂ |
| 339 | 5-Br-thiophen-2-yl (methyl) | CH₂CH₂-N(4-Me-piperazinyl) |
| 340 | 5-Cl-pyrimidin-2-yl (methyl) | CH₂CH₂-pyrrolidinyl |
| 341 | 5-Br-thiophen-2-yl (methyl) | CH₂CH₂N(Me)₂ |
| 342 | 5-Cl-oxazol-2-yl (methyl) | CH₂CH₂-N(4-Me-piperazinyl) |
| 343 | 5-Br-thiophen-2-yl (methyl) | CH₂CH₂-pyrrolidinyl |
| 344 | 5-Cl-oxazol-2-yl (methyl) | CH₂CH₂N(Me)₂ |
| 345 | 5-Cl-thiazol-2-yl (methyl) | CH₂CH₂-N(4-Me-piperazinyl) |
| 346 | 5-Cl-oxazol-2-yl (methyl) | CH₂CH₂-pyrrolidinyl |
| 347 | 5-Cl-thiazol-2-yl (methyl) | CH₂CH₂N(Me)₂ |

TABLE 41-continued

[Same core structure as above]

| No. | A | B |
|---|---|---|
| 348 | 5-MeO-6-methylpyridin-2-yl | CH₂CH₂-N(4-Me-piperazinyl) |
| 349 | 5-Cl-thiazol-2-yl (methyl) | CH₂CH₂-pyrrolidinyl |
| 350 | 5-MeO-6-methylpyridin-2-yl | CH₂CH₂N(Me)₂ |
| 351 | 6-Cl-3-methylpyridazin-3-yl | CH₂CH₂-N(4-Me-piperazinyl) |
| 352 | 5-MeO-6-methylpyridin-2-yl | CH₂CH₂-pyrrolidinyl |
| 353 | 6-Cl-3-methylpyridazin-3-yl | CH₂CH₂N(Me)₂ |
| 354 | 4-MeO-3-methylphenyl | CH₂CH₂-piperidinyl |

TABLE 42

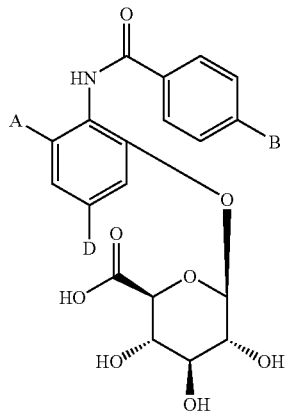

| No | A | B | D |
|---|---|---|---|
| 355 | 5-Cl-pyridin-2-yl-NHC(O)CH₃ | 3-methyl-1-methyl-pyridin-4(1H)-one | H |
| 356 | 5-Cl-pyridin-2-yl-NHC(O)CH₃ | 3-methyl-1-methyl-pyridin-2(1H)-one | H |
| 357 | 5-Cl-pyridin-2-yl-NHC(O)CH₃ | 3-methyl-1-[2-(4-methylpiperazin-1-yl)ethyl]-pyridin-2(1H)-one | H |
| 358 | 5-Cl-pyridin-2-yl-NHC(O)CH₃ | 3-methyl-1-[2-(1,4-oxazepan-4-yl)ethyl]-pyridin-2(1H)-one | H |
| 359 | 5-Cl-pyridin-2-yl-NHC(O)CH₃ | 3-methyl-1-[2-(4-hydroxypiperidin-1-yl)ethyl]-pyridin-2(1H)-one | Cl |
| 360 | 4-MeO-C₆H₄-C(O)NHMe | 3-methyl-1-[2-(dimethylamino)ethyl]-pyridin-2(1H)-one | H |

TABLE 42-continued

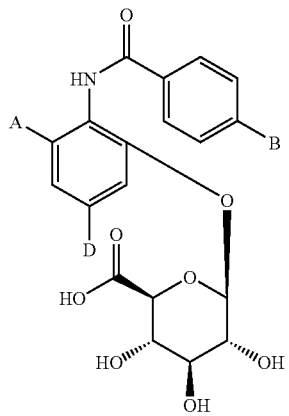

| No | A | B | D |
|---|---|---|---|
| 361 | MeO-C6H4-C(O)NH- | 5-methyl-1-(2-dimethylaminoethyl)pyrimidin-4(1H)-one | Cl |
| 362 | 5-Cl-pyridin-2-yl-NH-C(O)- | 4-methyl-2-(2-dimethylaminoethyl)pyridazin-3(2H)-one | H |
| 363 | MeO-C6H4-C(O)NH- | 3-methyl-1-(2-dimethylaminoethyl)pyridin-2(1H)-one | Cl |
| 364 | 5-Cl-pyridin-2-yl-NH-C(O)- | 3-methyl-1-(2-piperidin-1-ylethyl)-1H-pyrrol-2(5H)-one | H |
| 365 | 5-Cl-pyridin-2-yl-C(O)NH- | 3-methyl-1-(2-dimethylaminoethyl)pyridin-2(1H)-one | Cl |

INDUSTRIAL APPLICABILITY

The compounds of the present invention have an anticoagulation effect based on their ability to inhibit the activated blood coagulation factor X, and are useful as coagulation inhibitors or agents for prevention or treatment for diseases caused by thrombi or emboli, and therefore have industrial applicability.

The invention claimed is:

1. A benzene derivative of the following general formula (I) or a salt thereof:

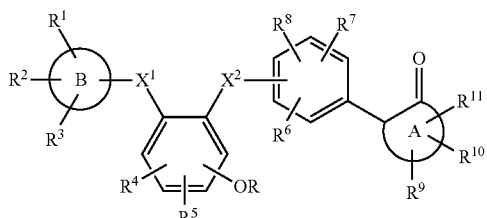

wherein $X^1$ is $-NR^{12}-C(=O)-$, or $-C(=O)-NR^{12}-$, $X^2$ is $-NR^{13}-C(=O)-$ or $-C(=O)-NR^{13}-$, Ring A is a 5- or 6-membered ring optionally having 1 or 2 double bonds and optionally having from 1 to 3 hetero atoms selected from the group consisting of N, S, and O, Ring B is a benzene ring, or 5- or 6-membered heteroaryl ring having from 1 to 3 hetero atoms selected from the group consisting of N, S, and O, R is a hydrogen atom or a sugar residue, $R^1$ to $R^8$ independently represent a hydrogen atom, a halogen atom, optionally-substituted lower alkyl, —O-(optionally-substituted lower alkyl), —O-(optionally-substituted 4- to 8-membered hetero ring having from 1 to 3 hetero atoms selected from the group consisting of N, S, and O), —CN, —$NH_2$, —N(optionally-substituted lower alkyl)$_2$, —NH(optionally-substituted lower alkyl), —NH(optionally-substituted 4- to 8-membered hetero ring having from 1 to 3 hetero atoms selected from the group consisting of N, S, and O), —$NHSO_2$(optionally-substituted lower alkyl), —N(optionally-substituted lower alkyl)$SO_2$(optionally-substituted lower alkyl), —$NO_2$, —COOH, —$CO_2$(optionally-substituted lower alkyl), —$CONH_2$, —CONH(optionally-substituted lower alkyl), —CON(optionally-substituted lower alkyl)$_2$, —OH, —$(CH_2)_n$—$NH_2$, —$(CH_2)_n$—N(optionally-substituted lower alkyl)$_2$, or —$(CH_2)_n$—NH(optionally-substituted lower alkyl), $R^9$ to $R^{11}$ independently represent a hydrogen atom, a halogen atom, optionally-substituted lower alkyl, —O-(optionally-substituted lower alkyl), —CN, —$NH_2$, —N(optionally-substituted lower alkyl)$_2$, —NH(optionally-substituted lower alkyl), —$NHSO_2$(optionally-substituted lower alkyl), —N(optionally-substituted lower alkyl)$SO_2$(optionally-substituted lower alkyl), —$NO_2$, —COOH, —$CO_2$(optionally-substituted lower alkyl), —$CONH_2$, —CONH(optionally-substituted lower alkyl), —CON(optionally-substituted lower alkyl)$_2$, —OH, —$(CH_2)_n$—N(optionally-substituted lower alkyl)$_2$, —$(CH_2)_n$—NH(optionally-substituted lower alkyl), —$(CH_2)_n$—$NH_2$, —$(CH_2)_n$—N(optionally-substituted 4- to 8-membered hetero ring having from 1 to 3 hetero atoms selected from the group consisting of N, S, and O)$_2$, —$(CH_2)_n$—NH(optionally-substituted 4- to 8-membered hetero ring having from 1 to 3 hetero atoms selected from the group consisting of N, S, and O), —$(CH_2)_n$—N(optionally-substituted lower alkyl)(optionally-substituted 4- to 8-membered hetero ring having from 1 to 3 hetero atoms selected from the group consisting of N, S, and O), —$(CH_2)_n$—(C=O)—N(optionally-substituted lower alkyl)$_2$, —$(CH_2)_n$—(C=O)—NH(optionally-substituted lower alkyl), —$(CH_2)_n$—(C=O)—$NH_2$, —$(CH_2)_n$—(C=O)—N(optionally-substituted 4- to 8-membered hetero ring having from 1 to 3 hetero atoms selected from the group consisting of N, S, and O)$_2$, —$(CH_2)_n$—(C=O)—NH(optionally-substituted 4- to 8-membered hetero ring having from 1 to 3 hetero atoms selected from the group consisting of N, S, and O), —$(CH_2)_n$—(C=O)—N(optionally-substituted lower alkyl)(optionally-substituted 4- to 8-membered hetero ring having from 1 to 3 hetero atoms selected from the group consisting of N, S, and O), —$(CH_2)_n$—O-(optionally-substituted lower alkyl), —$(CH_2)_n$-(optionally-substituted 4- to 8-membered hetero ring having from 1 to 3 hetero atoms selected from the group consisting of N, S, and O), —$(CH_2)_n$—O-(optionally-substituted 4- to 8-membered hetero ring having from 1 to 3 hetero atoms selected from the group consisting of N, S, and O), or —$(CH_2)_n$—(C=O)-(optionally-substituted 4- to 8-membered hetero ring having from 1 to 3 hetero atoms selected from the group consisting of N, S, and O), n is an integer of from 0 to 6, $R^{12}$ and $R^{13}$ independently represent a hydrogen atom or lower alkyl, provided that, in $R^1$ to $R^{11}$, when two lower alkyls bond to a nitrogen atom, then they may be taken together to form a 3- to 8-membered nitrogen-containing hetero ring.

2. The compound or a salt thereof according to claim 1, wherein in the formula (I) of claim 1, the group:

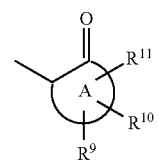

is among the following:

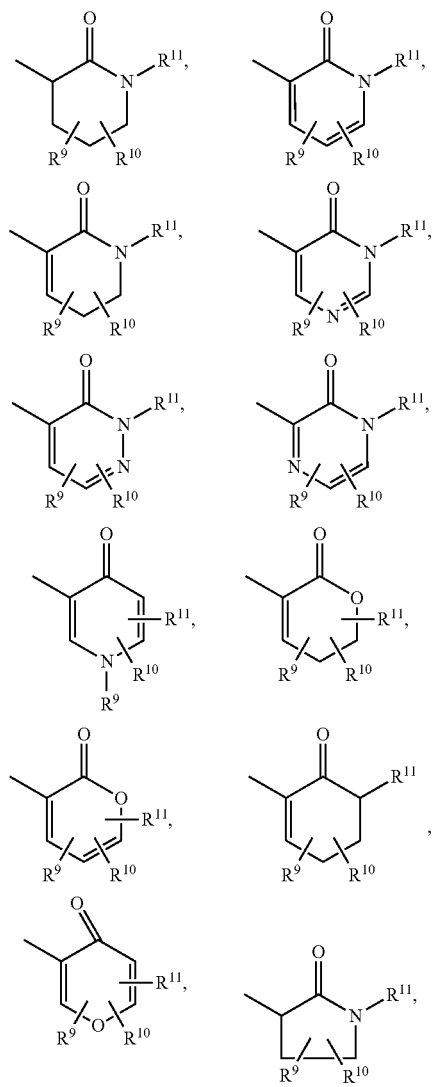

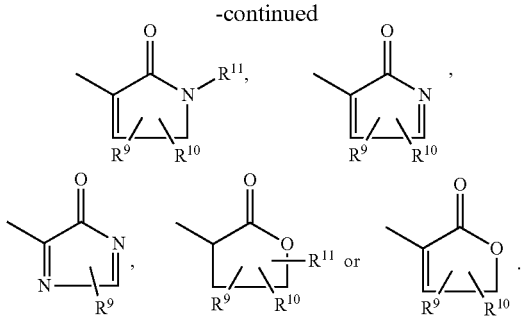

3. The compound or a salt thereof according to claim 1, wherein the group:

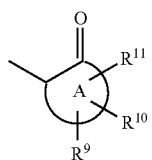

is among the following:

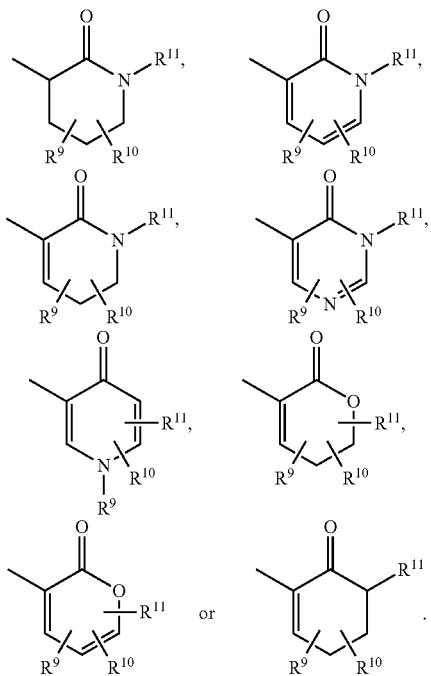

4. The compound or a salt thereof according to claim 1, wherein the group:

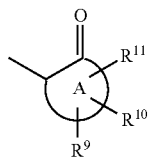

is among the following:

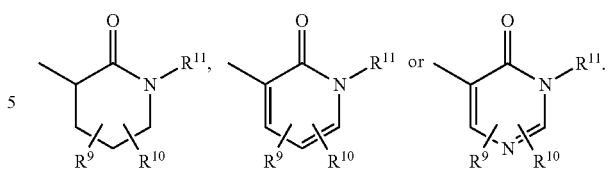

5. The compound or a salt thereof according to claims 1 to 4, wherein in the formula (I) of claim 1, the ring B is a benzene ring or a pyridine ring.

6. The compound or a salt thereof according to claim 5, wherein in the formula (I) of claim 1, R is a hydrogen atom or a sugar residue of glucuronic acid.

7. The compound or a salt thereof according to claim 6, wherein the optionally-substituted 4- to 8-membered hetero ring having from 1 to 3 hetero atoms is azetidine, pyrrolidine, piperidine, azepane, azocane, piperazine, morpholine, thiomorpholine, 1,4-diazepane, 1,4-oxazepane, 1,4-thiazepane, 1,5-diazocane, 1,5-oxazocane, 1,5-thiazocane, imidazole, triazole, thiazole, oxazole, isoxazole, pyrazole, pyridine, pyrazine, or pyrimidine.

8. The compound or a salt thereof according to claim 7, wherein the substituent in the optionally-substituted lower alkyl is from 1 to 3 substituents selected from the group consisting of —OH, CF$_3$, —CN, =O, —NH$_2$, —COOH, —COO-lower alkyl, —CONH$_2$, —CONH(lower alkyl), —CON(lower alkyl)$_2$, —O-lower alkyl, —NH(lower alkyl), —N(lower alkyl)$_2$, —NHCO(lower alkyl), —N(lower alkyl)CO(lower alkyl), —NHCONH$_2$, —NHCONH(lower alkyl), —NHCON(lower alkyl)$_2$, —N(lower alkyl)CONH(lower alkyl), —N(lower alkyl)CON(lower alkyl)$_2$, a halogen atom, —NHSO$_2$-(lower alkyl), —N(lower alkyl)SO$_2$— (lower alkyl), or —SO$_2$(lower alkyl), and the substituent in the optionally-substituted 4- to 8-membered hetero ring having from 1 to 3 hetero atoms selected from the group consisting of N, S, and O is from 1 to 3 substituents selected from lower alkyl, —OH, CF$_3$, —CN, =O, —NH$_2$, —COOH, —COO-lower alkyl, —CONH$_2$, —CONH(lower alkyl), —CON(lower alkyl)$_2$, —O-lower alkyl, —NH(lower alkyl), —N(lower alkyl)$_2$, —NHCO(lower alkyl), —N(lower alkyl)CO(lower alkyl), —NHCONH$_2$, —NHCONH(lower alkyl), —NHCON(lower alkyl)$_2$, —N(lower alkyl)CONH(lower alkyl), —N(lower alkyl)CON(lower alkyl)$_2$, a halogen atom, —NHSO$_2$— (lower alkyl), —N(lower alkyl)SO$_2$—(lower alkyl), and —SO$_2$(lower alkyl).

9. A benzene derivative of the following general formula (II) or a salt thereof:

(II)

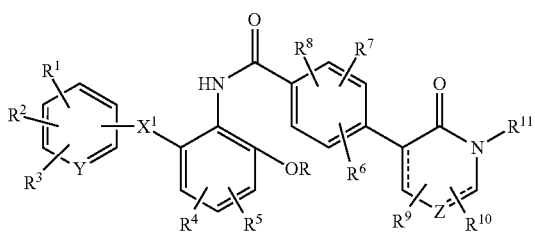

wherein X$^1$ is —NH—C(=O)— or —C(=O)—NH—,
Y is N or CH,
Z is N, NH, CH or CH$_2$,
R is a hydrogen atom or a sugar residue, R¹ to R⁸ independently represent a hydrogen atom, a halogen atom, lower alkyl, —O-lower alkyl, —O-(optionally-substituted 4- to 8-membered hetero ring having from 1 to 3 hetero atoms selected from N, S, and O), —CN, —NH₂, —N(lower alkyl)₂, —NH(lower alkyl), —NHSO₂(lower alkyl) or NO₂, R⁹ to R¹¹ independently represent a hydrogen atom, a halogen atom, lower alkyl, —(CH₂)ₙ—N(optionally-substituted lower alkyl)₂, —(CH₂)ₙ—NH(lower alkyl), —(CH₂)ₙ—NH₂, —(CH₂)ₙ—N(optionally-substituted 4- to 8-membered hetero ring having from 1 to 3 hetero atoms selected from the group consisting of N, S, and O)₂, —(CH₂)ₙ—NH(optionally-substituted 4- to 8-membered hetero ring having from 1 to 3 hetero atoms selected from the group consisting of N, S, and O), —(CH₂)ₙ—N(lower alkyl)(optionally-substituted 4- to 8-membered hetero ring having from 1 to 3 hetero atoms selected from the group consisting of N, S, and O), —(CH₂)ₙ—(C=O)—N(lower alkyl)₂, —(CH₂)ₙ—(C=O)—NH(lower alkyl), —(CH₂)ₙ—(C=O)—NH₂, —(CH₂)ₙ—(C=O)—N(4- to 8-membered hetero ring having from 1 to 3 hetero atoms selected from the group consisting of N, S, and O)₂, —(CH₂)ₙ—(C=O)—NH(4- to 8-membered hetero ring having from 1 to 3 hetero atoms selected from the group consisting of N, S, and O), —(CH₂)ₙ—(C=O)—N(lower alkyl)(4- to 8-membered hetero ring having from 1 to 3 hetero atoms selected from the group consisting of N, S, and O), —(CH₂)ₙ—O-lower alkyl, —(CH₂)ₙ-(optionally-substituted 4- to 8-membered hetero ring having from 1 to 3 hetero atoms selected from the group consisting of N, S, and O), —(CH₂)ₙ—O-(optionally-substituted 4- to 8-membered hetero ring having from 1 to 3 hetero atoms selected from the group consisting of N, S, and O), or —(CH₂)ₙ—(C=O)-(optionally-substituted 4- to 8-membered hetero ring having from 1 to 3 hetero atoms selected from the group consisting of N, S, and O), n is an integer of from 0 to 6, provided that the dotted parts in the formula are the same or different, each meaning a single bond or a double bond, and in R¹ to R¹¹, when two lower alkyl groups bonds to the nitrogen atom, they may be taken together to form a 3- to 8-membered nitrogen-containing hetero ring.

10. The compound or a salt thereof according to claim 9, wherein in the formula (II) of claim 9, R is a hydrogen atom or a sugar residue of glucuronic acid.

11. The compound or a salt thereof according to claim 1, selected from the group consisting of N-(5-chloropyridin-2-yl)-3-hydroxy-2-{[4-(1-methyl-4-oxo-1,4-dihydropyridin-3-yl)benzoyl]amino}benzamide, N-(5-chloropyridin-2-yl)-2-[(4-{1-[2-(dimethylamino)ethyl]-2-oxo-1,2-dihydropyridin-3-yl}benzoyl)amino]-3-hydroxybenzamide, N-(5-chloropyridin-2-yl)-3-hydroxy-2-[(4-{1-[2-(1,4-oxazepan-4-yl)ethyl]-2-oxo-1,2-dihydropyridin-3-yl}benzoyl)amino]benzamide, 5-chloro-N-(5-chloropyridin-2-yl)-3-hydroxy-2-{[4-(1-{2-[(1-methylpyridin-4-yl)oxy]ethyl}-2-oxo-1,2-dihydropyridin-3-yl)benzoyl]amino}benzamide, N-(5-chloropyridin-2-yl)-3-hydroxy-2-{[4-(1-methyl-2-oxo-1,2-dihydropyridin-3-yl)benzoyl]amino}benzamide, N-(5-chloropyridin-2-yl)-2-[(4-{1-[2-(dimethylamino)ethyl]-2-oxopiperidin-3-yl}benzoyl)amino]-3-hydroxybenzamide, 3-[(5-chloropyridin-2-yl)carbamoyl]-2-[(4-{1-[2-(dimethylamino)ethyl]-2-oxo-1,2-dihydropyridin-3-yl}benzoyl)amino]phenyl β-D-glucopyranosiduronic acid, N-(5-chloropyridin-2-yl)-3-hydroxy-2-[(4-{1-[2-(4-methylpiperazin-1-yl)ethyl]-2-oxo-1,2-dihydropyridin-3-yl}benzoyl)amino]benzamide, 4-{1-[2-(dimethylamino)ethyl]-2-oxo-1,2-dihydropyridin-3-yl}-N-{2-hydroxy-6-[(4-methoxybenzoyl)amino]phenyl}benzamide, N-(5-chloropyridin-2-yl)-3-hydroxy-2-[(4-{1-[2-(4-hydroxypiperidin-1-yl)ethyl]-2-oxo-1,2-dihydropyridin-3-yl}benzoyl)amino]benzamide, 5-chloro-N-(5-chloropyridin-2-yl)-2-[(4-{1-[2-(dimethylamino)ethyl]-2-oxo-1,2-dihydropyridin-3-yl}benzoyl)amino]-3-hydroxybenzamide, and 3-[(5-chloropyridin-2-yl)carbamoyl]-2-[(4-{1-[2-(dimethylamino)ethyl]-2-oxopiperidin-3-yl}benzoyl)amino]phenyl β-D-glucopyranosiduronic acid, or a salt thereof.

12. A pharmaceutical composition comprising the compound or a salt thereof according to claim 1 as an active ingredient.

13. The pharmaceutical composition according to claim 12, which is an activated blood coagulation factor X inhibitor.

14. The pharmaceutical composition according to claim 12, which is an anticoagulant.

15. A method of manufacturing an activated blood coagulation factor X inhibitor comprising the steps of admixing the compound or salt thereof according to claim 1 or 9 with a pharmaceutically acceptable carrier.

16. A method of manufacturing an anticoagulant comprising the steps of admixing the compound or salt thereof according to claim 1 or 9 with a pharmaceutically acceptable carrier.

17. A method for treating a patient with an activated blood coagulation factor X-associated disease, which comprises administering an effective amount of the compound or a salt thereof according to claim 1 or 9 to the patient.

18. A method for treating a patient with a disease caused by thrombi or emboli, which comprises administering an effective amount of the compound or a salt thereof according to claim 1 or 9 to the patient.

* * * * *

UNITED STATES PATENT AND TRADEMARK OFFICE
CERTIFICATE OF CORRECTION

| | | |
|---|---|---|
| PATENT NO. | : 8,022,208 B2 | |
| APPLICATION NO. | : 12/091099 | |
| DATED | : September 20, 2011 | |
| INVENTOR(S) | : Fukushi Hirayama et al. | |

It is certified that error appears in the above-identified patent and that said Letters Patent is hereby corrected as shown below:

COLUMN 1:

Line 27, "the characteristic of itself" should read --its--;
Line 28, "based on the" should be deleted; and
Line 48, "It" should read --it--.

COLUMN 8:

Line 56, "are" should read --is--.

COLUMN 10:

Line 22, "optical isomers" should read --and optical isomers.--.

COLUMN 15:

Line 13, "In" should read --In a--; and
Line 62, "C.," should read --C.;--.

COLUMN 16:

Line 55, "control;" should read --the control;--.

COLUMN 17:

Line 4, "control;" should read --the control;--.

Signed and Sealed this
Tenth Day of April, 2012

David J. Kappos
*Director of the United States Patent and Trademark Office*

CERTIFICATE OF CORRECTION (continued)
U.S. Pat. No. 8,022,208 B2

COLUMN 18:

Line 20, "radiations." should read --radiation.--.

COLUMN 22:

Line 44, "dropwisely" should be deleted.

COLUMN 24:

Line 58, "stifling" should read --stirring--.

COLUMN 104:

Table 28, Ex. 120, "Retension" should read --Retention--; and
Table 28, Ex. 121, "Retension" should read --Retention--.

COLUMN 146:

Table 39, Ex. 267, " 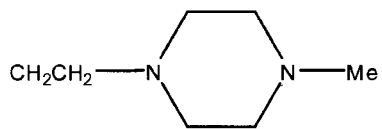 " should read -- 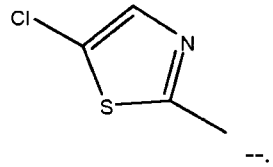 --.

COLUMN 150:

Table 40, Line 39, "340" should read --310--; and
Table 40, Line 45, "310" should read --311--.

COLUMN 160:

Line 11 Claim 1, "in the formula (I) of claim 1," should be deleted.

COLUMN 163:

Line 41 Claim 9, "bonds" should read --bond--.